United States Patent
Lai et al.

(10) Patent No.: US 11,547,100 B2
(45) Date of Patent: Jan. 10, 2023

(54) METHOD FOR SCREENING GENE EXPRESSION IN LINCRNA-DEFICIENT MICE OR RATS

(71) Applicants: Regeneron Pharmaceuticals, Inc., Tarrytown, NY (US); President and Fellows of Harvard College, Cambridge, MA (US)

(72) Inventors: Ka-Man Venus Lai, Seattle, WA (US); Guochun Gong, Pleasantville, NY (US); John Rinn, Boston, MA (US); David Frendewey, New York, NY (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 98 days.

(21) Appl. No.: 15/365,250

(22) Filed: Nov. 30, 2016

(65) Prior Publication Data
US 2017/0071173 A1 Mar. 16, 2017

Related U.S. Application Data

(63) Continuation of application No. 14/454,464, filed on Aug. 7, 2014, now Pat. No. 9,554,564.

(60) Provisional application No. 61/863,147, filed on Aug. 7, 2013.

(51) Int. Cl.
*A61D 19/04* (2006.01)
*C12Q 1/6876* (2018.01)
*A01K 67/027* (2006.01)

(52) U.S. Cl.
CPC .......... *A01K 67/0276* (2013.01); *A61D 19/04* (2013.01); *C12Q 1/6876* (2013.01); *A01K 2217/075* (2013.01); *A01K 2217/077* (2013.01); *A01K 2227/105* (2013.01); *A01K 2267/03* (2013.01); *A01K 2267/0393* (2013.01); *C12Q 2600/158* (2013.01); *C12Q 2600/178* (2013.01)

(58) Field of Classification Search
CPC .......... A01K 67/0276; A01K 2217/075; A01K 2217/077; A01K 2227/105; A01K 2267/03; A01K 2267/0393; A61D 19/04; C12Q 1/6876; C12Q 2600/158; C12Q 2600/178
See application file for complete search history.

(56) References Cited

U.S. PATENT DOCUMENTS

| | | | |
|---|---|---|---|
| 6,586,251 B2 | 7/2003 | Economides et al. | |
| 6,596,541 B2 | 7/2003 | Murphy et al. | |
| 7,105,348 B2 | 9/2006 | Murphy et al. | |
| 7,294,754 B2 | 11/2007 | Poueymirou et al. | |
| 7,576,259 B2 | 8/2009 | Poueymirou et al. | |
| 7,659,442 B2 | 2/2010 | Poueymirou et al. | |
| 8,697,851 B2 | 4/2014 | Frendewey et al. | |
| 2008/0078000 A1 | 3/2008 | Poueymirou et al. | |
| 2011/0104799 A1 | 5/2011 | Economides et al. | |
| 2013/0312129 A1 | 11/2013 | Frendewey et al. | |
| 2014/0235933 A1 | 8/2014 | Lee et al. | |
| 2014/0310828 A1 | 10/2014 | Lee et al. | |

FOREIGN PATENT DOCUMENTS

| RU | 2425880 | 8/2011 |
|---|---|---|
| WO | 2002/036789 A2 | 5/2002 |
| WO | 2016/149398 A1 | 9/2016 |

OTHER PUBLICATIONS

Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Niemann, Transgenic Research, 7: 73-75 (1997).*
Clark et al. Nature Reviews: 4: 825-833, 2003.*
Ellenbroek, Disease Models & Mechanisms, 9: 1079-1087, 2016.*
Creed et al., Movement Disorders, vol. 33, No. 5, 2018.*
Kohtz, Frontiers in Genetics, 5(45): 1-3, Mar. 2014.*
Ransohoff et al., Nat Rev Mol Cell Biol.; 19(3): 143-157, Mar. 2018.*
Kirov et al., PLOS ONE, 10(8): e0134155: 1-17, Aug. 2015.*
Guttman, Nature, 477: 295-300, 2011.*
Davey et al., Am J Physiol Endocrinol Metab 291: E429-E438, 2006.*
Haruyama et al., Curr Protoc Cell Biol. Mar. 2009 ; Chapter: Unit-19, pp. 1-12.*
Reporter Gene Assays from ThermoFisher Scientific, Accessed from https://www.thermofisher.com/us/en/home/references/gibco-cell-culture-basics/transfection-basics/reporter-gene-assays.html on Dec. 30, 2021, pp. 1-2.*
Zhang, et al., (Jul. 26, 2012) "The lncRNA Malat1 is dispensable for mouse development but its transcription plays a cis-regulatory role in the adult," Cell Reports 2(1):111-123.
Zhao, et al., (2008) "The Shadow Regulator behind Xist," Science, 322:750-756.
International Search Report & Written Opinion with respect to PCT/US2014/050178, dated Jan. 29, 2015.
Adams, et al., (2005) "A genome-wide, end-sequenced 129Sv BAC library resource for targeting vector construction," Genomics, 86:753-758.

(Continued)

*Primary Examiner* — Anoop K Singh
*Assistant Examiner* — Magdalene K Sgagias
(74) *Attorney, Agent, or Firm* — Rita S. Wu; Yongjin Choi; FisherBroyles, LLP

(57) ABSTRACT

Genetically modified non-human animals are provided that exhibit a functional lack of one or more lncRNAs. Methods and compositions for disrupting, deleting, and/or replacing lncRNA-encoding sequences are provided. Genetically modified mice that age prematurely are provided. Also provided are cells, tissues and embryos that are genetically modified to comprise a loss-of-function of one or more lncRNAs.

8 Claims, 12 Drawing Sheets

Specification includes a Sequence Listing.

(56) References Cited

OTHER PUBLICATIONS

Anguera, et al., (Sep. 2011) "Tsx Produces a Long Noncoding RNA and has General Functions in the Germline, Stem Cells, and Brain," PLOS Genetics, 7(9):1-14, e1002248.
Bacchetti, et al., (1977) "Transfer of the gene for thymidine kinase to thymidine kinase-deficient human cells by purified herpes simplex viral DNA," PNAS, 74(4):1590-1594.
Barthold (2004) "Genetically altered mice: phenotypes, no phenotypes, and Faux phenotypes," Genetica, 122:75-88.
Bishop, et al., (2011) "Alveolar Capillary Dysplasia," American Journal Respiratory Critical Care Medicine, 184:172-179.
Bradley, et al., (2012) "The mammalian gene function resource: the international knockout mouse consortium," Mamm. Genome, 23:580-586.
Brevini, et al., (2010) "No shortcuts to pig embryonic stem cells," Theriogenology, 74:544-550.
Cabili, et al., (2011) "Integrative annotation of human large intergenic noncoding RNAs reveals global properties and specific subclasses," Genes & Development, 25:1915-1927.
Cao, et al., (2009) "Isolation and Culture of Primary Bovine Embryonic Stem Cell Colonies by a Novel Method," Journal of Experimental Zoology, 311A:368-376.
Carninci, et al., (Sep. 2, 2005) "The transcriptional landscape of the mammalian genome," Science, 309(5740):1559-63.
Carpenter, et al., (Aug. 16, 2013) "A Long Noncoding RNA Mediates Both Activation and Repression of Immune Response Genes," Science, 341(6147):789-792.
Derrien, et al., (2012) "The GENCODE v7 catalog of human long noncoding RNAs: Analysis of their gene structure, evolution, and expression," Genome Research, 22:1775-1789.
Djebali, et al., (Sep. 5, 2012) "Landscape of transcription in human cells," Nature, 489:101-108.
Frendewey, et al., (2010) "Chapter 17—The Loss-of-Allele Assay for ES Cell Screening and Mouse Genotyping," Methods in Enzymology, 476:295-307.
Grote, et al., (Jan. 28, 2013) "The Tissue-Specific lncRNA Fendrr is an Essential Regulator of Heart and Body Wall Development in the Mouse," Developmental Cell, 24:206-214.
Guttman, et al., (Mar. 12, 2009) "Chromatin signature reveals over a thousand highly conserved large noncoding RNAs in mammals," Nature, 458:223-227.
Holschneider and Shih (2000) "Genotype to Phenotype: challenges and opportunities," Int. J. Developmental Neuroscience, 18:615-618.
Hostikka and Capecchi, (Jan. 1998) "The mouse Hoxc11 gene: genomic structure and expression pattern," Mech. Dev., 70(1-2):133-145.
Houdebine (2009) "Methods to Generate Transgenic Animals," Genetic Engineering in Livestock, New Applications and Interdisciplinary Perspectives, Ed. Engelhard et al., pp. 31-47.
Huarte et al., (2010) "A large intergenic non-coding RNA induced by p53 mediates global gene repression in the p53 response," Cell, 142(3):409-419.
Kapranov, et al., (Jun. 8, 2007) "RNA Maps Reveal New RNA Classes and a Possible Function for Pervasive Transcription," Science, 316:1484-1488.
Khalil, et al., (Jul. 14, 2009) "Many human large intergenic noncoding RNAs associate with chromatin modifying complexes and affect gene expression," PNAS, 106(28):11667-11672.
Kozak (1987) "An analysis of 5'-noncoding sequences from 699 vertebrate messenger RNAs," Nucleic Acids Research, 15(20):8125-8148.
Kozak, et al., (1987) "At least six nucleotides preceding the AUG initiator codon enhance translation in mammalian cells," Journal Molecular Biology, 196(4):947-950.
Leighton, et al., (May 4, 1995) "Disruption of imprinting caused by deletion of the H19 gene region in mice," Nature, 375(6526):34-39.
Lu, et al., (2008) "The apical ectodermal ridge is a timer for generating distal limb progenitors," Development, 135:1395-1405.
Marahrens, et al., (1997) "Xist-deficient mice are defective in dosage compensation but not spermatogenesis," Genes & Development, 11:156-166.
Marin-Bejar, et al., (2013) "Pint lincRNA connects the p53 pathway with epigenetic silencing by the Polycomb repressive complex 2," Genome Biology, 14:R104.
Mattick, (Apr. 2009) "The Genetic Signatures of Noncoding RNAs," PLOS Genetics, 5(4):e1000459.
"MiRNA knockouts," access web page at mcmanuslab.ucsf.edu/microma_knockout.
Mohammad, et al., (2010) "Kcnq1ot1 noncoding RNA mediates transcriptional gene silencing by interacting with Dnmt1," Development, 137:2493-2499.
Paris and Stout (2010) "Equine embryos and embryonic stem cells: Defining reliable markers of pluripotency," Theriogenology, 74:516-524.
Pefanis, et al., (2014) "Noncoding RNA transcription targets AID to divergently transcribed loci in B cells," Nature, 514:389-405.
Pefanis, et al., (2015) "RNA Exosome-Regulated Long Non-Coding RNA Transcription Controls Super-Enhancer Activity," Cell, 161:774-789.
Prosser, et al., (2011) "A resource of vectors and ES cells for targeted deletion of microRNAs in mice," Nature Biotechnology, 29:840-845.
Rinn, et al., (Jun. 29, 2007) "Functional Demarcation of Active and Silent Chromatin Domains in Human HOX Loci by Noncoding RNAs," Cell, 129:1311-1323.
Rodent retrieved from http://www.britannica.com/animal/rodent on May 31, 2016.
Ryan and Sigmund (2002) "Use of Transgenic and Knockout Strategies in Mice," Seminars in Nephrology, 22(2):154-160.
Sado, et al., (2001) "Regulation of imprinted X-chromosome inactivation in mice by Tsix," Development, 128:1275-1286.
Sauvageau, et al., (2013) "Multiple knockout mouse models reveal lincRNAs are required for life and brain development," ELife, 2:e01749.
Schorderet and Duboule, (May 26, 2011) "Structural and Functional Differences in the Long Non-Coding RNA Hotair in Mouse and Human," PLOS Genetics, 7(5):e1002071.
Sleutels, et al., (Feb. 14, 2002) "The non-coding Air RNA is required for silencing autosomal imprinted genes," Nature, 415(6873):810-813.
Szafranski, et al., (2013) "Small noncoding differentially methylated copy-number variants, including lncRNA genes, cause a lethal lung developmental disorder," Genome Research, 23:23-33.
Takahashi, et al., (2009) "Deletion of Gtl2, imprinted non-coding RNA, with its differentially methylated region induces lethal parent-origin-dependent defects in mice," Human Molecular Genetics, 18(10):1879-1888.
Thai, et al., (Apr. 27, 2007) "Regulation of the Germinal Center Response by MicroRNA-155," Science, 316(5824):604-608.
Tsai, et al., (Aug. 6, 2010) "Long Noncoding RNA as Modular Scaffold of Histone Modification Complexes," Science, 329(5992):689-693.
Ulitsky and Bartel (2013) "lincRNAs: Gnomics, Evolution, and Mechanisms," Cell, 154:26-46.
Valenzuela, et al., (2003) "High-throughput engineering of the mouse genome coupled with highresolution expression analysis," Nature Biotechnology, 21:652-659.
Young, et al., (Mar. 29, 2005) "The Noncoding RNA Taurine Upregulated Gene 1 is Required for Differentiation of the Murine Retina," Current Biology, 15:510-512.
Zambrowicz, et al., (Apr. 15, 1997) "Disruption of overlapping transcripts in the ROSA beta geo 26 gene trap strain leads to widespread expression of beta-galactosidase in mouse embryos and hematopoietic cells," PNAS, 94(8):3789-3794.
Dennis (2002) "Welfare issues of genetically modified animals," ILAR Journal, 43(2):100-109.
Goff, et al., (2015) "Spatiotemporal expression and transcriptional perturbations by long noncoding RNAs in the mouse brain," PNAS, 112(22):6855-6862.
Gong, et al., (2013) "93. Differentiation-Dependent Self-Deleting Cassette (DDSDC), a new strategy for rapid and automatic genera-

(56) References Cited

OTHER PUBLICATIONS tion of gene targeted mice free of selection cassette," Transgenic Res., 23:201-250, 11th Transgenic Technology Meeting (TT2013) Baiyum International Convention Center, Guangzhou/Canton, P.R. China, Feb. 25-27, 2013 (2 pages).
Gong, et al., (2014) "56. LincRNA Pint knockout mice display early ageing associated phenotypes," Transgenic Res., 23:850 Abstract, 12th Transgenic Technology Meeting (TT2014) The Assembly Rooms, Edinburgh, Scotland, United Kingdom, Oct. 6-8, 2014 (2 pages).
Gordon, et al., (2010) "Increased Expression of Angiogenic Genes in the Brains of Mouse Meg3-Null Embryos," Endocrinology, 2443-2452.
Li, et al., (2013) "Targeted disruption of Hotair leads to homeotic transformation and gene de-repression," Cell Rep., 5(1):3-12, doi:10.1016/j.celrep.2013.09.003.
Li and Chang, (2014) "Physiological roles of long noncoding RNAs: Insights from knockout mice," Trends Cell Biol., 24(10):594-602, doi:10.1016/j.tcb.2014.06.003.
Liu, et al., (2013) Inheritable and Precise Large Genomic Deletions of Non-Coding RNA Genes in Zebrafish Using TALENs, PLOS ONE, 8(10):e76387.
Mattick, et al., (2013) "Probing the phenomics of noncoding RNA," eLife, 2:e01968, DOI: 10.7554/eLife.01968.
Shi, et al., (2013) "Long non-coding RNAs: A new frontier in the study of human diseases," Cancer Letters, 339:159-166.
Shiekhattar (2013) "PINTing for P53," Genome Biology, 14:132, (3 pages).
Steen, et al., (2013) "Neuropsychological Deficits in Mice Depleted of the Schizophrenia Susceptibility Gene CSMD1," PLOS ONE, 8(11):e79501.
Tallack, et al., (2012) "Novel roles for KLF1 in erythropoiesis revealed by mRNA-seq," Genome Research, 22(12):2385-2398.
Wu, et al., (2013) "Roles of long noncoding RNAs in brain development, functional diversification and neurodegenerative diseases," Brain Research Bulletin, 97:69-80.
Zhou et al., (2009) "Developing tTA transgenic rats for inducible and reversible gene expression," International Journal of Biological Sciences, 5:171-181.
Zhou, et al., (2010) "Activation of paternally expressed genes and perinatal death caused be deletion of the Gtl2 gene," Development and Stem Cells, 137(16):2643-2652.
Zhou, et al., (2012) "MEG3 noncoding RNA: a tumor suppressor," Journal of Molecular Endocrinology, 48(3):R45-R53 DOI:10.1530/JME-12-0008.
Extended European Search Report with respect to EP 14834544.0, dated Jun. 26, 2017.
Extended European Search Report with respect to EP 17152034.9, dated Apr. 6, 2017.
Armit, "Into the blue: the importance of murine lacZ gene expression profiling in understanding and treating human disease," Disease Models & Mechanisms, 2015, 8(11):1341-1343.
Lai, et al., "A study of twenty mouse LincRNA deletion knockouts with lacZ reporter knock-ins reveals unique gene expression patterns and subtle phenotypes," Baiyun International Convention Center, Guangzhou, P.R. China, International Society for Transgenic Technologies, Feb. 25-27, 2013 (9 pages), enlarged.
Li, et al., (2017) "Genome-wide discovery of long intergenic noncoding RNAs and their epigenetic signatures in the rat," Scientific Reports, 7:14817.
Tong, et al. (2010) "Production of p53 gene knockout rats by homologous recombination in embryonic stem cells," Nature, 467(7312):211-213.
Elling, et al. "Genetic Models Reveal cis and trans Immune-Regulatory Activities for lincRNA-Cox2," Cell Reports, 25:1511-1524 (Nov. 6, 2018).
Kutter, et al. "Rapid Turnover of Long Noncoding RNAs and the Evolution of Gene Expression," PLoS Genetics, 8(7):e1002841, Jul. 2012 (15 pages).
Marques and Ponting "Catalogues of mammalian long noncoding RNAs: modest conservation and incompleteness," Genome Biology, 10:R124, 2009 (12 pages).
Kashi et al. (2016). Biochimica et Biophysica Acta—Gene Regulatory Mechanisms 1859:3-15.
Blythe et al. (2016). Biochimica et Biophysica Acta (BBA) Gene Regulatory Mechamisms: 1859(1):46-58.
GenBank Accession No. AK011788, Oct. 6, 2021 https://www.ncbi.nlm.nih.gov/nuccore/AK011788?report=GenBank.
GenBank Accession No. AK032721, Oct. 6, 2010 https://www.ncbi.nlm.nih.gov/nuccore/AK032721?report=GenBank.
Genbank Accession No. NR_040269 XR_106056, Jul. 17, 2013 https://www.ncbi.nlm.nih.gov/nuccore/339409192?sat=17&satkey=38074726.
Wang, et al., (Apr. 7, 2011) "A long noncoding RNA maintains active chromatin to coordinate homeotic gene expression," Nature, 472:120-124.
West, et al., (2015) "A lacZ reporter gene expression atlas for 313 adult KOMP mutant mouse lines," Genome Research, 25:598-607, doi:10.1101/gr.184184.114.

\* cited by examiner

Figure 11

Table 2. Summary of *lacZ* reporter expression in embryo and adult tissue

| LincRNA | Embryo | Brain | Heart | Lungs | Liver | Ribs | Spleen | Intestine | Stomach | Kidney | Urogenital | Hindlimb |
|---|---|---|---|---|---|---|---|---|---|---|---|---|
| *Celrr* | + | + | | | | + | | | | | | + |
| *Crnde* | + | + | | + | | + | | | | | + | + |
| *Eldr* | + | | | | | | | | | | + | |
| *Fendrr* | + | | | + | | | | | | | | |
| *Hair1* | + | | | | + | | | | | | | |
| *Hotair* | + | | | | | | | | | | | |
| *Hottip* | + | | | | | | | + | | | + | + |
| *Hoxa11os* | + | | | | | + | | + | | + | + | + |
| *Pantr1* | + | + | | | | + | | | | + | | |
| *Pantr2* | + | + | | | | | | | | | | |
| *Ptgs2os2* | + | | | | | | | | | | | |
| *lincenc1* | + | + | + | + | | | | + | | | | + |
| *Trp53cor1* | + | | | | | | | | | | | |
| *Pint* | + | + | + | | + | + | + | + | + | + | + | + |
| *lincppara* | + | + | | | | | | | + | | + | |
| *Mannr* | + | | | + | | | | | | | | |
| *Haglr* | + | | | | | | | | | | | |
| *Perli* | + | + | | | | | | | | | | |
| *Kantr* | + | | | | | | | | | | | |
| *Tug1* | + | + | + | | | + | | | | + | + | |

METHOD FOR SCREENING GENE EXPRESSION IN LINCRNA-DEFICIENT MICE OR RATS

CROSS-REFERENCE TO RELATED APPLICATIONS

This application is a continuation application of U.S. application Ser. No. 14/454,464, filed Aug. 7, 2014, which application claims the benefit of U.S. Provisional Application No. 61/863,147, filed Aug. 7, 2013, and both of which applications are hereby incorporated herein in its entirety by reference.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 2016-11-30-3100US02-SEQ-LIST_ST25.txt, created on Nov. 30, 2016, and having a size of 1 kilobyte, and is filed concurrently with the specification. The sequence listing contained in this ASCII formatted document is part of the specification and is herein incorporated by reference in its entirety.

FIELD OF THE INVENTION

Non-human animals, cells, and tissues, and methods for making them, that comprise one or more deficiencies in long non-coding RNAs ("lncRNAs"). Non-human animals, and methods for making them, that comprise nonfunctional lncRNAs, or a knockout of one or more lncRNAs. Genetically modified non-human animals that exhibit phenotypes consistent with premature aging.

BACKGROUND OF THE INVENTION

The long non-coding RNAs (lncRNAs) and a subclass known as large intergenic non-coding RNAs (lincRNAs) comprise approximately 15,000 diverse transcripts in mammals that resemble mRNAs in structure, synthesis, and the chromatin character of their genes. Functions or phenotypes associated with particular lncRNAs are not known for the vast majority of identified lncRNAs. It is believed that some lncRNAs participate in transcriptional control as activators or repressors of transcription in animals; others may function post-translationally or by some other mechanism. Thus, the ability to manipulate lncRNAs may provide a tool for developing phenotypes of interest depending upon the identity and function of the lncRNA. There is a need in the art for methods and compositions for manipulating lncRNAs, and a need for generating phenotypes of non-human animals through lncRNA manipulation.

SUMMARY OF THE INVENTION

Non-human animals, cells, tissues, and embryos are provided that comprise nonfunctional long non-coding RNAs (lncRNAs), including but not limited to knockouts of one or more lncRNAs. Methods and compositions for manipulating lncRNA expression are provided. Targeting compositions directed to modifying or knocking out lncRNAs are also provided. Non-human animals, cells, and tissues are provided that exhibit a phenotype associated with non-function of one or more lncRNAs.

In one aspect, a non-human animal comprising in its genome at least one modified lncRNA locus is provided, wherein the modified lncRNA locus comprises a loss-of-function mutation in a nucleic acid sequence that encodes a lncRNA.

In one embodiment, the lncRNA is a long intergenic non-coding RNA (lincRNA).

In one aspect, the loss-of-function mutation is characterized by a disruption or a knockout of at least one lncRNA function.

In one embodiment, the modified lncRNA locus comprises a deletion of one or more exons that encode the lncRNA or a portion thereof. In one aspect, the disruption or knockout comprises a deletion of one or more exons within the lncRNA locus starting in a second exon of a lncRNA locus; a deletion of one or more exons within the lncRNA locus starting in a first exon of a lncRNA locus; or deletion of an entire RNA coding region of a lncRNA locus.

In one aspect, the disruption or knockout comprises a replacement of a lncRNA locus or a portion thereof with an insert nucleic acid. In one embodiment, the insert nucleic acid comprises a first nucleotide sequence that encodes a reporter. In some such cases, the first nucleotide sequence is operably linked to a promoter that drives expression of the reporter. In one embodiment, the first nucleotide sequence that encodes the reporter is positioned in a lncRNA locus in operable linkage with an endogenous lncRNA promoter, wherein the endogenous lncRNA promoter drives expression of the nucleotide sequence. In such cases, the expression of the nucleic acid sequence follows an expression pattern of the lncRNA. In one aspect, the insert nucleic acid comprises a Kozak consensus sequence. In a specific embodiment, the first nucleotide sequence of the insert nucleic acid comprises a Kozak consensus sequence.

In one embodiment, the insert nucleic acid further comprises a second nucleotide sequence that encodes a selectable marker, wherein the second nucleotide sequence is operably linked to a promoter.

In one aspect, the insert nucleic acid comprises site-specific recombination sites flanking a segment encoding the reporter and/or a segment encoding the selectable marker.

In various aspects and embodiments, the replacement of the lncRNA locus or portion thereof comprises replacement of one or more exons within a lncRNA locus starting in the second exon of the lncRNA locus with the insert nucleic acid; replacement of one or more exons within a lncRNA locus starting in the first exon of the lncRNA locus with the insert nucleic acid; or replacement of the entire RNA coding region of a lncRNA locus with the insert nucleic acid.

In one embodiment, a non-human animal provided herein is characterized by having one or more following phenotypes: (a) a premature aging-associated phenotype; (b) perinatal lethality; (c) a defect in lung development; (d) a morphological malformation in the tail and hind limbs; (e) a loss of muscle mass in one or more tissues; or (f) a combination thereof of any of (a)-(e).

In one aspect, a non-human animal provided herein comprises a disruption or knockout of the lncRNA Pint, and the non-human animal is characterized by a premature aging-associated phenotype comprising: (a) a slower growth rate than that of a wild type control; (b) a decline in muscle strength; (c) fibrosis; (d) a lower body fat content than that of the wild type control; (e) a lower femur bone mineral density and bone mass than that of the wild type control; (f) a decreased muscle mass as compared with that of the wild type control; (g) a decrease in median longevity; (h) lordokyphosis; (i) organ atrophy; or (j) a combination thereof of any of (a)-(i).

In one embodiment, a non-human animal provided herein exhibits a defect in brain development. In some such cases, the lncRNA is Pantr2, Kantr, Peril, Celrr, Pantr1, Crnde, lincenc1, Pint, lincppara, or Tug1.

In various aspects and embodiments, the non-human animal is a mammal. In various aspects and embodiments, the mammal is a rodent, e.g., a mouse, a rat or a hamster. In various aspects and embodiments, the mammal is an ovine, bovine, or porcine species.

In one aspect, a genetically modified non-human animal is provided, wherein the genetic modification results in a loss-of-function of a lncRNA.

In one aspect, a genetically modified non-human animal is provided, wherein the genetic modification comprises a disruption or a knockout of one or more lncRNAs.

In one embodiment, the genetic modification comprises a disruption or knockout of at least two lncRNAs. In one embodiment, the genetic modification comprises a disruption or knockout of at least three, four, five, or six lncRNAs.

In one embodiment, the genetic modification comprises a disruption or knockout of one or more lncRNAs and within the lncRNA locus a gene encoding a detectable moiety (reporter) operably linked to a promoter of a disrupted or knocked out lncRNA. In one embodiment, the gene encoding the detectable moiety (reporter) is selected from lacZ (encoding β-galactosidase), GFP, eGFP, mPlum, mCherry, tdTomato, mStrawberry, J-Red, DsRed, mOrange, mKO, mCitrine, Venus, YPet, enhanced yellow fluorescent protein (EYFP), Emerald, CyPet, cyan fluorescent protein (CFP), Cerulean, T-Sapphire, luciferase, alkaline phosphatase, and a combination thereof.

In one embodiment, the genetic modification comprises a disruption or knockout of one or more lncRNAs and within the lncRNA locus a gene encoding a detectable moiety (reporter) operably linked to a promoter that drives expression of the detectable moiety.

In various aspects and embodiments, the detectable moiety includes any reporter gene known in the art.

In one aspect, a genetically modified non-human animal is provided, wherein the genetic modification comprises a disruption of a lncRNA nucleic acid sequence encoding a lincRNA selected from the group consisting of HOTAIR, HOTTIP, Hoxa11os (formerly named HoxA11as), Pantr1 (formerly named lincRNA-Brn1-a), Pantr2 (formerly named lincRNA-Brn1-b), Ptgs2os2 (formerly named lincRNA-Cox2), Eldr (formerly named Fabl and lincRNA-Egfr), Lincenc1 (formerly named lincRNA-Enc1), Mannr (formerly named lincRNA-Evi1), Fendrr (formerly named lincRNA-Foxf1), Halr1 (formerly named Haunt and lincRNA-HoxA1), Haglr (formerly named lincRNA-HoxD3), Celrr (formerly named Celr and lincRNA-Insig2), Crnde (formerly named lincRNA-Irx5), Kantr (formerly named Spasm and lincRNA-Jarid1c), Pint (formerly named linc-Pint and lincRNA-Mkln1), Trp53cor1 (formerly named lincRNA-p21), lincppara (formerly named lincRNA-Ppara), Peril (formerly named lincRNA-Sox2), Tug1 (formerly named lincRNA-Tug1), and a combination thereof.

In one aspect, a genetically modified non-human animal is provided, wherein the genetic modification comprises a disruption or knockout of Pint (formerly named linc-Pint and lincRNA-Mkln1).

In one aspect, a nucleic acid locus is provided, comprising a disruption of a lncRNA. In one embodiment, the disruption comprises a knockout of the lncRNA. In one embodiment, the disruption comprises a placement of a gene encoding a detectable moiety operably linked to a promoter of the lncRNA. In one embodiment, the disruption comprises a knockout of the lncRNA and placement of a gene encoding a detectable moiety in operable linkage with the promoter of the lncRNA.

In one aspect, a nucleic acid construct is provided, comprising at least one targeting sequence that targets the construct to a locus comprising a lncRNA, wherein the construct is capable of disrupting transcription of the lncRNA, knocking out the lncRNA, or replacing the lncRNA.

In one embodiment, the nucleic acid construct further comprises a detectable moiety (with or without an added promoter that drives expression of the detectable moiety). In one embodiment, the nucleic acid construct further comprises a selectable marker gene driven by a promoter. In one embodiment, the nucleic acid construct comprises both a detectable moiety (with or without its own promoter), and a selectable marker gene driven by a promoter. In one embodiment, the selectable marker and/or the detectable moiety are flanked upstream and downstream with site-specific recombination sites that direct an excision of the detectable moiety and/or the selectable marker.

In one embodiment, a targeting vector is provided. In one aspect, the targeting vector comprises an insert nucleic acid flanked by 5' and 3' homology arms that can undergo homologous recombination with an lncRNA locus of interest. In one embodiment, the insert nucleic acid of the targeting vector comprises a first nucleic acid sequence that encodes a reporter. In one aspect, following the homologous recombination with the lncRNA locus of interest, the first nucleic acid sequence that encodes the reporter is operably linked to an endogenous promoter that drives expression of an lncRNA at the lncRNA locus. In one embodiment, first and/or second nucleic acid sequence of the insert nucleic acid of the targeting vector further comprises a Kozak consensus sequence. In one embodiment, the targeting vector further comprises a promoter that drives expression of the promoter.

In one aspect, the insert nucleic acid of the targeting vector further comprises a second nucleic acid sequence that encodes a selectable marker, wherein the second nucleic acid is operably linked to a promoter. In one embodiment, the targeting vector further comprises site-specific recombination sites flanking a segment encoding the reporter and/or a segment encoding the selectable marker nucleic acid.

In one aspect, a non-human animal that exhibits a premature aging-associated phenotype is provided, wherein the non-human animal comprises a modification that renders Pint nonfunctional. In one embodiment, the modification is a disruption of an RNA-coding sequence of a Pint locus. In one embodiment, the modification is a deletion of an entire RNA-coding sequence of a Pint locus. In one embodiment, the modification comprises an insertion of a targeting vector into a Pint locus, such that the animal no longer makes a functional Pint.

In one embodiment, the modification further comprises at the Pint locus a detectable moiety (e.g., a reporter gene with or without its own promoter) and optionally a selectable marker. In one embodiment, the detectable moiety and/or the selectable marker are flanked upstream and downstream with site-specific recombination sites that direct an excision of the detectable moiety and/or the selectable marker. In one embodiment, the non-human animal further comprises and inducible site specific recombinase that is compatible with the site-specific recombinase sites.

In one aspect, a cell, tissue or embryo of a non-human animal is provided, wherein the cell or tissue lacks a nucleic acid sequence that encodes a functional lincRNA selected from the group consisting of HOTAIR, HOTTIP, Hoxa11os (formerly named HoxA11as), Pantr1 (formerly named lincRNA-Brn1-a), Pantr2 (formerly named lincRNA-Brn1-b), Ptgs2os2 (formerly named lincRNA-Cox2), Eldr (formerly named Fabl and lincRNA-Egfr), Lincenc1 (formerly named lincRNA-Enc1), Mannr (formerly named lincRNA-Evi1), Fendrr (formerly named lincRNA-Foxf1), Halr1 (formerly named Haunt and lincRNA-HoxA1), Haglr (formerly named Mdgt and lincRNA-HoxD3), Celrr (formerly named Celr and lincRNA-Insig2), Crnde (formerly named lincRNA-Irx5), Kantr (formerly named Spasm and lincRNA-Jarid1c), Pint (formerly named linc-Pint and lincRNA-Mkln1), Trp53cor1 (formerly named lincRNA-p21), lincppara (formerly named lincRNA-Ppara), Peril (formerly named lincRNA-Sox2), Tug1 (formerly named lincRNA-Tug1), and a combination thereof.

In one embodiment, the cell or tissue that lacks a nucleic acid sequence that encodes a functional lincRNA lacks a functional Pint (formerly known as lincRNA-Mlkn1).

In one aspect a nucleic acid construct is provided, comprising an upstream homology arm and a downstream homology arm, wherein the upstream and downstream homology arms target a lncRNA locus, wherein the construct is capable of disrupting transcription of the lncRNA, knocking out the lncRNA, or replacing the lncRNA.

In various aspects and embodiments, targeting constructs that target a lncRNA locus comprise a sequence selected from a Kozak sequence, a sequence encoding a detectable moiety (e.g., a reporter, e.g., a reporter as described herein; with, e.g., optionally a promoter operably linked thereto), a nucleic acid sequence encoding selectable marker (with, e.g., a promoter operably linked thereto), and a combination thereof. In one embodiment, reporter and/or selectable marker are flanked with site specific recombination sites that are arranged so as to effectuate a deletion of the nucleic acid sequence encoding the selectable marker gene and/or the nucleic acid sequence encoding the detectable moiety. In one embodiment, the construct does not comprise a promoter operably linked to the detectable moiety.

In one aspect, a method for disrupting a lncRNA is provided, comprising inserting a nucleic acid sequence within a lncRNA locus, wherein the insertion disrupts the transcription of the lncRNA, deletes one or more lncRNA-coding regions, or deletes an entire coding sequence of a lncRNA.

In one aspect, a method for making a non-human animal that comprises a disruption or a knockout of a lncRNA is provided, comprising modifying a genome of a non-human animal such that the non-human animal no longer expresses a functional version of the lncRNA. In one embodiment, the method comprises a step of employing a targeting vector to disrupt transcription of the lncRNA, to delete one or more lncRNA-coding regions, or deletes an entire coding sequence of the lncRNA in the genome of the non-human animal.

In one aspect, a method for making a non-human animal that comprises a knockout of a lncRNA function is provided, comprising modifying a genome of a pluripotent or totipotent non-human animal cell to disrupt the transcription of the lncRNA, to delete one or more exons encoding an lncRNA-coding regions, or to delete an entire coding sequence of the lncRNA in the genome of the cell; employing the cell as a donor cell and introducing the donor cell into a host embryo to form a donor cell-host embryo complex; and gestating the donor cell-host embryo complex in a suitable non-human animal under conditions suitable for gestation, wherein following gestation a progeny comprising the knockout of the lncRNA function is obtained. In one embodiment, the progeny is bred to homozygosity with respect to the knockout of the lncRNA function.

In one aspect, a method for making a non-human animal that comprises a knockout of a lncRNA function is provided, comprising modifying a genome of a somatic cell or a germ cell of a non-human animal cell to disrupt the transcription of the lncRNA, to delete one or more lncRNA-coding regions, or to delete an entire coding sequence of the lncRNA in the genome of the cell; employing the genome of the cell in an enucleated ovum to form a modified ovum; gestating the modified ovum in a suitable surrogate non-human animal under conditions suitable for gestation; and, obtaining a non-human animal progeny comprising the lncRNA knockout. In one embodiment, the progeny is bred to homozygosity with respect to the knockout of the lncRNA function.

In one embodiment, a method for making a non-human animal comprising a genetic modification in at least one lncRNA locus is provided. Such a method comprises contacting a pluripotent cell with a targeting construct comprising an insert nucleic acid flanked by 5' and 3' homology arms; wherein the targeting construct undergoes homologous recombination with the lincRNA locus in a genome of the cell to form a modified pluripotent cell; (b) introducing the modified pluripotent cell into a host embryo; and (c) gestating the host embryo in a surrogate mother, wherein the surrogate mother produces progeny comprising a modified lncRNA locus, wherein said genetic modification results in loss-of-function of the at least one lncRNA.

In one aspect, a method for modifying a lncRNA locus in a pluripotent cell is provided. Such a method comprises introducing into the pluripotent cell a targeting construct comprising an insert nucleic acid flanked with 5' and 3' homology arms that can undergo homologous recombination with the lncRNA locus; and identifying a modified pluripotent cell comprising a targeted genetic modification at the lncRNA locus, wherein the genetic modification results in loss-of-function of the lncRNA function. In one embodiment, the pluripotent cell is a human induced pluripotent (iPS) cell.

In various aspects and embodiments, modified cells include, for example, pluripotent cells, induced pluripotent cells, stem cells, embryonic stem cells, etc. In a specific embodiment, the cell is an embryonic stem (ES) cell. In a specific embodiment, the ES cell is a mouse or a rat ES cell.

In various aspects and embodiments, the non-human animals include, for example, ovine, bovine, porcine, and murine species of animals. In a specific embodiment, the animal is from a murine species, e.g., a mouse or a rat.

Other and further aspects and embodiments are included, as will be appreciated by those skilled in the art upon reading this disclosure.

Open boxes indicate noncoding exons. Red and green boxes on the Fendrr genomic locus and in the LacZ-neomycin resistance cassette are homologous sequences used for targeting.

Figure 2A:
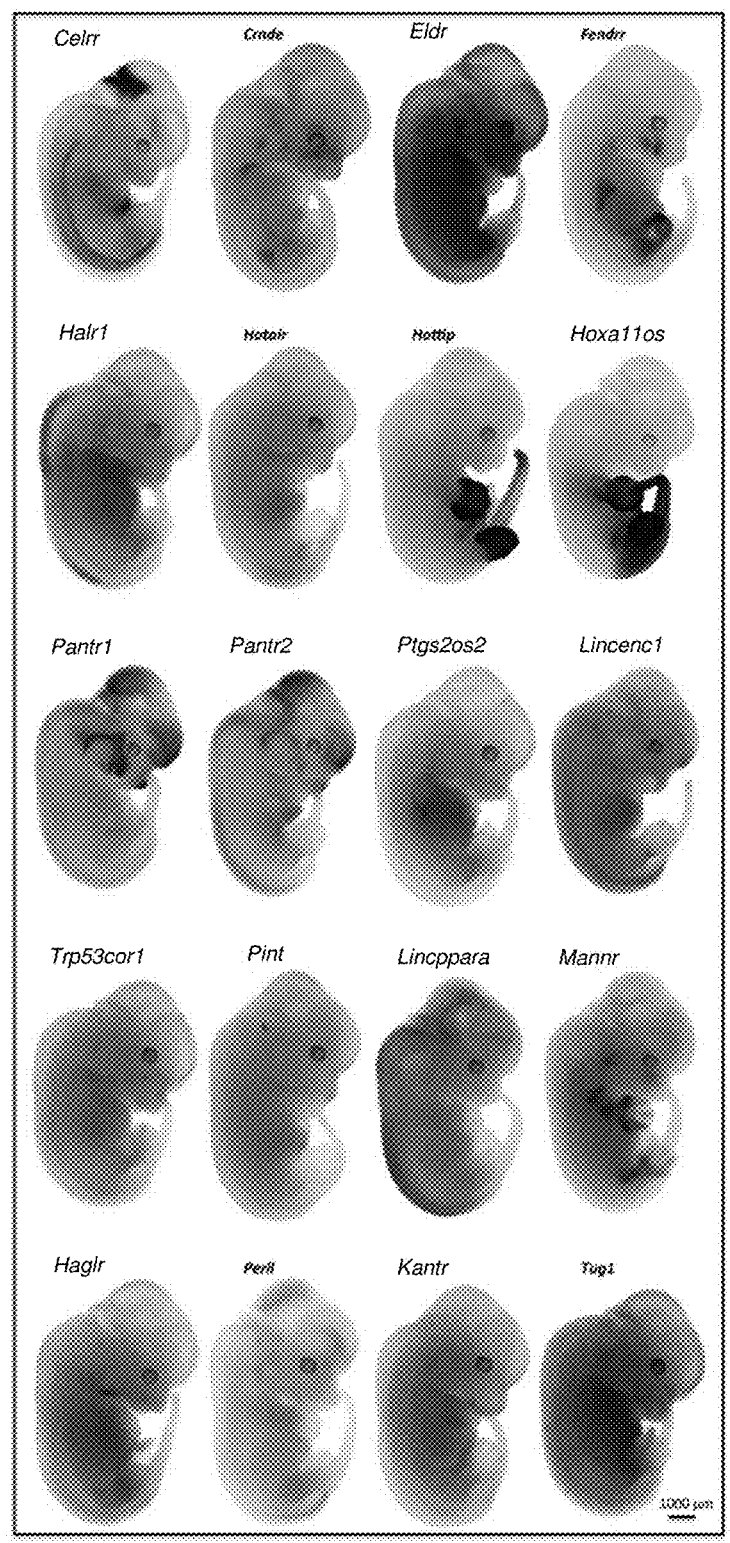
Figure 2B:
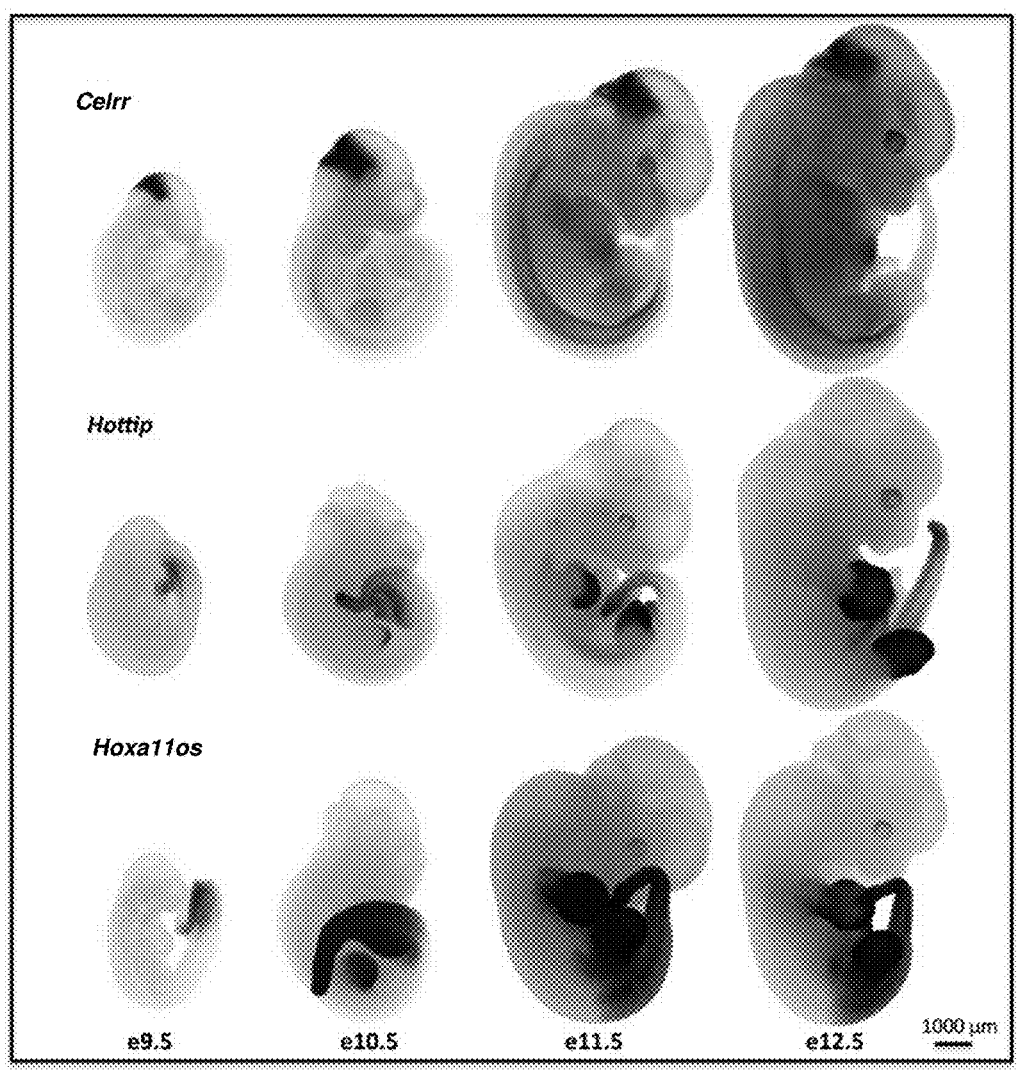

FIGS. 2A-2B illustrates spatial and temporal LacZ reporter gene expression in mid-gestation stage lincRNA targeted mouse embryos A, Heterozygous e12.5 embryo were fixed and stained for β-galactosidase showed a broad range of expression of the introduced LacZ reporter gene in the developing brain and craniofacial region (e.g., Pantr1 and Pantr2, Celrr and Haglr, see also FIG. 9), neural tube (Pantr2, Halr1 and lincppara), dorsal aorta (Celrr), heart (Celrr, Haglr, see also FIG. 9), lungs (Fendrr), limb buds (HOTTIP, Hoxa11os and Mannr), foregut (HOTTIP, Hoxa11os and Fendrr), posterior region and the tail (HOTAIR, HOTTIP and Hoxa11os). Similar analysis showed widespread lacZ expression pattern in Tug1, whereas expression of other reporter genes could be restricted to the epidermis (Eldr), mammary buds (Lincenc1, see also FIG. 9) or whisker placode (Trp53cor1, see also FIG. 9). Examples shown are representative of at least five genotype-confirmed embryos per lincRNA knockout project. B, Expression patterns in selected lincRNA (HOTTIP, Hoxa11os, and Celrr) F1 heterozygous embryos from the indicated stages (e9.5-e12.5) showed that expression began early at a restricted site and then extended beyond this initial site at later stages. Celrr expression was confined to the brain at e9.5 and progresses into the spinal cord by e12.5. Hoxa11os expression began in the developing tail bud and progresses into the entire caudal region of the embryo, hind limb and forelimb by e12.5. HOTTIP expression also began in the developing tail bud and was then observed in the developing distal autopods of the forelimb and hind limb by e11.5 and e12.5. Examples shown are representative of at least 5, genotype-confirmed embryos per lincRNA project.

Figure 3:
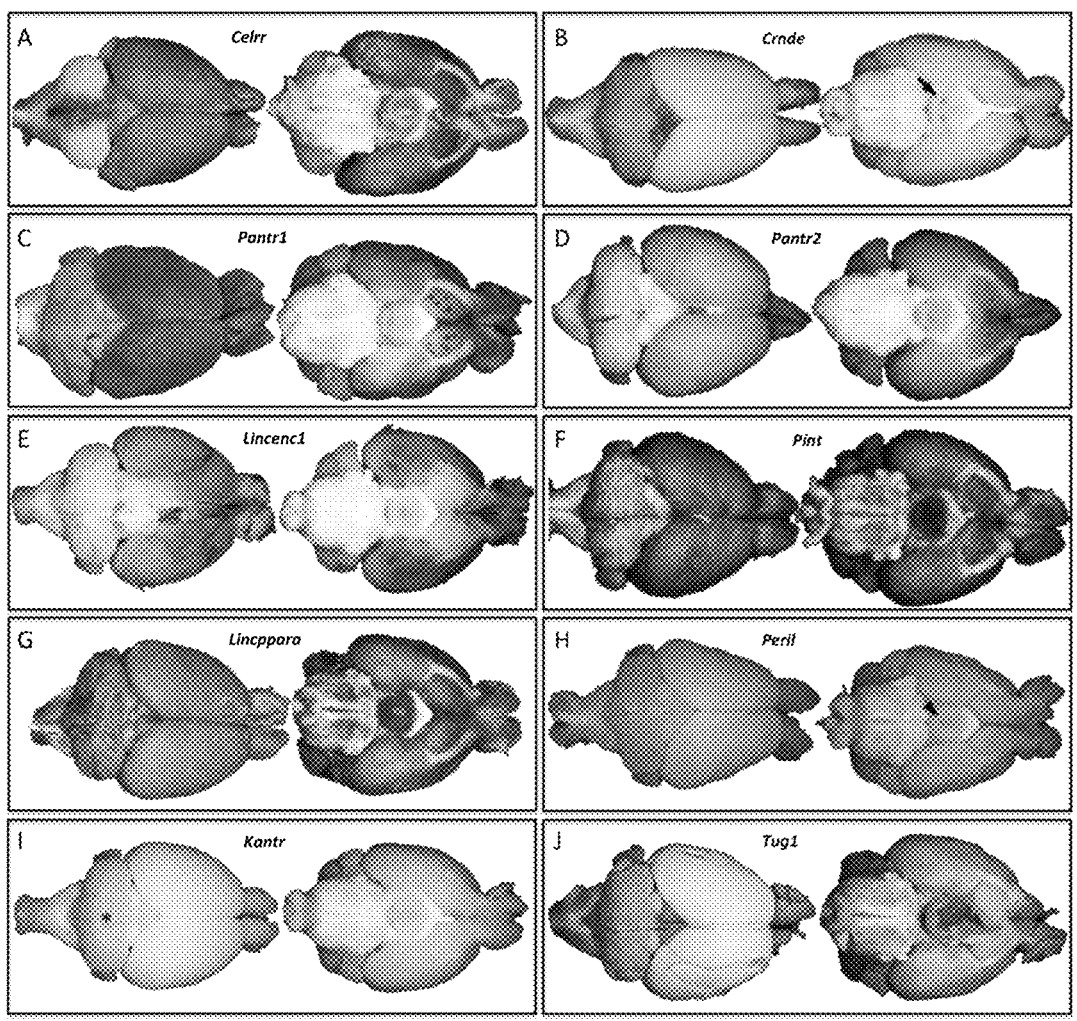

FIG. 3 illustrates LacZ reporter gene expression (blue) in brains of 6-8 week old lincRNA F0 generation heterozygotes. A, Celrr, broad expression in gray matter with the exception of the lateral cerebellum and ventral pons; B, Crnde, expression in the colliculi (dorsal view, arrow); C, Pantr1, expressed in the neocortex, olfactory bulb, basal forebrain, and hypothalamus; D, Pantr2, expressed in the neocortex, olfactory bulb, cerebellum, hypothalamus, and basal forebrain; E, Lincenc1, expressed in neocortex, parts of cerebellum, and medial hypothalamus with especially strong expression patterning in the olfactory projection and olfactory projection areas of temporal cortex (ventral view, red arrow); F, Pint, expressed ubiquitously in gray matter with especially intense expression in the hypothalamus; G, lincppara, broadly expressed in gray matter with especially dense expression in the hypothalamus; H, Peril, expression in the midline of the hypothalamus (ventral view, arrowhead); I, Kantr, potentially some expression in deep cerebellar layers (dorsal view, star); and J, Tug1, expression in spinal cord gray matter and light gray matter expression in most structures except for neocortex. n=2, genotype confirmed male mice per lincRNA knockout project.

Figure 4:
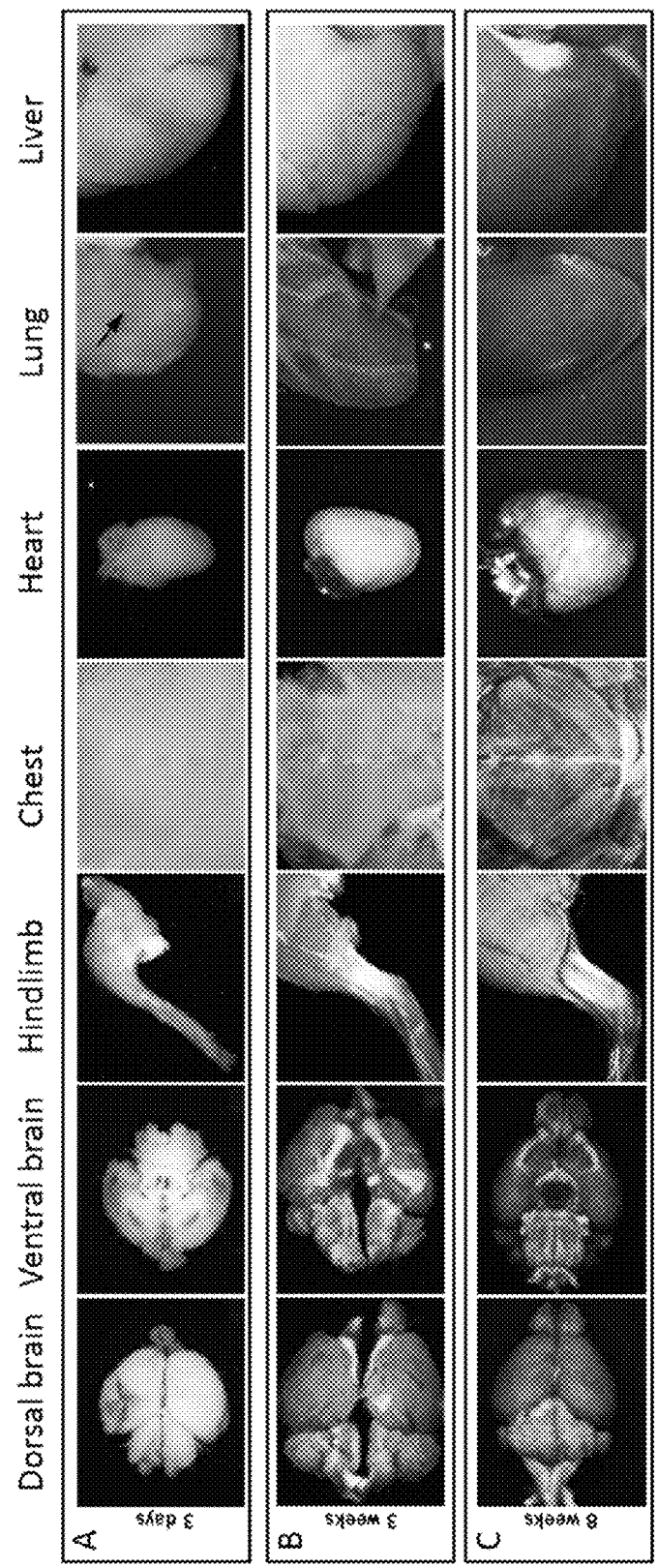

FIG. 4 illustrates that Pint exhibits increased expression from postnatal day 3 to 8 weeks of age. LacZ reporter gene expression (blue) at 3 days, 3 weeks, and 8 weeks in F0 heterozygotes show that Pint is increasingly expressed with age. A, at 3 days, β-galactosidase staining is only observed in portions of the brain, tendons and ligaments of the hind limb, and some bronchioles in the lung (arrow). B, at 3 weeks, there is increased staining in the brain, hind limb, atria of the heart, lung, and liver. C, by 8 weeks of age, the whole brain, skeletal muscle of the hind limb and chest, atria and myocardium, lung, and liver tissue all exhibit strong β-galactosidase staining representative of increased Pint expression. Examples shown are representative of n>4 mice per group.

Figure 5:
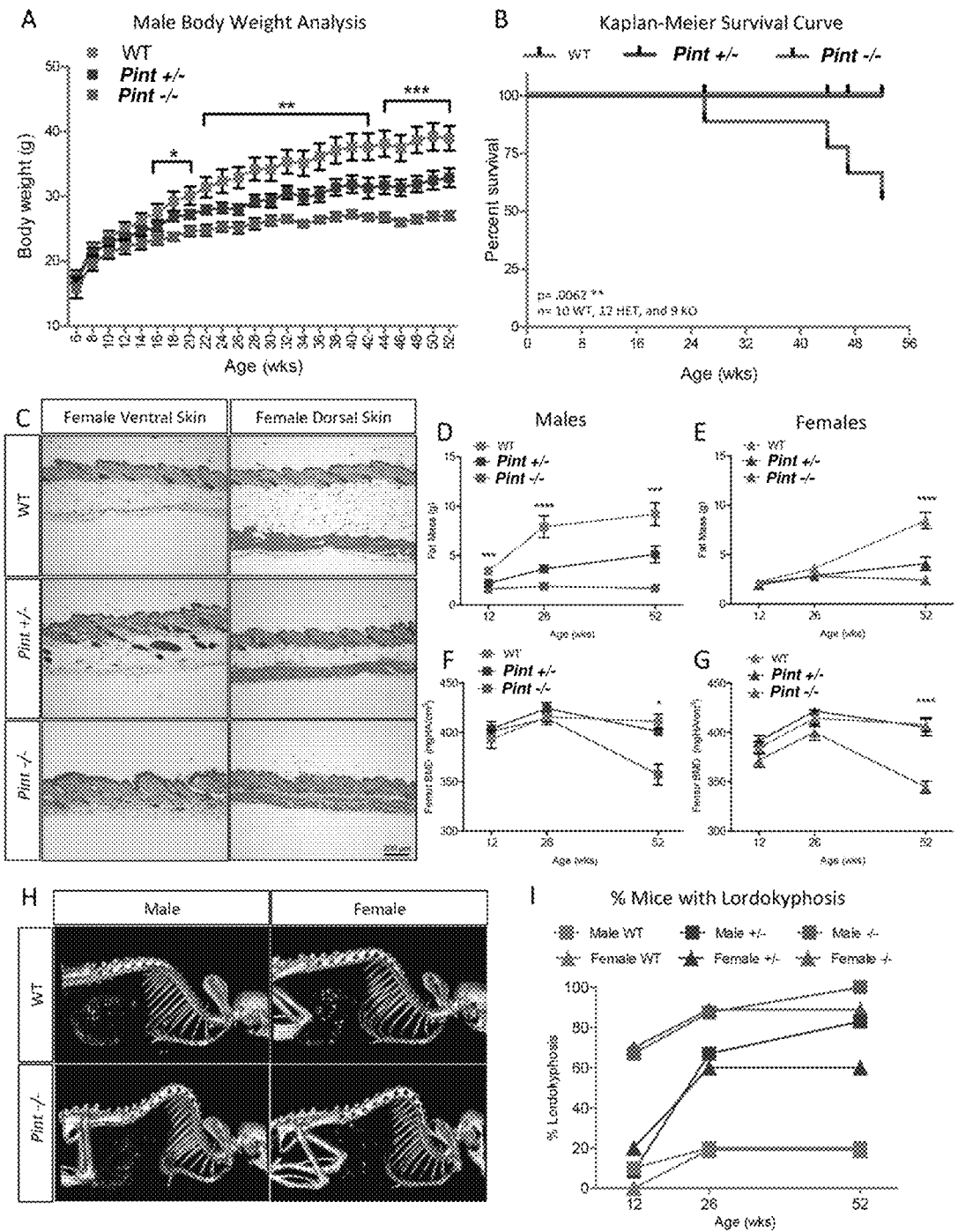

FIG. 5 illustrates premature aging-associated phenotype in Pint knockout mice. (A) $Pint^{-/-}$ and $Pint^{+/-}$ male mice exhibit a significantly slower growth rate than their wild type (WT) littermates and begin to show significant weight loss near 6 months of age. Data are plotted as the mean+/− SEM, n>9 mice for each group. Significance was assessed by a one-way ANOVA (*, $P<0.05$; , $P<0.005$; *, $P<0.001$). (B) Kaplan-Meier analysis of homozygous with heterozygous and WT mice. $Pint^{-/-}$ male mice exhibit a significant reduction in survival compare to $Pint^{+/-}$ and wild type littermates. Data are plotted as percent survival over 1 year observation. (C) Ventral and dorsal skin sections in $Pint^{-/-}$ mice compared with $Pint^{+/-}$ and WT littermates. (D, E, F, and G) MicroCT evaluation of body composition at 12-, 26- and 52-weeks of age. (D, E) Male $Pint^{-/-}$ and $Pint^{+/-}$ mice exhibit a significant reduction in body fat as early as 26-week of age. Female $Pint^{-/-}$ mice have reduced body fat at an older age noticeably at 52-week of age (***, $P<0.001$, one-way ANOVA). (F, G) A significant reduction in femur bone mineral density (BMD) observed in both males and females $Pint^{-/-}$ compared with their $Pint^{+/-}$ and WT littermates (*, $P<0.05$; ***, $P<0.001$, one-way ANOVA). (H) MicroCT images depict pronounced lordokyphosis (curvature of the spinal column) seen in older male and female $Pint^{-/-}$ mice compared with WT littermates. (I) Approximately 70% of male and female $Pint^{-/-}$ mice have lordokyphosis by 12 weeks of age, compared with 0-20% of $Pint^{+/-}$ and WT littermates. By 26 weeks of age the proportion of $Pint^{-/-}$ mice with lordokyphosis increased to nearly 90% and appeared in approximately 60% of $Pint^{+/-}$ mice, compared with less than 20% of WT littermates. n>9 mice per group for all observations reported.

Figure 6:
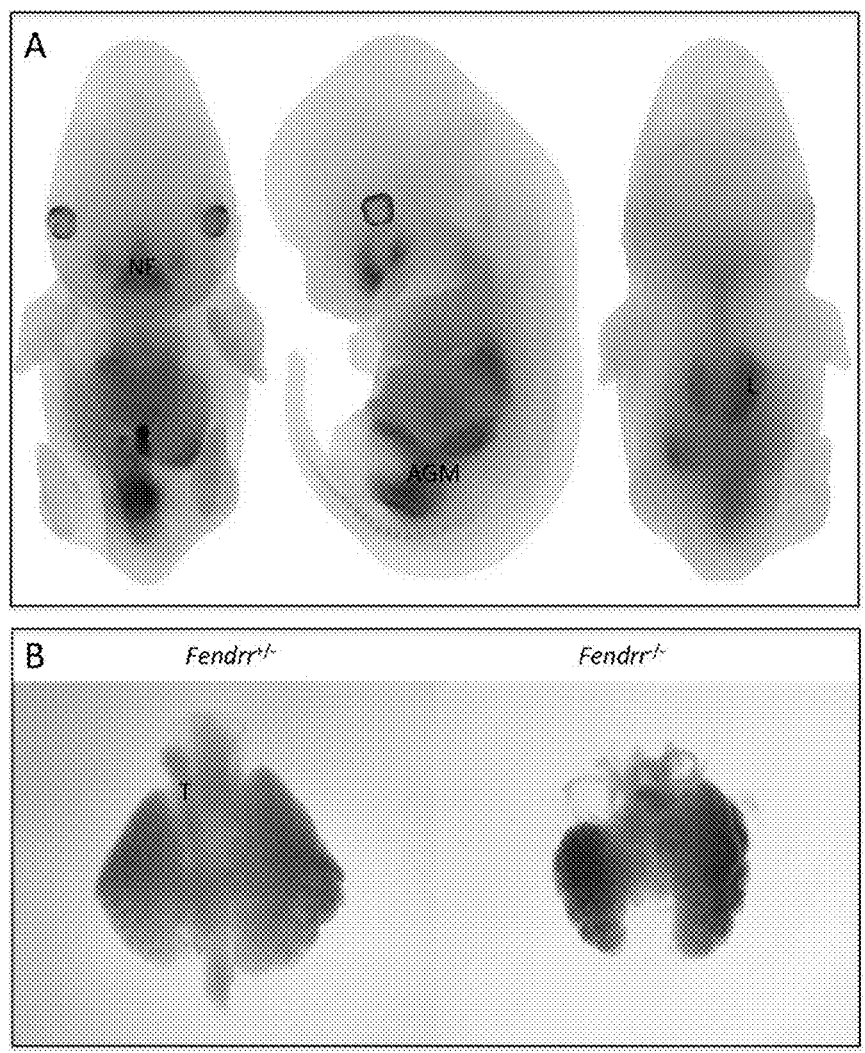

FIG. 6 illustrates that Fendrr knockout mice exhibited abnormal lung morphology at e13.5. A. LacZ reporter gene expression at e12.5 in Fendrr KO embryos exhibits positive expression in the frontal nasal region (FN) of the face, the aorta gonad mesonephros (AGM) region, and the respiratory tract including the lungs (L) and trachea (T). B. Dissection of lungs at e13.5 revealed an abnormal, disorganized, globular phenotype in the lobes of the KO in comparison to the Het.

Figure 7:
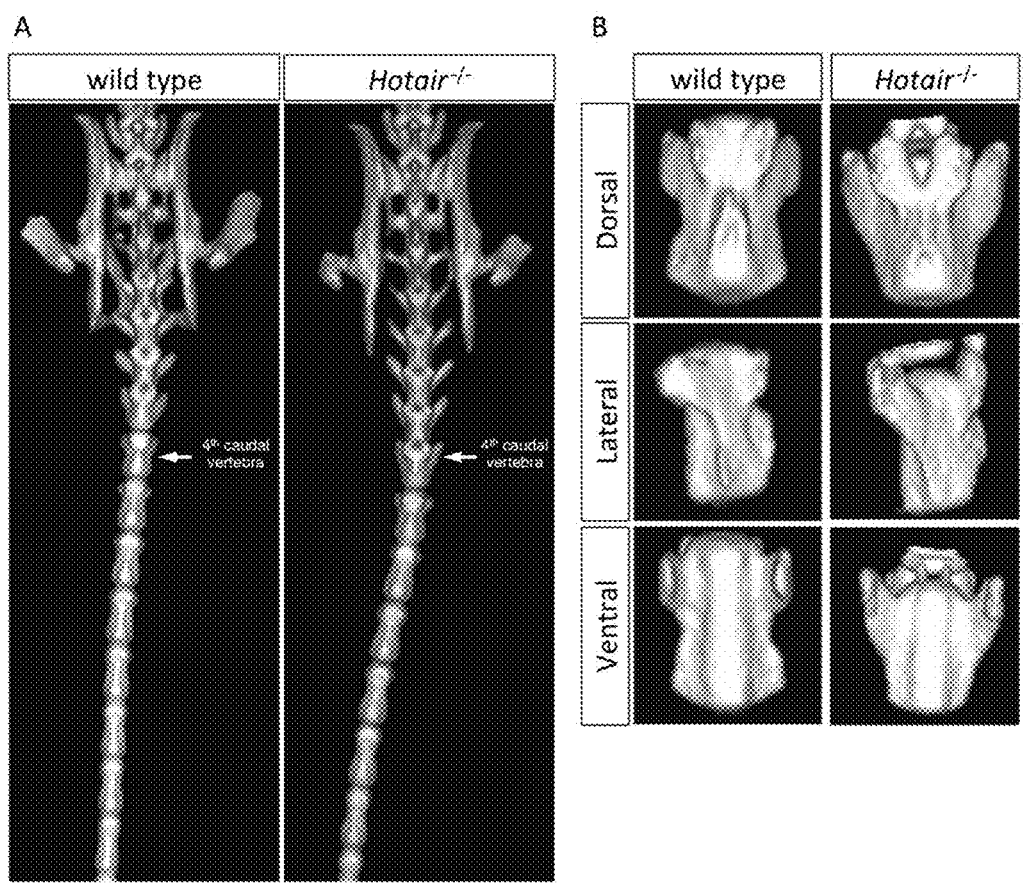

FIG. 7 illustrates homeotic transformation observed in the $4^{th}$ caudal vertebra of HOTAIR KO mice. A. Visualization of the sacral and caudal region of the mouse skeleton by μCT reveals a homeotic transformation of the $4^{th}$ caudal vertebra to a structure similar to that of the $3^{rd}$ caudal vertebra in HOTAIR KO mice. B. Dorsal, lateral and ventral comparison of WT and HOTAIR KO $4^{th}$ caudal vertebra reveals a structural abnormality in KO indicative of a homeotic transformation.

Figure 8:
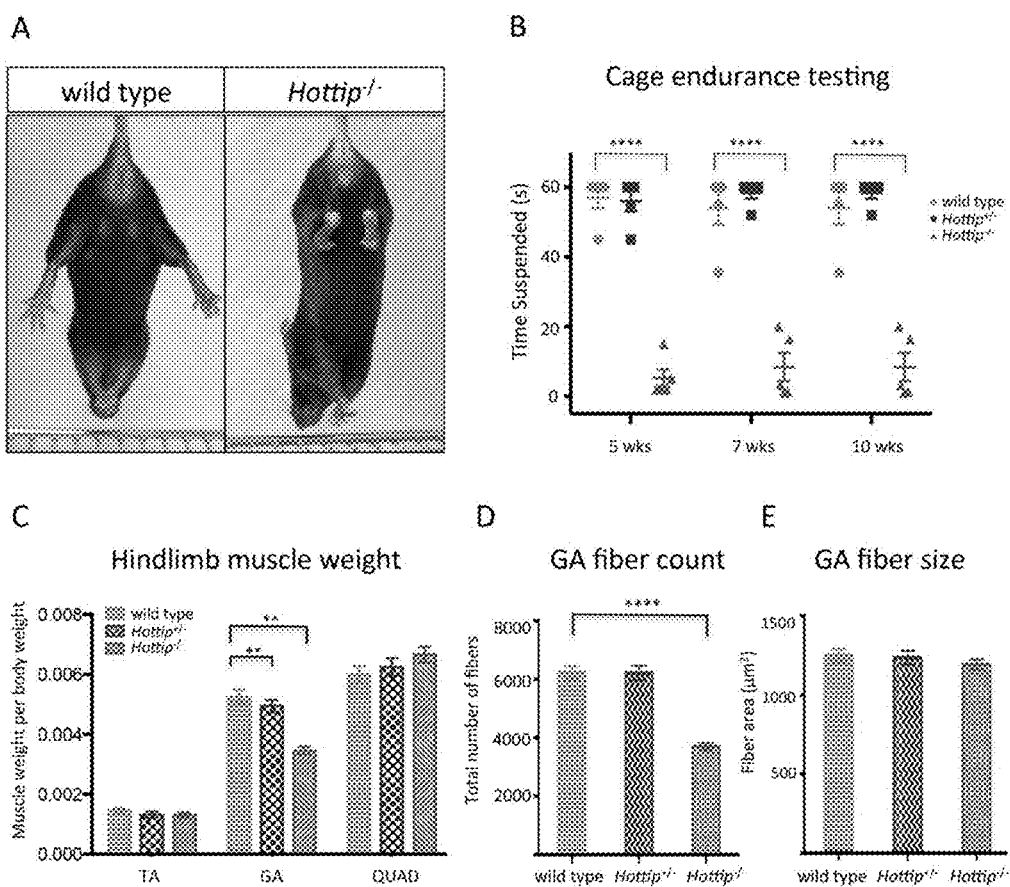

FIG. 8 illustrates that HOTTIP KO mice showed abnormal hindlimb posture, reduced grip strength in fore- and hindlimbs and a muscle wasting phenotype. A. HOTTIP KO mice demonstrated unusual "clasping" posture of the hindlimbs when suspended by the tail. WT, wild type; KO, knockout. B. Cage endurance testing revealed that HOTTIP KO mice have a reduced ability to remain suspended from an inverted wire cage top. n=5 mice for each group. C. The right and left TA (tibialis anterior), GA (gastrocnemius) and Quad (quadriceps) muscles were taken from WT, Het and KO mice and weighed. Muscle weights are normalized to body weight and calculated to include both right/left muscle weights. Data are means+/−SEM, n=6 mice for each group.

A significant decrease in muscle weight was observed only in the GA of HOTTIP KO animal in both males and females (male data not shown). Asterisks indicate a significant difference in the KO GA muscle weights compared to all other control groups (P<0.01). D. Comparison of GA muscle fiber numbers in WT, Het and KO. A significant reduction of fiber count was observed in the KO. Significance assessed by using the one-way ANOVA (P<0.0001). E. Comparison of mean cross-sectional area of muscle fibers. Cross sections taken from the GA muscle were stained with an antibody against laminin (Sigma) and measured. There is no noticeable size difference between KO and control skeletal muscles. n=6 mice per group for all muscle analyses.

Figure 9:
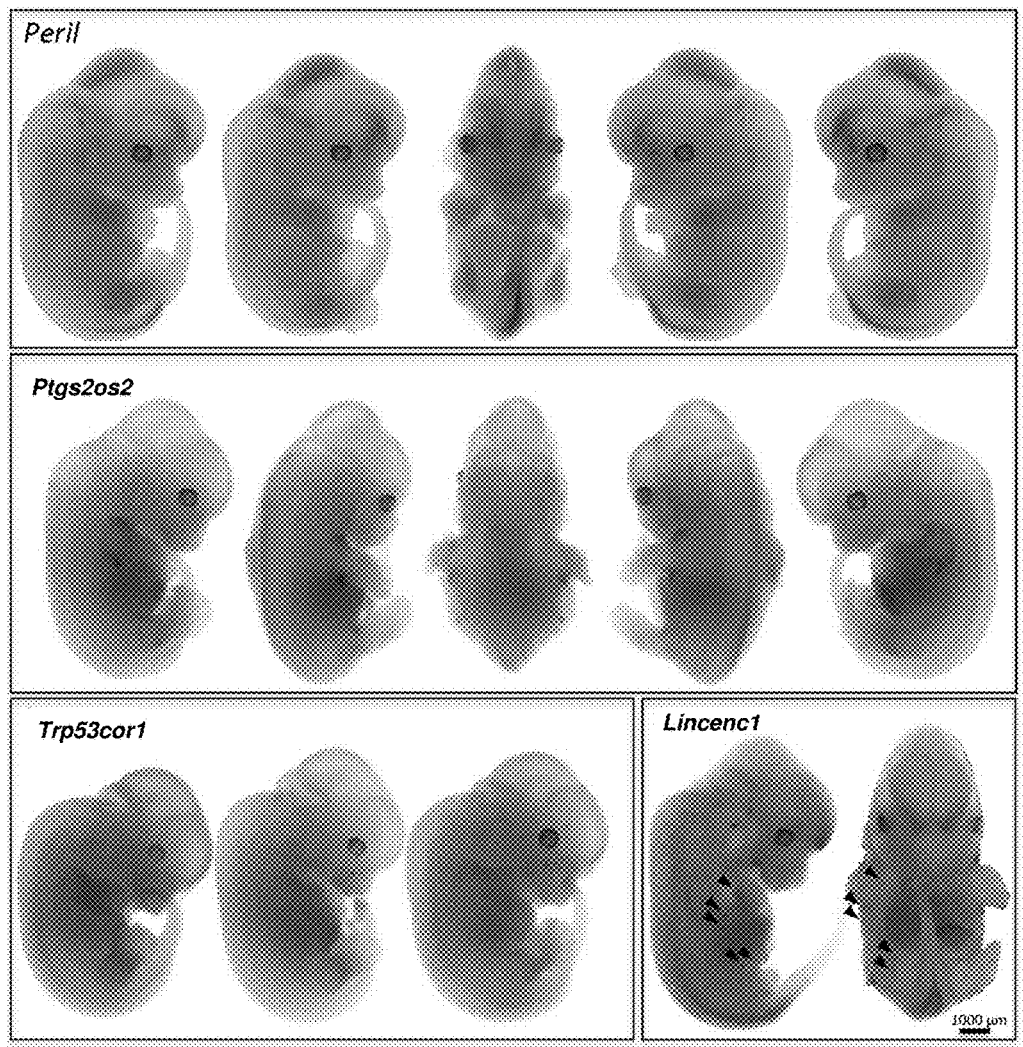

FIG. 9 illustrates precise staining in small areas for four lincRNA knockouts exhibiting highly specific staining patterns: Specific Mid-Gestational lacZ Expression Profiles for Peril, Ptgs2os2, Trp53cor1 and Lincenc1 (A) LacZ reporter profiling for Peril shows a specific neuronal expression pattern as well as strong expression in the heart and posterior tail region. (B) Ptgs2os2 lacZ reporter expression is restricted to the base of developing forelimbs and hindlimbs. (C) Trp53cor1 lacZ reporter expression is specific to the developing whisker placode in the nasal process. E12.5 embryos collected from the same litter capture the progression of whisker placode development over a short period of time. (D) Forelimbs and hindlimbs were removed in the Lincenc1$^{+/-}$ embryos to reveal mammary bud expression (arrowheads). Ventral view of E12.5 Lincenc1$^{+/-}$ embryo: lacZ expression is detected in five pairs of mammary buds.

Figure 10:
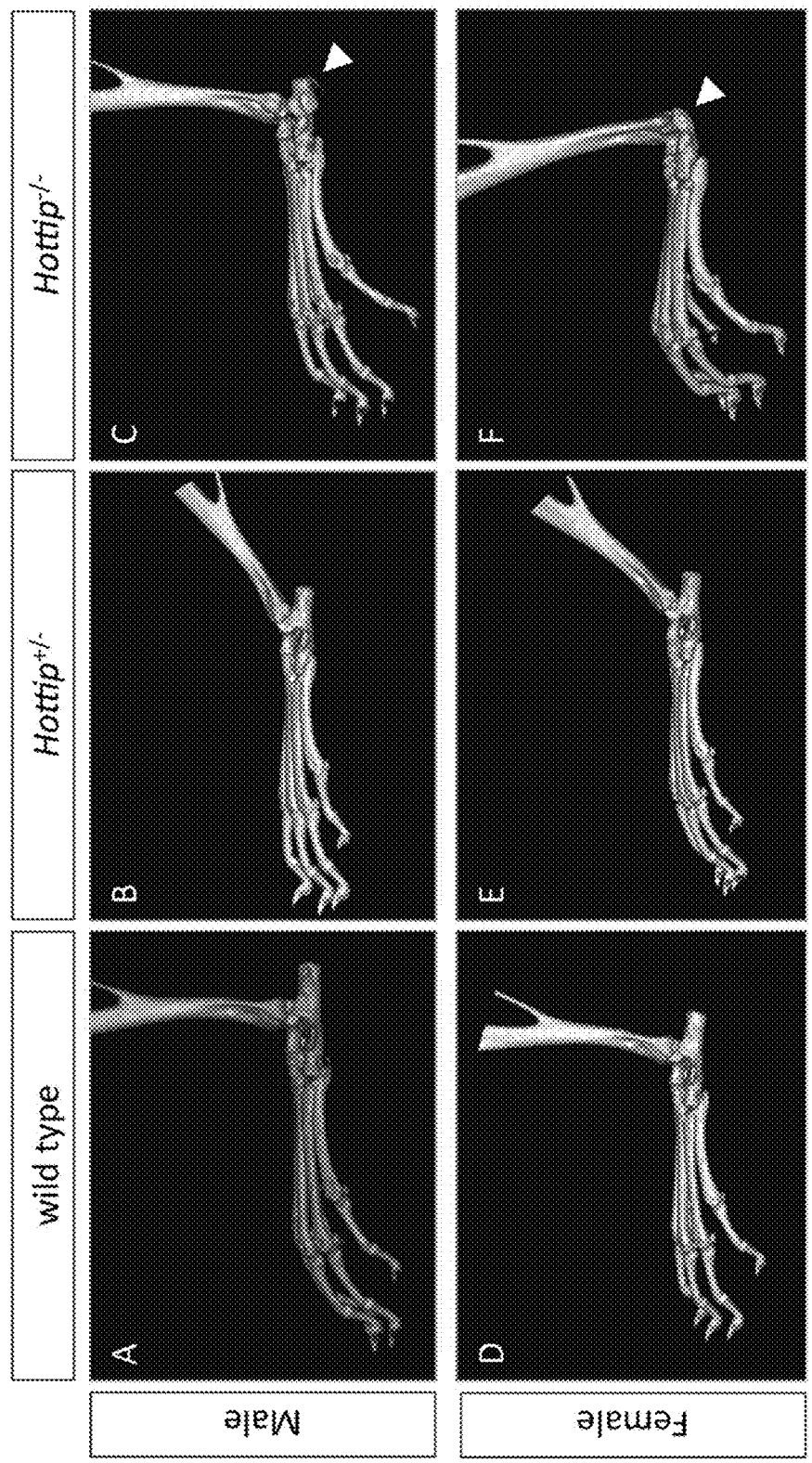

FIG. 10 illustrates a phenotype characterized by loss of heel bone in HOTTIP knockouts: Skeletal Malformations Observed in Hottip Mutant Mice. In addition to a skeletal muscle phenotype in the hindlimb, Hottip$^{-/-}$ mice also display a skeletal bone abnormality visualized by 3D microCT. Both male and female (C and F) Hottip$^{-/-}$ mice have shortened calcanea (arrows) in comparison to (A and D) WT and (B and E) Hottip$^{+/-}$ littermate controls.

FIG. 11 represents a table (Table 2) of reporter expression in embryo and adult tissue for the lncRNA knockouts of the study.

DETAILED DESCRIPTION OF THE INVENTION

Glossary

The term "embryonic stem cell" or "ES cell" includes an embryo-derived totipotent or pluripotent cell that is capable of contributing to any tissue of the developing embryo upon introduction into an embryo. The term "pluripotent cell" includes an undifferentiated cell that possesses the ability to develop into more than one differentiated cell types.

The term "large targeting vector" or "LTVEC" includes large targeting vectors for eukaryotic cells that are derived from fragments of cloned genomic DNA larger than those typically used by other approaches intended to perform homologous gene targeting in eukaryotic cells. Examples of LTVEC, include, but are not limited to, bacterial homologous chromosome (BAC) and yeast artificial chromosome (YAC).

The term "recombination site" includes a nucleotide sequence that is recognized by a site-specific recombinase and that can serve as a substrate for a recombination event.

The term "site-specific recombinase" includes a group of enzymes that can facilitate recombination between "recombination sites". Examples of "site-specific recombinase" include, but are not limited to, Cre, Flp, and Dre recombinases.

The term "germline" in reference to a nucleic acid sequence includes a nucleic acid sequence that can be passed to progeny.

The phrase "operably linked" means components are linked to function together in their intended manner. In one instance, a nucleic acid sequence encoding a protein may be operably linked to regulatory sequences (e.g., promoter, enhancer, silencer sequence, etc.) so as to retain proper transcriptional regulation.

The term "long non-coding RNA" or "lncRNA" as used herein includes a non-protein coding transcript longer than 200 nucleotides.

The term "long intergenic non-coding RNA" or "lincRNA" as used herein includes a subgroup of lncRNAs. As used herein, lincRNAs do not overlap with exons of protein-coding regions of the genome.

The term "locus" is defined as a segment of DNA within the genomic DNA. For example, a lncRNA locus is a segment of DNA within the genomic DNA that encodes a lncRNA.

I. Compositions Comprising Genetic Modification of at Least One lncRNA Locus

Non-human animals, cells, tissues, and embryos are provided that comprise lncRNA loss-of-function, including but not limited to disruptions or knockouts of one or more lncRNAs. Methods and compositions for manipulating lncRNA expression are provided. Targeting compositions directed to modifying or knocking out lncRNAs are also provided. Non-human animals, cells, and tissues are provided that exhibit a phenotype associated with non-function of one or more lncRNAs. Although the following description is with reference to a survey of certain particular lncRNAs, the methods and compositions may be practiced with any lncRNA.

Provided herein are non-human animals, cells, tissues and embryos comprising a targeted genetic modification in at least one long non-coding RNA (lncRNA) locus. In such cases, the modified lncRNA locus comprises a loss of function mutation in a nucleic acid sequence that encodes the lncRNA. Also provided are cells, tissues and embryos derived from the non-human animals comprising a loss-of-function mutation of at least one lncRNA.

The term, "loss-of-function" as it relates to a lncRNA can include any modification in a lncRNA locus that results in a decrease or lack of expression of the lncRNA and/or a decrease or lack of activity/function of the lncRNA. The expression level of a lncRNA may be measured directly, for example, by assaying for the level of the lncRNA in the cell or organism.

In general, the expression level and/or activity of the lncRNA is decreased if the lncRNA expression level and/or the activity level of the lncRNA is statistically lower (p≤0.05) than the lncRNA level in an appropriate control cell or organism that has not been genetically modified or mutagenized to inhibit the expression and/or activity of the lncRNA. In specific embodiments, the concentration and/or activity of the lncRNA is decreased by at least 1%, 5%, 10%, 20%, 30%, 40%, 50%, 60%, 70%, 80%, 90%, 95%, 99% or more relative to a control cell or organism which has not been modified to have the decreased level and/or activity of the lncRNA.

In other instances, cells or organisms having the targeted genetic modification that reduces the expression level and/or activity of the lncRNA are selected using methods that include, but are not limited to, Southern blot analysis, DNA sequencing, PCR analysis, or phenotypic analysis. Such cells or organisms are then employed in the various methods and compositions described herein.

A "subject cell" or "subject organism" is one in which a genetic alteration, such as a genetic modification disclosed herein has been effected, or is a cell/organism which is descended from a cell/organism so altered and which comprises the alteration. A "control" or "control cell" or "control organism" provides a reference point for measuring changes in phenotype of the subject cell or organism. In one embodiment, a control cell/organism is as closely matched as possible with the cell/organism with the genetic modification in the lncRNA except it lacks the genetic modification or mutation resulting in the reduced expression and/or activity (for example, the respective cells can originate from the same cell line). In other instances, the control cell/organism may comprise, for example: (a) a wild-type cell/organism, i.e., of the same genotype as the starting material for the genetic alteration which resulted in the subject cell/organism; (b) a cell/organism of the same genotype as the starting material but which has been genetically modified with a null construct (i.e. with a construct which has no known effect on the trait of interest, such as a construct comprising a marker gene); (c) a cell/organism which is a non-genetically modified progeny of a subject cell/organism (i.e., the control cell and the subject cell originate from the same cell line); (d) a cell/organism genetically identical to the subject cell/organism but which is not exposed to conditions or stimuli that would induce expression of the gene of interest; or (e) the subject cell/organism itself, under conditions in which the genetic modification does not result in an alteration in expression of the polynucleotide of interest.

The term "animal," in reference to animals, cells, tissues or embryos, includes mammals, fishes, and birds. Mammals include, e.g., humans, non-human primates, monkey, ape, cat, dog, horse, bull, deer, bison, sheep, rodents (e.g., mice, rats, hamsters, guinea pigs), livestock (e.g., bovine species, e.g., cows, steer, etc.; ovine species, e.g., sheep, goats, etc.; and porcine species, e.g., pigs and boars). Birds include, e.g., chickens, turkeys, ostrich, geese, ducks, etc. Domesticated animals and agricultural animals are also included. The phrase "non-human animal," in reference to animals, cells, tissues or embryos, excludes humans.

In one embodiment the animal is a non-human animal. In another embodiment, the non-human animal is a mammal. In another embodiment, the mammal is a rodent. In a further embodiment, the rodent is a mouse, a rat or a hamster.

Genetic modifications as described herein can include one or more deletions from a lncRNA locus of interest, additions to a lncRNA locus of interest, replacement of a lncRNA locus of interest, and/or any combination thereof. The locus of interest can comprise coding regions or non-coding regulatory regions.

The genetic modifications provided herein are targeted to a lncRNA locus of interest. A loss-of-function of a lncRNA can result from a targeted genetic modification in the lncRNA gene (i.e., a genetic modification in a regulatory region, the coding region, exons, and/or introns etc.). Such targeted modifications include, but are not limited to, additions of one or more nucleotides, deletions of one or more nucleotides, substitutions of one or more nucleotides, a disruption of the lncRNA locus, a knockout of the lncRNA locus or a portion thereof, a knock-in of the lncRNA locus or a portion thereof, a replacement of an endogenous lncRNA nucleic acid sequence or a portion thereof with a heterologous nucleic acid sequence, or a combination thereof. In specific embodiments, at least 1, 2, 3, 4, 5, 7, 8, 9, 10, 50, 100, 400 or more nucleotides are changed to form the targeted genomic modification.

In one embodiment, the loss-of-function mutation is characterized by a disruption or a knockout of at least one lncRNA function.

The lncRNA locus can be genetically modified in any region of the locus such that the modification results in loss-of-function of the lncRNA. In one embodiment, the modification of the lncRNA locus comprises a deletion of the entire lncRNA coding region or a portion thereof. In one embodiment, the modified lncRNA locus comprises a deletion of one or more exons that encode the lncRNA or a portion thereof. In another embodiment, the deletion comprises a deletion of one or more exons within the lncRNA locus starting in a first exon of the lncRNA locus. In other embodiments, the deletion comprises a deletion of one or more exons within the lncRNA locus starting in a second exon of the lncRNA locus.

In some cases, the lncRNA locus or a portion thereof is replaced with an insert nucleic acid. In such cases, the replacement can be a replacement of the entire RNA coding region of the lncRNA locus or a portion thereof with the insert nucleic acid, a replacement of one or more exons of the lncRNA locus with the insert nucleic acid, a replacement of one or more exons within the lncRNA locus starting in the first exon of the lncRNA locus with the insert nucleic acid or a replacement of one or more exons within the lncRNA locus starting in the second exon with the insert nucleic acid.

In some instances, the insert nucleic acid is positioned in the lncRNA locus such that it is in operable linkage with an endogenous lncRNA promoter such that the endogenous lncRNA promoter drives expression of the insert nucleic acid. In such cases, the expression of the nucleic acid sequence follows an expression pattern of the lncRNA.

In one embodiment, the lncRNA locus or portion thereof is replaced with an insert nucleic acid comprising a first nucleic acid sequence that encodes a reporter. For example, in the case where the insert nucleic acid comprises a reporter gene and is placed into the lncRNA locus in operable linkage to the lncRNA promoter, the expression of the reporter gene is driven by the endogenous lncRNA promoter. Alternatively, the insert nucleic acid is not inserted in operable linkage with the endogenous lncRNA promoter. In such cases, the insert nucleic acid can comprise a promoter. In one embodiment, the insert nucleic acid comprises a reporter gene operably linked to a promoter that drives expression of the reporter gene.

In one embodiment, the lncRNA locus or portion thereof is replaced with an insert nucleic acid comprising a second nucleic acid sequence that encodes a selectable marker. In such cases, the second nucleic acid sequence is operably linked to a promoter that drives expression of the selectable marker.

In another embodiment, the lncRNA locus or portion thereof is replaced with an insert nucleic acid comprising a reporter gene and a selectable marker gene. In such cases, the reporter gene and/or the selectable marker gene may or may not be operably linked to a promoter.

Various promoters that can be employed in the methods and compositions are provided elsewhere herein.

Such genetic modifications (including those that result in a decrease or a modulation in expression and/or activity of the target lncRNA) are also capable of being transmitted through the germline. In specific embodiments, the genetic modifications result in a knockout of the desired target locus.

Such non-human animals, for example, find use in in a variety of experimental systems as discussed elsewhere herein.

For example, lncRNA knockouts offer an animal model to study lncRNA function, the role of lncRNA in development, and the role of lncRNA in various cellular pathways and diseases, including, but not limited to, aging, including premature aging, brain development, embryonic development, lung development, skeletal development, muscle development, cancer or regulation of transcription.

Various methods can be used to generate the targeted genetic modification and are described elsewhere herein.

A. lncRNA

The non-human animals, cells, tissues, and embryos employed in the methods and compositions provided herein have a genetic modification that results in the loss-of-function of at least one lncRNA. lncRNAs are long non-coding RNAs of greater than 200 nucleotides. A subgroup of lncRNA, long intergenic non-coding RNA (lincRNA) are intergenic and do not overlap with protein coding regions.

Any lncRNA locus can be modified in the methods and compositions provided herein. In one embodiment, the genetically modified non-human animal, cell, tissue or embryo comprises a genetic modification in a lncRNA. In another embodiment, the lncRNA is a lincRNA.

Non-limiting examples of an lncRNA comprise HOTAIR, HOTTIP, Hoxa11os (formerly named HoxA11as), Pantr1 (formerly named lincRNA-Brn1-a), Pantr2 (formerly named lincRNA-Brn1-b), Ptgs2os2 (formerly named lincRNA-Cox2), Eldr (formerly named Fabl and lincRNA-Egfr), lincenc1 (formerly named lincRNA-Enc1), Mannr (formerly named lincRNA-Evi1), Fendrr (formerly named lincRNA-Foxf1), Halr1 (formerly named Haunt and lincRNA-HoxA1), Haglr (formerly named Mdgt and lincRNA-HoxD3), Celrr (formerly named Celr and lincRNA-Insig2), Crnde (formerly named lincRNA-Irx5), Kantr (formerly named Spasm and lincRNA-Jarid1c), Pint (formerly named linc-Pint and lincRNA-Mkln1), Trp53cor1 (formerly named lincRNA-p21), lincppara (formerly named lincRNA-Ppara), Peril (formerly named lincRNA-Sox2), Tug1 (formerly named lincRNA-Tug1), or a combination thereof.

It is now clear that protein-coding genes are not all there is to the genome (Mattick, J. S. (2009), *PLoS Genet* 5:e1000459). Large-scale whole genome expression studies in mammalian cells have revealed that approximately three-quarters of the genome is capable of being expressed as RNA (Carninci, P., et al. (2005), *Science* 309:1559-1563; Djebali, S., et al. (2012), *Nature* 489:101-108; Kapranov, P., et al. (2007), *Science* 316:1484-1488), and most of the transcripts do not code for proteins. Among the non-coding transcripts is a diverse class known as long non-coding RNAs (lncRNAs). Representing approximately 15,000 transcripts from nearly 10,000 genomic loci in human cells (Derrien, T., et al. (2012), *Genome Res* 22:1775-1789), lncRNAs and a subclass known as large intergenic non-coding RNAs (lincRNAs) (Guttman, M., et al. (2009), *Nature* 458:223-227; Khalil et al. (2009)) resemble protein-coding mRNAs in structure, synthesis, and the chromatin character of their genes. Whether or not this structural similarity extends to a functional diversity that matches proteins remains an open question.

Functional studies on individual lncRNAs have identified roles in X chromosome inactivation (Marahrens, Y., et al. (1997), *Genes Dev* 11:156-166), imprinting (Leighton, P. A., et al. (1995), *Nature* 375:34-39; Mohammad, F., et al. (2010), *Development* 137:2493-2499; Sleutels, F., et al. (2002), *Nature* 415:810-813; Takahashi, N., et al. (2009), *Hum Mol Genet* 18:1879-1888), retinal differentiation (Young, T. L., et al. (2005), *Curr Biol* 15:501-512), and heart and body wall development (Grote, P., et al. (2013), *Dev Cell* 24:206-214). Studies on the lincRNA HOTAIR first revealed that lincRNAs could regulate gene expression at sites far from their own sites of transcription by guiding chromatin modifying complexes (polycomb repressive complex 2 in the case of HOTAIR) to specific genomic loci (Rinn, J. L., et al. (2007), *Cell* 129:1311-1323). Similar mechanisms of action have been found for the Xist lncRNA in X chromosome inactivation (Zhao, J., et al. (2008), *Science* 322:750-756) and for the AIR and Kcnq1ot1 lncRNAs in imprinting. These findings suggest a broader role for lncRNAs in the regulation of gene expression, which has been supported by analysis of correlated expression patterns for lincRNA and protein-coding genes that point to the participation of lincRNAs in a wide-ranging array of cellular processes and organ system physiology (Guttman et al. (2009)). Many of the recent studies on lncRNAs have employed global genomic strategies that have established an overall picture of the role of lncRNAs as a class. To answer the questions of whether the actions of lncRNAs on protein gene expression are broad, subtle, and buffering or specific, direct, and determinative requires the investigation of their individual roles in live animals.

Provided herein in the following description are non-limiting examples of genetic modifications resulting in knockout of various lncRNAs in a mouse knockout model. A survey of gene expression and phenotypes in knockout mice for 20 lincRNA genes was conducted, which included LacZ profiling that showed diverse spatiotemporal patterns of tissue-specific expression; revealed two knockout lines that exhibited perinatal lethality; and, revealed other phenotypes include premature aging-associated phenotype and defects in lung, skeleton, brain and muscle.

To begin to examine the functions of the lncRNAs in a live animal setting, knockout mouse lines were created for twenty lincRNA genes. Each mutant allele carried a lacZ reporter whose expression profiling revealed a wide spectrum of spatiotemporal and tissue-specific transcription patterns in adults and embryos. Among 18 homozygous knockout lines, six (about 33%) exhibited discernable mutant phenotypes, two (11%) of which were perinatal lethal, and included premature aging-associated phenotype, aberrant morphology in the brain, lungs, skeleton, and muscle and global changes in gene expression patterns that together point to diverse roles for this new class of functional RNAs in embryonic development and in the physiology of a broad array of tissues and organs.

B. Genetic Modification of a lncRNA Locus

Provided herein are methods and compositions for the genetic modification of at least one lncRNA locus in a non-human animal, cell, tissue or embryo.

The genetic modification of the lncRNA locus of interest can be any modification of the locus as described in detail elsewhere herein (i.e. deletion, insertion, replacement, etc.). In such cases the genetic modification results in loss-of-function of the lncRNA. In one embodiment, the genetic modification comprises a disruption or a knockout of at least one lncRNA.

i. Knockout Allele Design and Construction

The design and construction of a modified lncRNA allele, such as a knockout, is complicated by several technical issues. For example, there is a general lack of structure-function relationships for lncRNAs and a lncRNA locus does not have an open reading frame. Therefore, the same strategies that would guide design of an allele for modifying a protein coding sequence, such as a knockout, may not be applicable to lncRNA. In addition, the boundaries of the lncRNA genes are not well defined which further complicates design of a modified lncRNA allele, such as a knockout. Non-limiting examples of these technical difficulties and the strategies used herein to successfully overcome these hurdles in lncRNA knockout design are described in detail herein below.

In one example, the methods and compositions provided herein were applied to mouse as a model system. However, even though the following description is with reference to mice, any non-human animal, cell, tissue or embryo can be used in the methods and compositions described herein.

Since its invention nearly twenty-five years ago, the method for creating genetically modified, so-called knockout, mice has established the mouse as the premier system for the study of mammalian gene function (Capecchi, M. R. (2001), *Nat Med* 7:1086-1090; Evans, M. J. (2001), *Nat Med* 7:1081-1083; Smithies, O. (2001), *Nat Med* 7:1083-1086). With few exceptions, the application of knockout mouse technology in both individual gene studies as well as large-scale international projects (Bradley, A., et al. (2012), *Mamm Genome* 23:580-586) has focused on protein-coding genes, but the recent efforts to create global knockout mouse resources for microRNAs (Prosser, H. M., et al. (2011), *Nat Biotechnol* 29:840-845) (mcmanuslab.ucsf.edu/microrna_knockout) demonstrate the value of applying the technology to non-coding RNAs.

Applying knockout mouse technology to lncRNAs does, however, present some technical questions and difficulties. Most proteins have elements or domains that are known or at least predicted to be important for function. Deleting the coding sequences for these essential parts is often sufficient to create a null allele. Likewise, conditional alleles can be designed that isolate the critical exon or exons for later deletion by the action of a tissue specific recombinase. Because structure-function relationships have not yet been established for all but a few lncRNAs and there is no open reading frame as a guide, the knockout strategies available to protein-coding gene may not be applicable to the genomic loci that encode lncRNAs. Although the annotation of lncRNA genes has improved (Derrien et al. (2012)), the precise boundaries of some of the genes may still remain ambiguous, which can complicate knockout allele design. A powerful tool applied to knockout mice for protein-coding genes is the replacement of the target gene with a reporter, such as, for example, the coding sequence for β-galactosidase or a fluorescent protein, whose expression is controlled by the target gene's promoter, thereby reporting the spatial and temporal pattern of its expression in the mouse. Non-limiting examples of reporter genes are provided elsewhere herein.

Reporter gene replacement has been applied successfully to non-coding RNAs such as the well-studied Gt(ROSA) 26Sor locus (Zambrowicz, B. P., et al. (1997), *Proc Natl Acad Sci USA* 94:3789-3794), which encodes a lncRNA, and the gene for the small non-coding RNA miR-155 (Thai, T. H., et al. (2007), *Science* 316:604-608), but rules for creating such alleles for lncRNAs may need to be developed. Despite these qualifications, with thousands of lncRNAs identified, the time is ripe to explore applying the power of knockout mouse technology to this new class of genes. With this goal in mind, described herein is the creation knockout mouse lines for twenty lincRNAs, for example, each carrying a gene-ablating deletion allele with, for example, a β-galactosidase reporter replacement.

Any lncRNA locus can be modified by the methods and compositions provided herein. In one embodiment, the lncRNA is a large intergenic non-coding RNA (lincRNA). Non-limiting examples of lincRNA genes are listed in Table 1, however, the methods and compositions provided herein may be practiced with any lncRNA.

Table 1 lists the 20 lincRNA genes on 10 different chromosomes that were targeted in this study and the 26 knockout deletion alleles that were created. Members of the large intergenic non-coding RNA class were chosen for mutation because, by definition, lincRNA genes are isolated from neighboring protein-coding genes and their transcripts do not overlap (Guttman et al. (2009)). This feature allowed the design of deletion alleles that would have the least chance of interfering with the expression of nearby genes. The targeted lincRNA genes were chosen to reflect a variety of expression patterns (Cabili, M. N., et al. (2011), *Genes Dev* 25:1915-1927; Khalil, A. M., et al. (2009), *Proc Natl Acad Sci USA* 106:11667-11672), with an emphasis on neural expression, and for their potential involvement in development and the regulation of gene expression.

TABLE 1

LincRNA Knockout Deletion Alleles

| LincRNA | Deletion start exon[1] | Size (kb) | Genomic Coordinates[2] |
|---|---|---|---|
| HOTAIR | E1 | 2.3 | Ch15: 102945399-102947720 |
|  | E2 | 0.43 | Ch15: 102945399-102945826 |
| HOTTIP | E1 | 4.8 | Ch6: 52262834-52267603 |
|  | E2 | 2.2 | Ch6: 52265374-52267603 |
| Hoxa11os (HoxA11as) | E3 | 3.5 | Ch6: 52246320-52249795 |
|  | E4 | 3.1 | Ch6: 52246643-52249795 |
|  | E5 | 0.70 | Ch6: 52249094-52249795 |
| Pantr1 (LincRNA-Brn1-a) | E1 | 47 | Ch1: 42648175-42694815 |
| Pantr2 (LincRNA-Brn1-b) | E1 | 6.5 | Ch1: 42707143-42713698 |
| Ptgs2os2 (lincRNA-Cox2) | E1 | 5.9 | Ch1: 150159024-150164899 |
| Eldr (Fabl, LincRNA-Egfr) | E1 | 17 | Ch11: 16934419-16951083 |
| Lincenc1 (LincRNA-Enc1) | E2 | 26 | Ch13: 97455710-97482249 |
| Mannr (LincRNA-Evi1) | E1 | 32 | Ch3: 29891188-29923147 |
| Fendrr (LincRNA-Foxf1) | E2 | 19 | Ch8: 121054882-121074065 |
| Halr1 (Haunt, LincRNA-HoxA1) | E2 | 8.6 | Ch6: 52106776-52115377 |
| Haglr (Mdgt, LincRNA-HoxD3) | E1 | 12 | Ch2: 74750433-74762886 |
| Celrr (Celr, LincRNA-Insig2) | E2 | 50 | Ch1: 121087772-121137464 |
| Crnde (LincRNA-Irx5) | E2 | 25 | Ch8: 92325913-92350749 |
| Kantr (Spasm, LincRNA-Jarid1c) | E1 | 29 | ChX: 152298544-152327475 |
| Pint (Linc-Pint, LincRNA-Mkln1) | E2 | 32 | Ch6: 31166026-31197846 |
| Trp53cor1 (LincRNA-p21) | E1 | 22 | Ch17: 29057474-29079078 |
|  | E2 | 2.9 | Ch17: 29057474-29060353 |
| Lincppara (LincRNA-Ppara) | E1 | 29 | Ch15: 85671665-85701064 |
| Peril (LincRNA-Sox2) | E1 | 14 | Ch3: 34767849-34782292 |

TABLE 1-continued

LincRNA Knockout Deletion Alleles

| | Deletion Properties | | |
|---|---|---|---|
| LincRNA | Deletion start exon[1] | Size (kb) | Genomic Coordinates[2] |
| Tug1 (LincRNA-Tug1) | E1 E2 | 9.0 5.7 | Ch11: 3639794-3648758 Ch11: 3639794-3645518 |

[1]LincRNA genes often have multiple annotated transcripts. All deletions end at the last annotated exon.
[2]GRCm38 (GCA 000001635.3)

The design strategy for the lincRNA knockout mutations was guided by two goals. First, alleles were created that would accurately report the transcription activity of the lincRNA genes. Although there is abundant evidence for tissue-specific lincRNA expression (Cabili et al. (2011)), it was desirable to complement this knowledge base by producing the higher definition expression patterns afforded by lacZ expression profiling, which can resolve tissue and organ expression both spatially and temporally and reveal subdomains and, in some cases, cell-type specificity not resolved by tissue dissection experiments. In addition, none of the published lincRNA knockout alleles has incorporated a reporter. Second, gene-ablating deletions were created that abolished the synthesis and function of the lincRNA so that any phenotypes associated with the mutations would be informative about the critical functions of the targeted RNAs. The knockout deletions ranged in size from about 400 bp to 50 kb, with half deleting all of the annotated exons. For most of the remaining alleles the deletion started in the second exon. The application of VelociGene® engineering methods (Valenzuela, D. M., et al. (2003a), Nat Biotechnol 21:652-659) for the construction and use of large targeting vectors based on bacterial artificial chromosomes (LTVECs) was crucial to enabling construction of the large, gene ablating deletions required to ensure a null allele for this new class of large, functional RNA.

Little is known about the relationship between structure and function for lincRNA genes that could guide allele design. Experience with the disruption of the Gt(ROSA)26Sor (Zambrowicz et al., (1997)) and BIC (miR-155) (Thai et al. (2007)) genes, established that deletion and insertion after the first exon can produce reliable and tissue-specific expression of β-galactosidase or other reporters. This strategy might, however, fail to achieve a complete null mutation if the fusion transcript from the modified allele retains a functional part of the lincRNA from the 5' portion encoded in the first exon (Tsai, M. C., et al. (2010), Science 329, 689-693). The knockout allele designs indicated in Table 1 were, therefore, a compromise between the desire for a completely ablating mutation that would have the highest probability of abolishing lincRNA function and the goal of creating an allele that produced an accurate and informative gene expression profile from the β-galactosidase reporter. For example, for the HOTAIR gene two alleles were made, one that deleted nearly the entire RNA coding sequence and a second in which the deletion started in the second exon. Both alleles produced identical phenotypes (described below), but only the second functioned as a reporter of gene expression.

Figure 1:
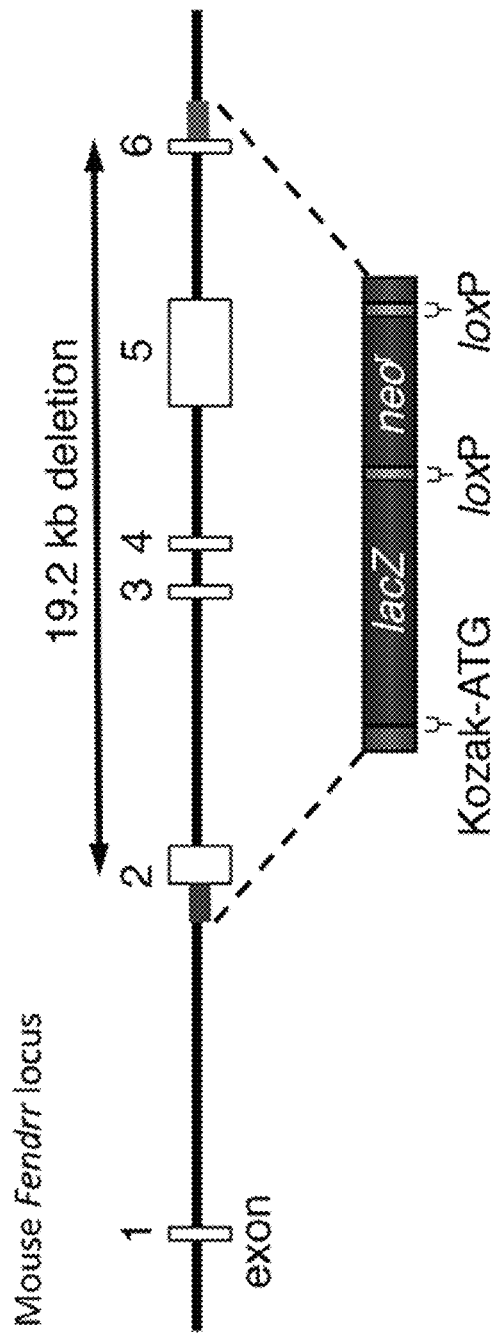
FIG. 1 illustrates a strategy for targeted disruption of the Fendrr gene locus. A partial map of the wild-type mouse Fendrr locus, including exons 1-6 is shown. Upon homologous recombination, the targeting LTVEC replaced a total of 19.2 kb of the genomic Fendrr sequence with the LacZ-neomycin resistance cassette introducing a Kozak sequence.

For lincRNAs that reside very near a protein-coding gene and may share a divergent promoter, the deletion start point was set in the second exon to avoid the chance of disrupting the transcription of the neighboring gene. FIG. 1 shows such an example for Fendrr (lincRNA-Foxf1) gene. The diagram shows an example of the design elements common to all the alleles: a targeted deletion of all or most of the sequence coding for the lincRNA and replacement with a cassette that contains a sequence from the E. coli lacZ gene that encodes β-galactosidase and a cassette (neo[r]) that expresses neomycin phosphotransferase for the selection of G418-resistant ES cell colonies. LoxP recombinase recognition sites that enable Cre-mediated excision prior to phenotypic analysis flank the drug selection cassette. As there is no functional open reading frame with which to fuse the lacZ sequence, each allele may carry a start codon and a Kozak consensus sequence (Kozak, M. (1987), Nucleic Acids Res 15, 8125-8148) for efficient translation of the β-galactosidase reporter. Non-limiting examples of Kozak consensus sequences are A/GCCRCCATGG (SEQ ID NO: 1) and GCCGCCRC-CATGG (SEQ ID NO: 2), wherein R is A or G.

The LTVEC targeting vectors were introduced into ES cells and screened for correctly targeted clones by the loss-of-allele method (Frendewey, D., et al. (2010), Methods Enzymol 476, 295-307).

The VelociMouse® method (Poueymirou, W. T., et al. (2007), Nat Biotechnol 25, 91-99) was applied to 8-cell embryo stage injection to convert the targeted ES cells into fully ES cell-derived F0 generation heterozygous mice ready for lacZ expression profiling or breeding to homozygosity. Further details of the methods for generating lncRNA knockout animals are provided in Examples 1-13 provided elsewhere herein.

ii. Reporter Expression Profiling

As described elsewhere herein, the genetic modification of the lncRNA locus can comprise a replacement of or an insertion/addition to the lncRNA locus or a portion thereof with an insert nucleic acid. In some cases, the insert nucleic acid comprises a reporter gene. In one embodiment, the reporter gene is positioned in the lncRNA locus in operable linkage with the endogenous lncRNA promoter. Such a modification allows for the expression of the reporter gene driven by the endogenous lncRNA promoter. Alternatively, the reporter gene is not placed in operable linkage with the endogenous lncRNA promoter.

Any reporter (or detectable moiety) can be used in the methods and compositions provided herein. Non-liming examples of reporters include, for example, β-galactosidase (encoded by the lacZ gene), Green Fluorescent Protein (GFP), enhanced Green Fluorescent Protein (eGFP), mPlum, mCherry, tdTomato, mStrawberry, J-Red, DsRed, mOrange, mKO, mCitrine, Venus, YPet, enhanced yellow fluorescent protein (EYFP), Emerald, CyPet, cyan fluorescent protein (CFP), Cerulean, T-Sapphire, luciferase, alkaline phosphatase, or a combination thereof.

The following description is a non-limiting example utilizing a lacZ reporter gene that encodes for β-galactosidase. The methods and compositions described herein can be performed with any reporter gene.

To survey the expression patterns of the 20 targeted lincRNA genes X-gal staining for β-galactosidase activity was applied on whole embryos or whole mount tissues and organs from adult mice. The targeted lincRNA genes exhibited a variety of unique reporter gene expression patterns (Table 2 at FIG. 11), representing most of the major organ systems and tissue types. The reporter expression patterns indicate that most of the lincRNAs are transcribed in multiple adult tissues, with one gene, Pint, exhibiting ubiquitous expression in all tissues examined. For about one-third of the lincRNA genes, expression was restricted to a single organ, for example, brain for Pantr2, Kantr, and Haglr, lungs for Mannr and Fendrr, the urogenital system for Eldr, and the ribcage for Halr1. Three of the lincRNA genes including HOTAIR, Ptgs2os2, and Haglr did not exhibit expression in any adult tissue.

Embryonic expression appears to be a common feature of lincRNAs. Examination of the β-galactosidase reporter expression in heterozygous embryos at or around embryonic day 12.5 (E12.5) revealed a variety of specific patterns for all 20 targeted lincRNA genes (Table 2 at FIG. 11, FIG. 2A). The expression profiles ranged from ubiquitous (Tug1) to highly restricted, such as epidermal for Eldr, whisker placode for Trp53cor1 (FIG. 9), or the mammary buds for Lincenc1 (FIG. 9). The spatiotemporal patterns seen in the different extents of limb bud and tail expression for HOTTIP and Hoxa11os are very similar to those reported for the adjacent protein-coding genes in the HoxA cluster (Hostikka, S. L., and Capecchi, M. R. (1998), *Mech Dev* 70:133-145; Lu, P., et al. (2008), *Development* 135:1395-1405). The expression of HOTAIR in the posterior tail bud and genital tubercle that was observed for the β-galactosidase reporter was identical to that determined by in situ hybridization (Schorderet, P., and Duboule, D. (2011), *PLoS Genet* 7:e1002071). Analysis of β-galactosidase staining at different times of embryonic development showed that for some of the lincRNAs expression began early at a restricted site and then extended beyond this initial locus at later stages (FIG. 2B), again, reminiscent of Hox protein expression (Nagy, A. (2003) Manipulating the mouse embryo: a laboratory manual, Cold Spring Harbor, N.Y., Cold Spring Harbor Laboratory Press). For example, the expression of the HOTTIP and Hoxa11os genes began in the extreme posterior of the E9.5 embryo and then extended into the limb buds at later times. Similarly, the initial expression for Celrr at a site near the anterior end of the embryos at E9.5 was maintained and expanded to the full length of the spinal cord over the next two days.

Consistent with the frequent brain expression seen among human tissue-specific lncRNAs (Derrien et al. (2012)), half of the twenty targeted mouse lincRNA genes are transcriptionally active in the brain. As with the embryonic lincRNA expression, the brain patterns (FIG. 3) were unique and varied from ubiquitous (lincppara and Pint) to highly restricted (Peril, Crnde, and Kantr). Among the 20 lincRNA genes that were targeted, only Pint showed a global whole-body expression pattern, which was mostly restricted to postnatal life. Unique to Pint, an increase in its expression with age was observed (FIG. 4). In 3-day old neonates, Pint transcription activity is low (brain) or undetectable (ribcage muscle) but then gradually appears in 3-week old mice and becomes strong and ubiquitous by 8 weeks of age. Although the strength and timing of Pint expression varies among the different organs and tissues, the general trend is a steady increase in expression after birth to a plateau in adulthood. This age-related dynamic expression pattern is novel; the inventors have not observed a similar profile in lacZ profiling experiments for hundreds of protein-coding gene knockouts.

iii. Phenotypes

Genetic modification of lncRNA loci may result in various phenotypes in the non-human animals provided herein. Such phenotypes may include, for example, premature aging-associated phenotype, defects in development of various organs including brain, skeleton, muscle or lung, defects in embryonic development, perinatal or embryonic lethality, hair loss, premature growth arrest, lordokyphosis or abnormal posture.

In one embodiment, a non-human animal comprising at least one modified long non-coding RNA (lncRNA) as described herein is characterized by having one or more of the following phenotypes: (a) a premature aging-associated phenotype; (b) perinatal lethality; (c) a defect in lung development; (d) a morphological malformation in the tail and hind limbs; (e) a loss of muscle mass in one or more tissues; (f) a defect in brain development; or (g) a combination thereof of any of (a)-(f).

In one embodiment, the genetic modification of the lncRNA locus results in lethality. In some cases the modification of the lncRNA locus is embryonic lethal. In one embodiment the modification of the lncRNA locus is perinatal lethal. In one embodiment, a disruption or knockout of Fendrr lncRNA or Peril lncRNA results in perinatal lethality. In another embodiment, a disruption or knockout of Haglr results in lethality.

In one embodiment, the genetic modification of the lncRNA locus results in a premature aging-associated phenotype. In such animals, signs of premature aging may include, for example, slow weight gain, earlier body weight plateauing, premature growth arrest, lordokyphosis by about 12 weeks of age, severe lordokyphosis by about 26 weeks of age, loss of fur at about six months, loss of hind limb muscle strength at about 6 months, or a combination thereof. In one embodiment, the genetic modification resulting in a premature aging-associated phenotype is a disruption or knockout of Pint. In one embodiment, the lncRNA is Pint, and the non-human animal is characterized by a premature aging-associated phenotype comprising: (a) a slower growth rate than that of a wild type control; (b) a decline in muscle strength; (c) fibrosis; (d) a lower body fat content than that of the wild type control; (e) a lower femur bone mineral density and bone mass than that of the wild type control; (f) a decreased muscle mass as compared with that of the wild type control; (g) a decrease in median longevity; (h) lordokyphosis; (i) organ atrophy; or (j) a combination thereof of any of (a)-(i).

The loss-of-function genetic modification of the lncRNA locus may also result in a defect in brain development. In one embodiment, the genetic modification resulting in a premature aging-associated phenotype is a disruption or knockout of Pantr2, Kantr, Peril, Celrr, Pantr1, Crnde, lincenc1, Pint, lincppara or Tug1. In a specific embodiment, the lncRNA is Pantr2. In another specific embodiment, the lncRNA is Pint.

A phenotypic analysis of the various examples of lincRNA knockout mice provided herein was performed and is described herein below.

The striking age-related increase in whole-body Pint expression revealed by the lacZ profiling (FIG. 4) suggested that Pint might have a global homeostatic role in the maintenance of normal health as the mice age. To test this hypothesis the knockout allele was bred to homozygosity and wild type (WT), heterozygous (Het), and homozygous knockout (KO) mice were followed from birth to 26 weeks of age, and examined for growth rate and any overt signs of ill health of defect. The Pint KO mice gained weight with age at a slower rate and reached a body weight plateau earlier and at a significantly lower weight than the WT mice (FIGS. 5A and B), implying premature growth arrest. Both male and female KO and Het mice exhibited the slow growth phenotype, but it was more pronounced in the males. Skeletal imaging by microCT analysis of individual mice as they aged revealed the appearance of lordokyphosis in approximately 70% of the male and female Pint KO mice by 12 weeks of age, with nearly 90% of the 26-week old KO mice showing severe lordokyphosis (FIGS. 5C and D). In contrast, only 10 to 20% of the 26-week old WT mice displayed a slight age-related lordokyphosis. Significant lordokyphosis did not appear in the Pint Het mice until 26 weeks of age, indicating an unusual age-dependent haplo-insufficiency for Pint. An age-related loss of fur in 6-month old KO mice was also observed that was more severe in females (5 out of 10 KOs) than males (2 out of 9) and was seen in only one Het and none of the WT mice of the same age. A less severe phenotype, hind limb clasping behavior when suspended from the tail, was noted in about two-thirds of the 6-month old Pint KO mice (60% of females, 67% of males) compared with about 20% WT mice of the same age. This phenotype could indicate an age-related loss of hind limb muscle strength (see FIG. 8 for another example of this phenotype in the HOTTIP knockout line). The spectrum of mutation-associated defects in the Pint knockout mice suggests a premature aging-associated phenotype.

Of the 19 lincRNA knockout mouse lines that were bred to homozygosity, two (11%), Peril and Fendrr, showed a perinatal lethality (L. A. Goff et al., unpublished). A knockout of the Fendrr gene has been recently reported (Grote et al. (2013)). The allele consisted of the insertion of a transcriptional stop element in the first exon. In embryos carrying a homozygous mutation of Fendrr, Grote et al. (2013) observed lethality at around E13.75 that was associated with a prominent omphalocele, a reduction in ventral body wall thickness, and a heart defect that caused blood accumulation in the right atrium. None of these phenotypes were observed in the Fendrr knockout line described herein, which has a 26 kb deletion from exon 2 to the last annotated exon (FIG. 1). X-gal staining of E12.5 embryos showed lacZ expression in the frontonasal process, upper respiratory tract, lungs and in the posterior AGM (Aorta-Gonad-Mesonephron) region (FIG. 6A) that was identical in both heterozygous (not shown) and homozygous embryos. An isolated look at the developing lungs at E13.5 revealed defects in the knockout embryos: the lung lobes appeared collapsed, globular, and disorganized (FIG. 6B). Mice homozygous for the deletion allele knockout of the Fendrr gene described herein survived to birth but succumbed shortly after from apparent breathing problems. The Fendrr mutant perinatal lethal phenotype was identical in mice on 2 different genetic backgrounds: the C57Bl6NTac/129S6SvEvTac hybrid background reported here and in mice further backcrossed onto a C57BL/6 background in a separate breeding program.

A number of mild phenotypes were also observed among the lincRNA knockout mice that survived to adulthood and exhibited normal Mendelian segregation of the mutant alleles (L. A. Goff et al., unpublished). Among these, there is a strong correlation between lacZ expressions and detectable phenotypes in a number of lincRNA gene knockouts such as Pantr2, HOTAIR and HOTTIP. Mice homozygous for the ablation of the Pantr2 gene (a 6.5 kb complete coding sequence deletion, Table 1) display improper development of the cerebral cortex (strong staining in the CNS), with reduced numbers of intermediate progenitor cells and defects in neuronal migration affecting the development of upper-layer projection neurons (L. A. Goff et al., unpublished). Deletions of the HOTAIR and HOTTIP genes (either complete or partial gene ablations, Table 1) caused fully penetrant morphological malformations. In HOTAIR KO mice an apparent homeotic transformation of the $4^{th}$ caudal vertebra was observed, which appears to be anatomically similar to the $3^{rd}$ caudal vertebra (FIG. 7) (specific transient lacZ staining in the tail-bud). The HOTTIP KO mice (which had positive staining in the embryonic limb buds) displayed an abnormal posture compared with wild type littermates when suspended from their tails (FIG. 8A). This behavioral abnormality was accompanied by a loss in grip endurance as measured by a test in which the mice are challenged to remain suspended on an inverted wire cage. Wild type and HOTTIP Het mutants hold on for approximately one minute, while their KO littermates release their grip within 10-20 seconds (FIG. 8B). This apparent reduction in grip strength is associated with a loss of muscle mass for the gastrocnemius but not for the tibialis anterior or the quadriceps (FIG. 8C). An approximately 40% reduction in the numbers of fibers in the gastrocnemius was observed, but no reduction in their average size (FIGS. 8D and E). In addition to the muscle defects in the HOTTIP knockout mice, a skeletal malformation was also found: a shortening in the length of the hindlimb calcaneum bone (FIG. 10).

The past several years has seen an explosion in the understanding of the non-protein-coding component of the genome, especially in mammals. In addition to the classes of non-coding functional RNAs known for decades, ribosomal, transfer, small nuclear, small nucleolar, small cytoplasmic RNAs, and the RNA components of the RNase P, RNase MRP, and telomerase enzymes, and the more recently discovered microRNAs and the PIWI-associated piRNAs, one can now include at least 10,000 members of the long non-coding RNA class (Carninci et al. (2005); Derrien et al. (2012); Djebali et al. (2012); Guttman et al. (2009); Kapranov et al. (2007)). As we come to understand the genomic presence and expression of lncRNA genes, the next goal is to discover their biological functions. As a first step to begin to tackle this challenge, mouse knockout technology has been applied, the most powerful tool for the determination of mammalian gene function, to create a resource of knockout mouse lines for 20 lincRNA genes selected for their predominantly neural lineage expression and expected function in development.

Because of the unknown structure-function relationships for the lincRNAs, it was crucial in this initial study to create knockout alleles with deletions that removed most if not all of the lincRNA coding potential to ensure that any phenotypes that were observed were the result of completely null alleles. The ambiguous and complicated annotation of many of the lincRNA loci, with multiple reported transcripts perhaps generated by alternative splicing or transcription initiation sites, adds to the difficulty of knockout allele design and would make the construction of conditional alleles that avoid the risk of hypomorphic effects difficult. New understanding of the molecular characteristics important for lincRNA function should inform the design of the next generation of lincRNA alleles with more precisely directed modifications of sequences critical to function and also permit advanced and flexible conditional strategies.

A goal of the lincRNA knockout survey described herein was to create alleles that in addition to abolishing function also reported the gene's spatiotemporal pattern of expression. Despite not having a protein coding open reading frame as a guide, alleles were successfully designed that reported gene expression for all of the 20 targeted genes. One of the alleles that produced no lacZ expression in the adult stage was Ptgs2os2 (see FIG. 2A and FIG. 9 for embryonic expression), which is known to be one of the lincRNAs most strongly induced by inflammatory signals (Carpenter, S., et al. (2013), *Sciencexpress* 1 Aug. 2013; Guttman et al. (2009)). In this survey no challenge experiments were performed, but the Ptgs2os2 knockout line should prove a valuable resource for studies of how a lincRNA's expression responds to infection or other inflammatory insults and what biological role it plays in the process.

The variety and specificity of the gene expression patterns that were observed were reminiscent of those seen with reporter alleles for protein-coding genes. Embryonic expression was a feature shared by nearly all the lincRNA genes examined. This might point to a common role for lincRNAs in the regulation of key events in development. Changing spatiotemporal patterns during embryonic development were observed, much like HOX proteins (FIG. 2B), exquisitely specific expression, such as the whisker placode staining for Trp53cor1 and the mammary bud expression for Lincenc1 (FIG. 2A and FIG. 9), ubiquitous expression in adult tissues, such as for Pint (FIG. 4), and temporal changes in the expression patterns, such as qualitative changes seen for Celrr (FIG. 2B) in embryonic development, or the novel quantitative increase in global expression with age for Pint (FIG. 4). As many of the lincRNA genes chosen for this survey were known to be expressed in neural cell lineages, brain-specific reporter expression was observed (FIG. 3), but lacZ profiling provided a higher resolution with richer biological information than assays based on cells or dissected tissue.

Among the phenotypes observed among the 19 lincRNA knockout lines bred to homozygosity, lethality was observed twice (11%), a frequency that is probably lower than would be expected for knockouts of 20 randomly chosen protein-coding genes. The somewhat low rate of lethality coupled with the subtlety of the non-lethal phenotypes seen for HOTAIR (FIG. 6), HOTTIP (FIGS. 7 and 8), Pantr2 (L. A. Goff et al., unpublished) and others (M. Sauvageau et al., unpublished) and the frequent embryonic expression suggests that the lincRNAs could buffer or modulate gene expression or other processes rather than serve single, critical functions. In this manner lincRNAs could be similar to their smaller non-coding cousins the miRNAs in that they might share redundant and overlapping targets and functions with other functional lncRNAs.

One goal of this work was to generate a resource of lincRNA knockout mouse lines with a common allele strategy and a functional reporter capability that could serve as the subjects of more in-depth expression and phenotypic studies. The addition of the LacZ cassette in each case allowed simultaneous disruption of gene function and study of the regulation of lincRNA expression patterns by X-Gal staining. These studies reveal dynamic spatial and temporal patterns of lincRNA expression during mouse embryogenesis and throughout adulthood, give significant insight into the properties of regulation/function of this new class of molecules in vivo and pinpoint regions were function of these genes can be sought. This survey could serve as a model for a large-scale project to mutate all members of the lincRNA class, similar to what has been accomplished by the International Knockout Mouse Consortium for protein-coding genes (Bradley et al. (2012)).

II. Methods for Modifying a lncRNA Locus in Non-Human Animals

Methods for genetically modifying a lncRNA locus in non-human animals, cells, tissues or embryos are provided herein.

Any lncRNA locus can be modified by the methods provided herein. Non-limiting examples of lncRNA genes comprise HOTAIR, HOTTIP, Hoxa11os (formerly named HoxA11as), Pantr1 (formerly named lincRNA-Brn1-a), Pantr2 (formerly named lincRNA-Brn1-b), Ptgs2os2 (formerly named lincRNA-Cox2), Eldr (formerly named Fab1 and lincRNA-Egfr), lincenc1 (formerly named lincRNA-Enc1), Mannr (formerly named lincRNA-Evi1), Fendrr (formerly named lincRNA-Foxf1), Halr1 (formerly named Haunt and lincRNA-HoxA1), Haglr (formerly named Mdgt and lincRNA-HoxD3), Celrr (formerly named Celr and lincRNA-Insig2), Crnde (formerly named lincRNA-Irx5), Kantr (formerly named Spasm and lincRNA-Jarid1c), Pint (formerly named linc-Pint and lincRNA-Mkln1), Trp53cor1 (formerly named lincRNA-p21), lincppara (formerly named lincRNA-Ppara), Peril (formerly named lincRNA-Sox2), Tug1 (formerly named lincRNA-Tug1), or a combination thereof.

In one embodiment, a method for modifying a lncRNA locus of interest in a pluripotent cell is provided. Such a method comprises (a) introducing into the pluripotent cell a targeting construct comprising an insert nucleic acid flanked with 5' and 3' homology arms that can undergo homologous recombination with the lncRNA locus; and (b) identifying a modified pluripotent cell comprising a targeted genetic modification at the lncRNA locus. In such methods, the genetic modification results in loss-of-function of the lncRNA. In one embodiment, the pluripotent cell is a mouse or a rat embryonic stem cell. In another embodiment, the pluripotent cell is a human iPS cell.

A. Targeting Vectors and Insert Nucleic Acids

Further provided are targeting vectors or targeting constructs to be employed in the methods for making the genetically modified non-human animals, cells, tissues or embryos provided herein.

In one embodiment, a targeting vector is provided that comprises an insert nucleic acid flanked by 5' and 3' homology arms that can undergo homologous recombination with an lncRNA locus of interest.

The targeting vectors and examples of components of the targeting vectors (i.e. insert nucleic acids, polynucleotides of interest, expression cassettes, etc.) are described in detail herein below.

i. Insert Nucleic Acid

The "insert nucleic acid" or "insert polynucleotide" comprises a segment of DNA that one desires to integrate at the target locus. In one embodiment, the insert nucleic acid comprises one or more polynucleotides of interest. In other embodiments, the insert nucleic acid can comprise one or more expression cassettes. A given expression cassette can comprise a polynucleotide of interest, a polynucleotide encoding a selection marker and/or a reporter gene along with the various regulatory components that influence expression.

Any polynucleotide of interest may be contained in the various insert polynucleotides and thereby integrated at the target genomic locus. The methods disclosed herein, provide for at least 1, 2, 3, 4, 5, 6 or more polynucleotides of interest to be integrated into the targeted lncRNA genomic locus of interest.

In one embodiment, the polynucleotide of interest contained in the insert nucleic acid encodes a reporter. In another embodiment, the polynucleotide of interest encodes for a selectable marker.

In one embodiment, the polynucleotide of interest can be flanked by site-specific recombination sites. In a specific embodiment, the site-specific recombination sites flank a segment encoding a reporter and/or a segment encoding a selectable marker.

Non-limiting examples of polynucleotides of interest, including selection markers and reporter genes that can be included within the insert nucleic acid are discussed in detail elsewhere herein.

The polynucleotide of interest within the insert polynucleotide when integrated at the target lncRNA locus can introduce one or more genetic modifications into the cell. The genetic modification can comprise a deletion of an endogenous nucleic acid sequence and/or the addition of an exogenous or heterologous or orthologous polynucleotide into the target genomic locus. In one embodiment, the genetic modification comprises a replacement of an endogenous nucleic acid sequence with an exogenous polynucleotide of interest at the target genomic locus. Thus, methods provided herein allow for the generation of a genetic modification comprising a knockout, a deletion, an insertion, a replacement ("knock-in"), a point mutation, a domain swap, an exon swap, an intron swap, a regulatory sequence swap, a gene swap, or a combination thereof in a target lncRNA locus. Such modifications may occur upon integration of the first, second, third, fourth, fifth, six, seventh, or any subsequent insert polynucleotides into the target genomic locus.

The polynucleotide of interest within the insert polynucleotide and/or integrated at the target genomic locus can comprise a sequence that is native or homologous to the cell it is introduced into; the polynucleotide of interest can be heterologous to the cell it is introduced to; the polynucleotide of interest can be exogenous to the cell it is introduced into; the polynucleotide of interest can be orthologous to the cell it is introduced into; or the polynucleotide of interest can be from a different species than the cell it is introduced into. The term "homologous" in reference to a sequence is a sequence that is native to the cell. The term "heterologous" in reference to a sequence is a sequence that originates from a foreign species, or, if from the same species, is substantially modified from its native form in composition and/or genomic locus by deliberate human intervention. The term "exogenous" in reference to a sequence is a sequence that originates from a foreign species. The term "orthologous" is a polynucleotide from one species that is functionally equivalent to a known reference sequence in another species (i.e., a species variant). The polynucleotide of interest can be from any organism of interest including, but not limited to, a prokaryote, a eukaryote, a non-human, a rodent, a hamster, a mouse, a rat, a human, a monkey, an avian, an agricultural mammal or a non-agricultural mammal. The polynucleotide of interest can further comprise a coding region, a non-coding region, a regulatory region, or a genomic DNA. Thus, the $1^{st}$, $2^{nd}$, $3^{rd}$, $4^{th}$, $5^{th}$, $6^{th}$, $7^{th}$, and/or any of the subsequent insert polynucleotides can comprise such sequences.

In one embodiment, the polynucleotide of interest can range from about 500 nucleotides to about 200 kb as described above. The polynucleotide of interest can be from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

The polynucleotide of interest within the insert polynucleotide and/or inserted at the target genomic locus can encode a polypeptide, can encode an RNA, can encode an miRNA, or it can comprise any regulatory regions or non-coding regions of interest including, for example, a regulatory sequence, a promoter sequence, an enhancer sequence, a transcriptional repressor-binding sequence, a Kozak consensus segment, a start codon, or a deletion of a non-protein-coding sequence, but does not comprise a deletion of a protein-coding sequence. In addition, the polynucleotide of interest within the insert polynucleotide and/or inserted at the target genomic locus can encode a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof.

In one embodiment, the insert nucleic acid comprises a knock-in allele of at least one exon of an endogenous gene. In one embodiment, the insert nucleic acid comprises a knock-in allele of the entire endogenous gene (i.e., "gene-swap knock-in").

In one embodiment, the insert nucleic acid comprises a regulatory element, including for example, a promoter, an enhancer, or a transcriptional repressor-binding element.

In further embodiments, the insert nucleic acid comprises a conditional allele. In one embodiment, the conditional allele is a multifunctional allele, as described in US 2011/0104799, which is incorporated by reference in its entirety. In specific embodiments, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

In one embodiment, the insert nucleic acid comprises a genetic modification in a coding sequence. In one embodiment, the genetic modification comprises a deletion mutation of a coding sequence. In one embodiment, the genetic modification comprises a fusion of two endogenous coding sequences.

In one embodiment, the genetic modification comprises a deletion of a non-protein-coding sequence, but does not comprise a deletion of a protein-coding sequence. In one embodiment, the deletion of the non-protein-coding sequence comprises a deletion of a lncRNA locus or a portion thereof. In one embodiment, the deletion of the non-protein-coding sequence comprises a deletion of a regulatory element. In one embodiment, the genetic modification comprises a deletion of a promoter. In one embodiment, the genetic modification comprises an addition of a promoter or a regulatory element. In one embodiment, the genetic modification comprises a replacement of a promoter or a regulatory element.

In one embodiment, the nucleic acid sequence of the targeting vector can comprise a polynucleotide that when integrated into the genome will produce a genetic modification of a region of the mammalian, non-human animal, or a non-human mammalian lncRNA locus, wherein the genetic modification at the lncRNA locus results in a loss-of-function of the lncRNA. In one embodiment, a lncRNA knockout ("null allele) is generated. In another embodiment, a disruption in the lncRNA locus is generated.

In further embodiments, the insert nucleic acid results in the replacement of a portion of the mammalian, non-human animal, or non-human mammalian lncRNA locus, with an insert nucleic acid sequence. In one embodiment, the insert nucleic acid sequence is a reporter nucleic acid sequence.

The given insert polynucleotide and the corresponding region of the mammalian, non-human, or non-human mammalian locus being replaced can be a non-coding region, a coding region, an intron, an exon, an untranslated region, a regulatory region, a promoter, or an enhancer or any combination thereof. Moreover, the given insert polynucleotide and/or the region of the mammalian, non-human, or non-human mammalian locus being deleted can be of any desired length, including for example, between 10-100 nucleotides in length, 100-500 nucleotides in length, 500-1 kb nucleotide in length, 1 kb to 1.5 kb nucleotide in length, 1.5 kb to 2 kb nucleotides in length, 2 kb to 2.5 kb nucleotides in length, 2.5 kb to 3 kb nucleotides in length, 3 kb to 5 kb nucleotides in length, 5 kb to 8 kb nucleotides in length, 8 kb to 10 kb nucleotides in length or more. In other instances, the size of the insertion or replacement is from about 5 kb to about 10 kb, from about 10 kb to about 20 kb, from about 20 kb to about 40 kb, from about 40 kb to about 60 kb. In other embodiments, the given insert polynucleotide and/or the region of the mammalian, human cell, or non-human mammalian locus being deleted is at least 100, 200, 300, 400, 500, 600, 700, 800, or 900 nucleotides or at least 1 kb, 2 kb, 3 kb, 4 kb, 5 kb, 6 kb, 7 kb, 8 kb, 9 kb, 10 kb, 11 kb, 12 kb, 13 kb, 14 kb, 15 kb, 16 kb, 17 kb, 18 kb, 19 kb, 20 kb, 25 kb, 30 kb, 35 kb, 40 kb, 45 kb, 50 kb or greater.

In one embodiment, the insert nucleic acid is inserted into the lncRNA locus of interest such that it is operably linked to the endogenous lncRNA promoter. In such cases, the lncRNA promoter drives expression of the insert nucleic acid sequence. In one embodiment, the insert nucleic acid sequence is a reporter nucleic acid sequence.

In some cases, the insert nucleic acid comprises a promoter. In one embodiment, the insert nucleic acid comprises a polynucleotide of interest operably linked to a promoter that drives expression of the polynucleotide of interest. In one embodiment, the polynucleotide of interest comprises a reporter nucleic acid sequence. In another embodiment, the polynucleotide of interest comprises a selection marker nucleic acid sequence.

In one embodiment, the promoter is constitutively active promoter.

In one embodiment, the promoter is an inducible promoter. In one embodiment, the inducible promoter is a chemically-regulated promoter. In one embodiment, the chemically-regulated promoter is an alcohol-regulated promoter. In one embodiment, the alcohol-regulated promoter is an alcohol dehydrogenase (alcA) gene promoter. In one embodiment, the chemically-regulated promoter is a tetracycline-regulated promoter. In one embodiment, the tetracycline-regulated promoter is a tetracycline-responsive promoter. In one embodiment, the tetracycline-regulated promoter is a tetracycline operator sequence (tetO). In one embodiment, the tetracycline-regulated promoter is a tet-On promoter. In one embodiment, the tetracycline-regulated promoter a tet-Off promoter. In one embodiment, the chemically-regulated promoter is a steroid regulated promoter. In one embodiment, the steroid regulated promoter is a promoter of a rat glucocorticoid receptor. In one embodiment, the steroid regulated promoter is a promoter of an estrogen receptor. In one embodiment, the steroid-regulated promoter is a promoter of an ecdysone receptor. In one embodiment, the chemically-regulated promoter is a metal-regulated promoter. In one embodiment, the metal-regulated promoter is a metalloprotein promoter. In one embodiment, the inducible promoter is a physically-regulated promoter. In one embodiment, the physically-regulated promoter is a temperature-regulated promoter. In one embodiment, the temperature-regulated promoter is a heat shock promoter. In one embodiment, the physically-regulated promoter is a light-regulated promoter. In one embodiment, the light-regulated promoter is a light-inducible promoter. In one embodiment, the light-regulated promoter is a light-repressible promoter.

In one embodiment, the promoter is a tissue-specific promoter. In one embodiment, the promoter is a neuron-specific promoter. In one embodiment, the promoter is a glia-specific promoter. In one embodiment, the promoter is a muscle cell-specific promoter. In one embodiment, the promoter is a heart cell-specific promoter. In one embodiment, the promoter is a kidney cell-specific promoter. In one embodiment, the promoter is a bone cell-specific promoter. In one embodiment, the promoter is an endothelial cell-specific promoter. In one embodiment, the promoter is an immune cell-specific promoter. In one embodiment, the immune cell promoter is a B cell promoter. In one embodiment, the immune cell promoter is a T cell promoter.

In one embodiment, the promoter is a developmentally-regulated promoter. In one embodiment, the developmentally-regulated promoter is active only during an embryonic stage of development. In one embodiment, the developmentally-regulated promoter is active only in an adult cell.

In specific embodiments, the promoter may be selected based on the cell type. Thus the various promoters find use in a eukaryotic cell, a mammalian cell, a non-human mammalian cell, a pluripotent cell, a non-human pluripotent cell, a human pluripotent cell, a human ES cell, a human adult stem cell, a developmentally-restricted human progenitor cell, a human iPS cell, a human cell, a rodent cell, a rat cell, a mouse cell, a hamster cell, a fibroblast or a CHO cell.

In some embodiments, the insert nucleic acid comprises a nucleic acid flanked with site-specific recombination target sequences. It is recognized the while the entire insert nucleic acid can be flanked by such site-specific recombination target sequences, any region or individual polynucleotide of interest within the insert nucleic acid can also be flanked by such sites. The site-specific recombinase can be introduced into the cell by any means, including by introducing the recombinase polypeptide into the cell or by introducing a polynucleotide encoding the site-specific recombinase into the host cell. The polynucleotide encoding the site-specific recombinase can be located within the insert nucleic acid or within a separate polynucleotide. The site-specific recombinase can be operably linked to a promoter active in the cell including, for example, an inducible promoter, a promoter that is endogenous to the cell, a promoter that is heterologous to the cell, a cell-specific promoter, a tissue-specific promoter, or a developmental stage-specific promoter. Site-specific recombination target sequences, which can flank the insert nucleic acid or any polynucleotide of interest in the insert nucleic acid can include, but are not limited to, loxP, lox511, lox2272, lox66, lox71, loxM2, lox5171, FRT, FRT11, FRT71, attp, att, FRT, rox, or a combination thereof.

In some embodiments, the site-specific recombination sites flank a polynucleotide encoding a selection marker and/or a reporter gene contained within the insert nucleic acid. In such instances following integration of the insert nucleic acid at the targeted locus the sequences between the site-specific recombination sites can be removed.

In one embodiment, the insert nucleic acid comprises a polynucleotide encoding a selection marker. The selection marker can be contained in a selection cassette. Such selection markers include, but are not limited, to neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. In one embodiment, the polynucleotide encoding the selection marker is operably linked to a promoter active in the cell. In one embodiment, the polynucleotide encoding the selection marker is flanked with site-specific recombination target sequences.

The insert nucleic acid can further comprise a reporter gene operably linked to a promoter, wherein the reporter gene encodes a reporter protein selected from the group consisting of or comprising β-galactosidase (encoded by the lacZ gene), GFP, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and/or a combination thereof. Such reporter genes can be operably linked to a promoter active in the cell. Such promoters can be an inducible promoter, a promoter that is endogenous to the reporter gene or the cell, a promoter that is heterologous to the reporter gene or to the cell, a cell-specific promoter, a tissue-specific promoter, or a developmental stage-specific promoter.

In one embodiment, the genetic modification comprises a deletion of a non-protein-coding sequence, but does not comprise a deletion of a protein-coding sequence. In one embodiment, the deletion of the non-protein-coding sequence comprises a deletion of a lncRNA locus or portion thereof. In one embodiment, the deletion of the non-protein-coding sequence comprises a deletion of a regulatory element. In one embodiment, the genetic modification comprises a deletion of a regulatory element. In one embodiment, the genetic modification comprises an addition of a promoter or a regulatory element. In one embodiment, the genetic modification comprises a replacement of a promoter or a regulatory element.

ii. Expression Cassettes

Provided herein are polynucleotides or nucleic acid molecules comprising the various components employed in a targeted genomic integration system provided herein for targeting a lncRNA locus (i.e. any one of or any combination of nuclease agents, recognition sites, insert nucleic acids, polynucleotides of interest, reporter sequences, targeting vectors, selection markers, and other components).

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Polynucleotides can comprise deoxyribonucleotides and ribonucleotides include both naturally occurring molecules and synthetic analogues, and any combination these. The polynucleotides provided herein also encompass all forms of sequences including, but not limited to, single-stranded forms, double-stranded forms, hairpins, stem-and-loop structures, and the like.

Further provided are recombinant polynucleotides comprising the various components of the targeted genomic integration system for targeting a lncRNA locus. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that is used to transform the host cells as is well known to those skilled in the art. For example, a plasmid vector can be used. Genetic elements required to successfully transform, select, and propagate host cells comprising any of the isolated nucleic acid fragments provided herein are also provided. Screening may be accomplished by Southern analysis of DNA, Northern analysis of mRNA expression, immunoblotting analysis of protein expression, or phenotypic analysis, among others.

In specific embodiments, one or more of the components of the targeted genomic integration system for targeting a lncRNA locus described herein can be provided in an expression cassette for expression in a prokaryotic cell, a eukaryotic cell, a bacterial, a yeast cell, or a mammalian cell or other organism or cell type of interest. The cassette can include 5' and 3' regulatory sequences operably linked to a polynucleotide provided herein. "Operably linked" comprises a relationship wherein the components operably linked function in their intended manner. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, operably linked means that the coding regions are in the same reading frame. In another instance, a nucleic acid sequence encoding a protein may be operably linked to regulatory sequences (e.g., promoter, enhancer, silencer sequence, etc.) so as to retain proper transcriptional regulation. The cassette may additionally contain at least one additional polynucleotide of interest to be co-introduced into the organism. Alternatively, the additional polynucleotide of interest can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selection marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in mammalian cell or a host cell of interest. The regulatory regions (i.e., promoters, transcriptional regulatory regions, Kozak sequence, and translational termination regions) and/or a polynucleotide provided herein may be native/analogous to the host cell or to each other. Alternatively, the regulatory regions and/or a polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the host cell, or may be derived from another source (i.e., foreign or heterologous) to the promoter, the recombinant polynucleotide, the host cell, or any combination thereof.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a Kozak consensus sequence, a ribosome binding site, an RNA processing signal, a transcription termination site, and/or a polyadenylation signal.

The expression cassette containing the polynucleotides provided herein can also comprise a selection marker gene for the selection of transformed cells. Selectable marker genes are utilized for the selection of transformed cells or tissues.

Where appropriate, the sequences employed in the methods and compositions (i.e., the polynucleotide of interest, the nuclease agent, etc.) may be optimized for increased expression in the cell. That is, the genes can be synthesized using codons preferred in a given cell of interest including, for example, mammalian-preferred codons, human-preferred codons, rodent-preferred codon, mouse-preferred codons, rat-preferred codons, hamster-preferred codons, etc. for improved expression.

The various methods and compositions provided herein can employ selection markers. Various selection markers can be used in the methods and compositions disclosed herein. Such selection markers can, for example, impart resistance to an antibiotic such as G418, hygromycin, blasticidin, neomycin, or puromycin. Such selection markers include neomycin phosphotransferase (neo$^r$), hygromycin B phosphotransferase (hyg$^r$), puromycin-N-acetyltransferase (puro$^r$), and blasticidin S deaminase (bsr$^r$). In still other embodiments, the selection marker is operably linked to an inducible promoter and the expression of the selection marker is toxic to the cell. Non-limiting examples of such selection markers include xanthine/guanine phosphoribosyl transferase (gpt), hypoxanthine-guanine phosphoribosyl-transferase (HGPRT) or herpes simplex virus thymidine kinase (HSV-TK). The polynucleotide encoding the selection markers are operably linked to a promoter active in the cell.

iii. Targeting Vectors

Targeting vectors are employed to introduce the insert nucleic acid into the lncRNA locus of interest of the eukaryotic, non-human, mammalian, non-human mammalian, human, rodent, mouse, rat or hamster nucleic acid. The targeting vector comprises the insert nucleic acid and further comprises a 5' and a 3' homology arm, which flank the insert nucleic acid. The homology arms, which flank the insert nucleic acid, correspond to regions within the target lncRNA locus of the eukaryotic, non-human, mammalian, non-human mammalian, human, rodent, mouse, rat or hamster nucleic acid. For ease of reference, the corresponding cognate genomic regions within the targeted genomic locus are referred to as "target sites". For example, a targeting vector can comprise a first insert nucleic acid flanked by a first and a second homology arm complementary to a first and a second target site. As such, the targeting vector thereby aids in the integration of the insert nucleic acid into the target locus nucleic acid through a homologous recombination event that occurs between the homology arms and the complementary target sites within the genome of the cell.

In one embodiment, the target locus of the eukaryotic, mammalian, non-human mammalian, human, rodent, mouse or hamster nucleic acid comprises a first nucleic acid sequence that is complementary to the 5' homology arm and a second nucleic acid sequence that is complementary to the 3' homology arm. In one embodiment, the first and the second nucleic acid sequences are separated by at least 5 kb. In another embodiment, the first and the second nucleic acid sequences are separated by at least 1 kb but less than 50 kb. In one embodiment, the first and the second nucleic acid sequences are separated by at least 2 kb. In one embodiment, the first and the second nucleic acid sequences are separated by at least 3 kb, at least 4 kb, at least 5 kb, at least 6 kb, at least 7 b, at least 8 kb, at least 9 kb, at least 10 kb, at least 15 kb, at least 20 kb, at least 30 kb, at least 40 kb, or at least 50 kb. In still further embodiments, the first and the second nucleic acid sequence is separated by at least 1 kb but less than 2 kb, at least 2 kb but less than 3 kb, at least 4 kb but less than 5 kb, at least 5 kb but less than 6 kb, at least 6 kb but less than 7 kb, at least 7 kb but less than 8 kb, at least about 8 kb but less than 9 kb, at least 9 kb but less than 10 kb, or at least 10 kb but less than 15 kb, at least about 15 kb but less than about 20 kb, at least about 20 kb but less than about 30 kb, or at least about 40 kb but less than about 50 kb.

A homology arm of the targeting vector can be of any length that is sufficient to promote a homologous recombination event with a corresponding target site, including for example, at least 5-10 kb, 5-15 kb, 10-20 kb, 20-30 kb, 30-40 kb, 40-50 kb, 50-60 kb, 60-70 kb, 70-80 kb, 80-90 kb, 90-100 kb, 100-110 kb, 110-120 kb, 120-130 kb, 130-140 kb, 140-150 kb, 150-160 kb, 160-170 kb, 170-180 kb, 180-190 kb, 190-200 kb in length or greater. As outlined in further detail below, large targeting vectors can employ targeting arms of greater length. In a specific embodiment, the sum total of the 5' homology arm and the 3' homology arm is at least 10 kb or the sum total of the 5' homology arm and the 3' homology arm is at least about 16 kb to about 100 kb or about 30 kb to about 100 kb. In other embodiments, the size of the sum total of the total of the 5' and 3' homology arms of the LTVEC is about 10 kb to about 150 kb, about 10 kb to about 100 kb, about 10 kb to about 75 kb, about 20 kb to about 150 kb, about 20 kb to about 100 kb, about 20 kb to about 75 kb, about 30 kb to about 150 kb, about 30 kb to about 100 kb, about 30 kb to about 75 kb, about 40 kb to about 150 kb, about 40 kb to about 100 kb, about 40 kb to about 75 kb, about 50 kb to about 150 kb, about 50 kb to about 100 kb, or about 50 kb to about 75 kb, about 10 kb to about 30 kb, about 20 kb to about 40 kb, about 40 kb to about 60 kb, about 60 kb to about 80 kb, about 80 kb to about 100 kb, about 100 kb to about 120 kb, or from about 120 kb to about 150 kb. In one embodiment, the size of the deletion is the same or similar to the size of the sum total of the 5' and 3' homology arms of the LTVEC.

A homology arm and a target site (i.e., cognate genomic region) "complement" or are "complementary" to one another when the two regions share a sufficient level of sequence identity to one another to act as substrates for a homologous recombination reaction. By "homology" is meant DNA sequences that are either identical or share sequence identity to a corresponding or "complementary" sequence. The sequence identity between a given target site and the corresponding homology arm found on the targeting vector can be any degree of sequence identity that allows for homologous recombination to occur. For example, the amount of sequence identity shared by the homology arm of the targeting vector (or a fragment thereof) and the target site (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a complementary region of homology between the homology arm and the complementary target site can be of any length that is sufficient to promote homologous recombination at the cleaved recognition site. For example, a given homology arm and/or complementary target site can comprise complementary regions of homology that are at least 5-10 kb, 5-15 kb, 10-20 kb, 20-30 kb, 30-40 kb, 40-50 kb, 50-60 kb, 60-70 kb, 70-80 kb, 80-90 kb, 90-100 kb, 100-110 kb, 110-120 kb, 120-130 kb, 130-140 kb, 140-150 kb, 150-160 kb, 160-170 kb, 170-180 kb, 180-190 kb, 190-200 kb, 200 kb to 300 kb in length or greater (such as described in the LTVEC vectors described elsewhere herein) such that the homology arm has sufficient homology to undergo homologous recombination with the corresponding target sites within the genome of the cell. For ease of reference the homology arms are referred to herein as a 5' and a 3' homology arm. This terminology relates to the relative position of the homology arms to the insert nucleic acid within the targeting vector.

The homology arms of the targeting vector are therefore designed to be complementary to a target site with the targeted locus. Thus, the homology arms can be complementary to a locus that is native to the cell, or alternatively they can be complementary to a region of a heterologous or exogenous segment of DNA that was integrated into the genome of the cell, including, but not limited to, transgenes, expression cassettes, or heterologous or exogenous regions of genomic DNA. Alternatively, the homology arms of the targeting vector can be complementary to a region of a human artificial chromosome or any other engineered genomic region contained in an appropriate host cell. Still further, the homology arms of the targeting vector can be complementary to or be derived from a region of a BAC library, a cosmid library, or a P1 phage library. Thus, in specific embodiments, the homology arms of the targeting vector are complementary to a eukaryotic, non-human, mammalian, non-human mammalian, human, rodent, mouse or rat genomic locus that is native, heterologous or exogenous to a given cell. In one embodiment, the homology arms are derived from a synthetic DNA.

The targeting vector (such as a large targeting vector) can also comprise a selection cassette or a reporter gene as discussed elsewhere herein. The selection cassette can comprise a nucleic acid sequence encoding a selection marker, wherein the nucleic acid sequence is operably linked to a promoter as discussed elsewhere herein. The selection marker and/or the reporter gene of the targeting vector can be flanked by the 5' and 3' homology arms or found either 5' or 3' to the homology arms.

In one embodiment, a targeting vector comprises an insert nucleic acid comprising a first nucleotide sequence that encodes a reporter. In some cases, following the homologous recombination with the lncRNA locus of interest, the first nucleotide sequence that encodes the reporter is operably linked to an endogenous promoter that drives expression of an lncRNA at the lncRNA locus. In a further embodiment, the insert nucleic acid sequence of the targeting vector comprises a Kozak consensus sequence. In such cases where the insert nucleic acid comprises a reporter, the Kozak consensus sequence can be operably linked to the nucleic acid sequence encoding the reporter.

In another embodiment, the insert nucleic acid of the targeting vector comprises a second nucleotide sequence that encodes a selectable marker. In some cases, the second nucleic acid is operably linked to a promoter.

In one embodiment, the first and/or second nucleotide sequence of the insert nucleic acid comprises a Kozak consensus sequence.

In one embodiment, the targeting vector (such as a large targeting vector) comprises a reporter gene and/or a selectable marker gene operably linked to a promoter as described elsewhere herein. Such reporter genes and/or selectable marker genes can be operably linked to a promoter active in the cell as described elsewhere herein.

In one embodiment, the targeting vector comprises a site-specific recombinase gene. In one embodiment, the site-specific recombinase gene encodes a Cre recombinase. In one embodiment, the Cre recombinase gene is Crei, wherein two exons encoding the Cre recombinase are separated by an intron to prevent its expression in a prokaryotic cell. In one embodiment, the site-specific recombinase gene encodes a Dre recombinase.

In one embodiment, the Cre recombinase gene further comprises a nuclear localization signal to facilitate localization of Cre (or any recombinase or nuclease agent) to the nucleus (e.g., the gene is an NL-Cre gene). In a specific embodiment, the Cre recombinase gene further comprises a nuclear localization signal and an intron (e.g., NL-Crei).

In various embodiments, a suitable promoter for expression of the Cre or Crei recombinase discussed above is selected from or comprises a Prm1, Blimp1, Gata6, Gata4, Igf2, Lhx2, Lhx5, and/or Pax3. In a specific embodiment, the promoter is the Gata6 or Gata4 promoter. The various promoters can be from any organism, including for example, a rodent such as a mouse or a rat, a eukaryote, a non-human mammal, a mammal, a human or a hamster. In another specific embodiment, the promoter is a Prm1 promoter. In another specific embodiment, the promoter is a mouse Prm1 promoter. In another specific embodiment, the promoter is a Blimp1 promoter or a fragment thereof, e.g., a 1 kb or 2 kb fragment of a Blimp1 promoter. See, for example, U.S. Pat. No. 8,697,851 and U.S. Application Publication 2013-0312129, both of which are herein incorporated by reference in their entirety.

In one embodiment, the insert nucleic acid comprises a nucleotide sequence flanked by two site-specific recombination sites. Examples of site-specific recombination sites include, but are not limited to, loxP, lox511, lox2272, lox66, lox71, loxM2, lox5171, FRT, FRT11, FRT71, attp, att, FRT, rox, and a combination thereof.

iv. Large Targeting Vectors

The term "large targeting vector" or "LTVEC" includes large targeting vectors that comprise homology arms that correspond to and are derived from nucleic acid sequences larger than those typically used by other approaches intended to perform homologous targeting in cells and/or comprising insert polynucleotides comprising nucleic acid sequences larger than those typically used by other approaches intended to perform homologous recombination targeting in cells. In specific embodiments, the homology arms and/or the insert polynucleotide of the LTVEC comprises a genomic sequence of a eukaryotic cell. The size of the LTVEC is too large to enable screening of targeting events by conventional assays, e.g., southern blotting and long-range (e.g., 1 kb-5 kb) PCR. Examples of the LTVEC, include, but are not limited to, vectors derived from a bacterial artificial chromosome (BAC), a human artificial chromosome or a yeast artificial chromosome (YAC). Non-limiting examples of LTVECs and methods for making them are described, e.g., in U.S. Pat. Nos. 6,586,251, 6,596,541, 7,105,348, and WO 2002/036789 (PCT/US01/45375), each of which is herein incorporated by reference.

The LTVEC can be of any length, including, but not limited to, at least about 10 kb, about 15 kb, about 20 kb, about 30 kb, about 40 kb, about 50 kb, about 60 kb, about 70 kb, about 80 kb, about 90 kb, about 100 kb, about 150 kb, about 200 kb, from about 10 kb to about 15 kb, about 15 kb to about 20 kb, about 20 kb to about 30 kb, from about 30 kb to about 50 kb, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb.

In one embodiment, the homology arms of the LTVEC are derived from a BAC library, a cosmid library, or a P1 phage library. In other embodiments, the homology arms are derived from the targeted lncRNA genomic locus of the cell and in some instances the target genomic locus that the LTVEC is designed to target is not targetable using a conventional method. In still other embodiments, the homology arms are derived from a synthetic DNA.

In one embodiment, a sum total of the upstream homology arm and the downstream homology arm in the LTVEC is at least 10 kb. In other embodiments, the upstream homology arm ranges from about 5 kb to about 100 kb. In one embodiment, the downstream homology arm ranges from about 5 kb to about 100 kb. In other embodiments, the sum total of the upstream and downstream homology arms are from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. In one embodiment, the size of the deletion is the same or similar to the size of the sum total of the 5' and 3' homology arms of the LTVEC.

In one embodiment, the LTVEC comprises a selection cassette or a reporter gene as discussed elsewhere herein.

III. Methods of Introducing Sequences and Generation of Transgenic Animals

As outlined above, methods and compositions are provided herein to allow for the targeted genetic modification of one or more lncRNA loci. It is further recognized that additional targeted genetic modification can be made. Such systems that allow for these targeted genetic modifications can employ a variety of components and for ease of reference, herein the term "targeted genomic integration system" generically includes all the components required for an integration event (i.e. the various nuclease agents, recognition sites, insert DNA polynucleotides, targeting vectors, target genomic locus, and polynucleotides of interest).

The methods provided herein comprise introducing into a cell one or more polynucleotides or polypeptide constructs comprising the various components of the targeted genomic integration system. "Introducing" means presenting to the cell the sequence (polypeptide or polynucleotide) in such a manner that the sequence gains access to the interior of the cell. The methods provided herein do not depend on a particular method for introducing any component of the targeted genomic integration system into the cell, only that the polynucleotide gains access to the interior of a least one cell. Methods for introducing polynucleotides into various cell types are known in the art and include, but are not limited to, stable transfection methods, transient transfection methods, and virus-mediated methods.

In some embodiments, the cells employed in the methods and compositions have a DNA construct stably incorporated into their genome. "Stably incorporated" or "stably introduced" means the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

Transfection protocols as well as protocols for introducing polypeptides or polynucleotide sequences into cells may vary. Non-limiting transfection methods include chemical-based transfection methods include the use of liposomes; nanoparticles; calcium phosphate (Graham et al. (1973). *Virology* 52 (2): 456-67, Bacchetti et al. (1977) *Proc Natl Acad Sci USA* 74 (4): 1590-4 and, Kriegler, M (1991). *Transfer and Expression: A Laboratory Manual*. New York: W. H. Freeman and Company. pp. 96-97); dendrimers; or cationic polymers such as DEAE-dextran or polyethylenimine. Non chemical methods include electroporation; Sonoporation; and optical transfection. Particle-based transfection include the use of a gene gun, magnet assisted transfection (Bertram, J. (2006) *Current Pharmaceutical Biotechnology* 7, 277-28). Viral methods can also be used for transfection.

Non-human animals can be generated employing the various methods disclosed herein. Such methods comprises (1) integrating one or more polynucleotide of interest at the target lncRNA genomic locus of interest of a pluripotent cell of the non-human animal to generate a genetically modified pluripotent cell comprising the insert polynucleotide in the targeted lncRNA genomic locus employing the methods disclosed herein; (2) selecting the genetically modified pluripotent cell having the one or more polynucleotides of interest at the target lncRNA genomic locus; (3) introducing the genetically modified pluripotent cell into a host embryo of the non-human animal, e.g., at a pre-morula stage; and (4) implanting the host embryo comprising the genetically modified pluripotent cell into a surrogate mother to generate an F0 generation derived from the genetically modified pluripotent cell. Similar methods can be employed to target a challenging target chromosomal locus. The non-human animal can be a non-human mammal, a rodent, a mouse, a rat, a hamster, a monkey, an agricultural mammal or a domestic mammal, or a fish or a bird.

The pluripotent cell can be a human ES cell, a non-human ES cell, a rodent ES cell, a mouse ES cell, a rat ES cell, a hamster ES cell, a monkey ES cell, an agricultural mammal ES cell or a domesticated mammal ES cell. In other embodiments, the pluripotent cell is a non-human cell, a mammalian cell, human cell, a non-human mammalian cell, a human pluripotent cell, a human ES cell, a human adult stem cell, a developmentally-restricted human progenitor cell, a human iPS cell, a rodent cell, a rat cell, a mouse cell, a hamster cell. In one embodiment, the targeted genetic modification results in the loss-of-function of the lncRNA.

Nuclear transfer techniques can also be used to generate the non-human animals. Briefly, methods for nuclear transfer include the steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes can be matured in a variety of medium known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference.

Other methods for making a non-human animal comprising in its germline one or more genetic modifications as described herein is provided, comprising: (a) modifying a targeted genomic lncRNA locus of a non-human animal in a prokaryotic cell employing the various methods described herein; (b) selecting a modified prokaryotic cell comprising the genetic modification at the targeted genomic locus; (c) isolating the genetically modified targeting vector from the genome of the modified prokaryotic cell; (d) introducing the genetically modified targeting vector into a pluripotent cell of the non-human animal to generate a genetically modified pluripotent cell comprising the insert nucleic acid at the targeted lncRNA genomic locus; (e) selecting the genetically modified pluripotent cell; (f) introducing the genetically modified pluripotent cell into a host embryo of the non-human animal at a pre-morula stage; and (g) implanting the host embryo comprising the genetically modified pluripotent cell into a surrogate mother to generate an F0 generation derived from the genetically modified pluripotent cell. In such methods the targeting vector can comprise a large targeting vector. The non-human animal can be a non-human mammal, a rodent, a mouse, a rat, a hamster, a monkey, an agricultural mammal or a domestic mammal. The pluripotent cell can be a human ES cell, a non-human ES cell, a rodent ES cell, a mouse ES cell, a rat ES cell, a hamster ES cell, a monkey ES cell, an agricultural mammal ES cell or a domestic mammal ES cell. In other embodiments, the pluripotent cell is a non-human cell, mammalian cell, human cell, a non-human mammalian cell, a human pluripotent cell, a human ES cell, a human adult stem cell, a developmentally-restricted human progenitor cell, a human iPS cell, a human cell, a rodent cell, a rat cell, a mouse cell, a hamster cell. In one embodiment, the targeted genetic modification results in the loss-of-function of the lncRNA.

In further methods, the isolating step (c) further comprises (c1) linearizing the genetically modified targeting vector (i.e., the genetically modified LTVEC). In still further embodiments, the introducing step (d) further comprises (d1) introducing a nuclease agent into the pluripotent cell to facilitate homologous recombination. In one embodiment, selecting steps (b) and/or (e) are carried out by applying a selectable agent as described herein to the prokaryotic cell or the pluripotent cell. In one embodiment, selecting steps (b) and/or (e) are carried out via a modification of allele (MOA) assay as described herein.

In some embodiments, various genetic modifications of the target genomic loci described herein can be carried out by a series of homologous recombination reactions (BHR) in bacterial cells using an LTVEC derived from Bacterial Artificial Chromosome (BAC) DNA using VELOCIGENE® genetic engineering technology (see, e.g., U.S. Pat. No. 6,586,251 and Valenzuela, D. M. et al. (2003), *Nature Biotechnology* 21(6): 652-659, which is incorporated herein by reference in their entireties).

In some embodiments, the lncRNA targeted pluripotent and/or totipotent cells comprising various genetic modifications as described herein are used as insert donor cells and introduced into a pre-morula stage embryo from a corresponding organism, e.g., an 8-cell stage mouse embryo, via the VELOCIMOUSE® method (see, e.g., U.S. Pat. Nos. 7,576,259, 7,659,442, 7,294,754, and US 2008-0078000 A1, all of which are incorporated by reference herein in their entireties). The non-human animal embryo comprising the genetically modified pluripotent and/or totipotent cells is incubated until the blastocyst stage and then implanted into a surrogate mother to produce an F0 generation. In some embodiments, targeted mammalian ES cells comprising various genetic modifications as described herein are introduced into a blastocyst stage embryo. Non-human animals bearing the genetically modified genomic locus (i.e. a lncRNA locus) can be identified via modification of allele (MOA) assay as described herein. The resulting F0 generation non-human animal derived from the genetically modified pluripotent and/or totipotent cells is crossed to a wild-type non-human animal to obtain F1 generation offspring. Following genotyping with specific primers and/or probes, F1 non-human animals that are heterozygous for the genetically modified genomic locus are crossed to each other to produce F2 generation non-human animal offspring that are homozygous for the genetically modified genomic locus.

In one embodiment, a method for making a non-human animal comprising a genetic modification in at least one lncRNA locus is provided. Such a method comprising: (a) contacting a pluripotent cell with a targeting construct comprising an insert nucleic acid flanked by 5' and 3' homology arms; wherein the targeting construct undergoes homologous recombination with the lncRNA locus in a genome of the cell to form a modified pluripotent cell; (b)

introducing the modified pluripotent cell into a host embryo; and (c) gestating the host embryo in a surrogate mother, wherein the surrogate mother produces progeny comprising a modified lncRNA locus, wherein said genetic modification results in loss-of-function of the at least one lncRNA.

IV. Cells

The various methods described herein employ a genomic locus targeting system for modifying a lncRNA locus in a cell. Such cells include prokaryotic cells such as bacterial cells including *E. coli*, or eukaryotic cells such as yeast, insect, amphibian, plant, or mammalian cells, including, but not limited to a mouse cell, a rat cell, a hamster cell, a rabbit cell, a pig cell, a bovine cell, a deer cell, a sheep cell, a goat cell, a chicken cell, a cat cell, a dog cell, a ferret cell, a primate (e.g., marmoset, rhesus monkey) cell, and the like and cells from domesticated mammals or cells from agricultural mammals. Some cells are non-human, particularly non-human mammalian cells. In some embodiments, for those mammals for which suitable genetically modifiable pluripotent cells are not readily available, other methods are employed to reprogram somatic cells into pluripotent cells, e.g., via introduction into somatic cells of a combination of pluripotency-inducing factors, including, but not limited to, Oct3/4, Sox2, KLF4, Myc, Nanog, LIN28, and Glis1. In such methods, the cell can also be a mammalian cell, human cell, a non-human mammalian cell, a non-human cell, a cell from a rodent, a rat, a mouse, a hamster, a fibroblast cell or any other host cell. In other embodiments, the cell is a pluripotent cell, an induced pluripotent stem (iPS) cell, a non-human embryonic stem (ES) cell. Such cells include pluripotent cells, including, for example, induced pluripotent stem (iPS) cells, human iPS cells, mouse embryonic stem (ES) cells, rat embryonic stem (ES) cells, human embryonic (ES) cells, or developmentally restricted human progenitor cells, a rodent embryonic stem (ES) cell, a mouse embryonic stem (ES) cell or a rat embryonic stem (ES) cell.

Non-limiting embodiments include:

1. A non-human animal comprising in its genome at least one modified long non-coding RNA (lncRNA) locus, wherein the at least one modified lncRNA locus comprises a loss-of-function mutation in a nucleic acid sequence that encodes a lncRNA.

2. The non-human animal of embodiment 1, wherein the lncRNA is a large intergenic non-coding RNA (lincRNA).

3. The non-human animal of any one of embodiments 1 or 2, wherein the loss-of-function mutation is characterized by a disruption or a knockout of at least one lncRNA function.

4. The non-human animal of embodiment 3, wherein the modified lncRNA locus comprises a deletion of one or more exons that encode the lncRNA or a portion thereof.

5. The non-human animal of embodiment 4, wherein the disruption or knockout comprises (a) a deletion of one or more exons within the lncRNA locus starting in a second exon of a lncRNA locus; (b) a deletion of one or more exons within the lncRNA locus starting in a first exon of a lncRNA locus; or (c) deletion of an entire RNA coding region of a lncRNA locus.

6. The non-human animal of embodiment 3, wherein the disruption or knockout comprises a replacement of a lncRNA locus or a portion thereof with an insert nucleic acid.

7. The genetically modified non-human animal of embodiment 6, wherein the insert nucleic acid comprises a first nucleotide sequence that encodes a reporter.

8. The genetically modified non-human animal of embodiment 7, wherein the first nucleotide sequence is operably linked to a promoter that drives expression of the reporter.

9. The genetically modified non-human animal of embodiment 7, wherein the first nucleotide sequence that encodes the reporter is positioned in a lncRNA locus in operable linkage with an endogenous lncRNA promoter, wherein the endogenous lncRNA promoter drives expression of the nucleotide sequence.

10. The non-human animal of embodiment 9, wherein the expression of the nucleic acid sequence follows an expression pattern of the lncRNA.

11. The genetically modified non-human animal of embodiment 7, wherein the first nucleotide sequence comprises a Kozak consensus sequence.

12. The non-human animal of any one of embodiments 6-11, wherein the replacement comprises (a) replacement of one or more exons within a lncRNA locus starting in the second exon of the lncRNA locus with the insert nucleic acid; (b) replacement of one or more exons within a lncRNA locus starting in the first exon of the lncRNA locus with the insert nucleic acid; or (c) replacement of the entire RNA coding region of a lncRNA locus with the insert nucleic acid.

13. The non-human animal of any one of embodiments 6-12, wherein the reporter is any of β-galactosidase, Green Fluorescent Protein (GFP), enhanced Green Fluorescent Protein (eGFP), mPlum, mCherry, tdTomato, mStrawberry, J-Red, DsRed, mOrange, mKO, mCitrine, Venus, YPet, enhanced yellow fluorescent protein (EYFP), Emerald, CyPet, cyan fluorescent protein (CFP), Cerulean, T-Sapphire, luciferase, alkaline phosphatase, or a combination thereof.

14. The non-human animal of any one of embodiments 6-13, wherein the insert nucleic acid further comprises a second nucleic acid sequence that encodes a selectable marker, wherein the second nucleic acid sequence is operably linked to a promoter.

15. The non-human animal of embodiment 14, wherein the insert nucleic acid comprises site-specific recombination sites flanking a segment encoding the reporter and/or a segment encoding the selectable marker.

16. The non-human animal of any one of embodiments 1-15, wherein the lncRNA comprises Pint, Celrr, Crnde, Eldr, Fendrr, Halr1, Hotair, Hottip, Hoxa11os, Pantr1, Pantr2, Ptgs2os2, lincenc1, Trp53cor1, lincppara, Mannr, Haglr, Peril, Kantr, Tug1, or a combination thereof.

17. The non-human animal of any one of embodiments 1-15, wherein said non-human animal is characterized by having one or more following phenotypes: (a) a premature aging-associated phenotype; (b) perinatal lethality; (c) a defect in lung development; (d) a morphological malformation in the tail and hind limbs; (e) a loss of muscle mass in one or more tissues; or (f) a combination thereof of any of (a)-(e).

18. The non-human animal of embodiment 1, wherein the lncRNA is Pint, and the non-human animal is characterized by a premature aging-associated phenotype comprising: (a) a slower growth rate than that of a wild type control; (b) a decline in muscle strength; (c) fibrosis; (d) a lower body fat content than that of the wild type control; (e) a lower femur bone mineral density and bone mass than that of the wild type control; (f) a decreased muscle mass as compared with that of the wild type control; (g) a decrease in median longevity; (h) lordokyphosis; (i) organ atrophy; or (j) a combination thereof of any of (a)-(i).

19. The non-human animal of any one of embodiments 1-15, wherein said non-human animal exhibits a defect in brain development.

20. The non-human animal of embodiment 19, wherein the lncRNA is Pantr2, Kantr, Peril, Celrr, Pantr1, Crnde, lincenc1, Pint, lincppara, or Tug1.

21. The genetically modified non-human animal of any one of embodiments 1-20, wherein the non-human animal is a mammal.

22. The genetically modified non-human animal of embodiment 21, wherein the mammal is a rodent.

23. The genetically modified non-human animal of embodiment 22, wherein the mammal is a mouse, a rat, or a hamster.

24. A cell, tissue, or embryo derived from the non-human animal of any one of embodiments 1-23.

25. A targeting vector, comprising an insert nucleic acid flanked by 5' and 3' homology arms that can undergo homologous recombination with an lncRNA locus of interest.

26. The targeting vector of embodiment 25, wherein the insert nucleic acid comprises a first nucleic acid sequence that encodes a reporter.

27. The targeting vector of embodiment 26, wherein following the homologous recombination with the lncRNA locus of interest, the first nucleic acid sequence that encodes the reporter is operably linked to an endogenous promoter that drives expression of an lncRNA at the lncRNA locus.

28. The targeting vector of any one of embodiments 26-27, wherein the reporter is any of β-galactosidase, Green Fluorescent Protein (GFP), enhanced Green Fluorescent Protein (eGFP), mPlum, mCherry, tdTomato, mStrawberry, J-Red, DsRed, mOrange, mKO, mCitrine, Venus, YPet, enhanced yellow fluorescent protein (EYFP), Emerald, CyPet, cyan fluorescent protein (CFP), Cerulean, T-Sapphire, luciferase, alkaline phosphatase, or a combination thereof.

29. The targeting vector construct of any one of embodiments 25-28, wherein the insert nucleic acid further comprises a second nucleic acid sequence that encodes a selectable marker, wherein the second nucleic acid is operably linked to a promoter.

30. The targeting vector of embodiment 29, further comprising site-specific recombination sites flanking a segment encoding the reporter and/or a segment encoding the selectable marker nucleic acid.

31. The targeting vector of embodiment 26 or 29, wherein the first and/or the second nucleic acid sequence further comprises a Kozak consensus sequence.

32. The targeting vector of any one of embodiments 25-31, wherein the insert nucleic acid further comprises a promoter that drives expression of the reporter.

33. A method for making a non-human animal comprising a genetic modification in at least one lncRNA locus, the method comprising: (a) contacting a pluripotent cell with a targeting construct comprising an insert nucleic acid flanked by 5' and 3' homology arms; wherein the targeting construct undergoes homologous recombination with the lincRNA locus in a genome of the cell to form a modified pluripotent cell; (b) introducing the modified pluripotent cell into a host embryo; and (c) gestating the host embryo in a surrogate mother, wherein the surrogate mother produces progeny comprising a modified lncRNA locus, wherein said genetic modification results in loss-of-function of the at least one lncRNA.

34. The method of embodiment 33, wherein the lncRNA is a lincRNA.

35. The method of any one of embodiments 33-34, wherein the genetic modification comprises a disruption or a knockout of at least one lncRNA function.

36. The method of any one of embodiments 33-35, wherein the lncRNA comprises Pint, Celrr, Crnde, Eldr, Fendrr, Halr1, Hotair, Hottip, Hoxa11os, Pantr1, Pantr2, Ptgs2os2, lincenc1, Trp53cor1, lincppara, Mannr, Haglr, Peril, Kantr, Tug1, or a combination thereof.

37. A method for modifying a lncRNA locus in a pluripotent cell, comprising (a) introducing into the pluripotent cell a targeting construct comprising an insert nucleic acid flanked with 5' and 3' homology arms that can undergo homologous recombination with the lncRNA locus; and (b) identifying a modified pluripotent cell comprising a targeted genetic modification at the lncRNA locus, wherein the genetic modification results in loss-of-function of the lncRNA function.

38. The method of embodiment 37, wherein the pluripotent cell is a human iPS cell.

39. The method of embodiment 37, wherein the pluripotent cell is a mouse or a rat embryonic stem (ES) cell.

40. The method of any one of embodiments 37-39, wherein the lncRNA comprises Pint, Celrr, Crnde, Eldr, Fendrr, Halr1, Hotair, Hottip, Hoxa11os, Pantr1, Pantr2, Ptgs2os2, lincenc1, Trp53cor1, lincppara, Mannr, Haglr, Peril, Kantr, Tug1, or a combination thereof.

41. A genetically modified non-human animal, wherein the genetic modification comprises a knockout of a Pint.

42. The genetically modified non-human animal of embodiment 41, which is a rodent.

43. The genetically modified rodent of embodiment 42, wherein the rodent is selected from a mouse and a rat.

44. A mouse that exhibits a premature aging-associated phenotype, wherein the mouse comprises a knockout of a Pint.

45. The mouse of embodiment 44, wherein the mouse exhibits a phenotype selected from slow weight gain, earlier body weight plateauing, premature growth arrest, lordokyphosis by 12 weeks of age, severe lordokyphosis by 26 weeks of age, loss of fur at six months, loss of hind limb muscle strength at 6 months, and a combination thereof.

46. A genetically modified non-human animal comprising a knockout of a lincRNA selected from the group consisting of HOTAIR, HOTTIP, Hoxa11os, Pantr1, Pantr2, Ptgs2os2, Eldr, Lincenc1, Mannr, Fendr1, Halr1, Haglr, Celrr, Crnde, Kantr, Pint, Trp53cor1, lincppara, Haglr, Tug1, and a combination thereof.

47. The genetically modified mouse of embodiment 46, which is a rodent.

48. The genetically modified rodent of embodiment 47, which is a mouse or a rat.

EXAMPLES

Example 1

Construction of Targeting Vectors

VelociGene® methods were employed, as described previously, which allows for the rapid and high-throughput generation of custom gene mutations in mice (Valenzuela, D. M., et al. (2003b), *Nat Biotechnol* 21:652-659). Briefly, BacVec large targeting vectors (LTVEC) were generated using BAC clones from the mouse bMQ (129S7/SvEv Brd-Hprt b-m2) or RP23 BAC library (Adams, D. J., et al. (2005), *Genomics* 86:753-758). The lacZ/neo$^r$ reporter/selection cassette (FIG. 1) was identical to the ZEN-Ub1 cassette used for the NIH KOMP (sequence available at www.velocigene.com/komp/detail/10020) except that the amino-terminal end of the β-galactosidase coding sequence in the lacZ part was modified to include an ATG start codon and a Kozak consensus sequence (Kozak, M. (1987) *Nucleic acids research* 15: 8125-8148)).

Example 2

ES Cell Targeting

LTVECs were introduced into VGF1 F1 hybrid (129S6SvEvTac/C57BL6NTac) ES cells (Poueymirou et al. (2007); Valenzuela et al. (2003a)) with a multi-well electroporation device (Harvard Apparatus, Boston, Mass.) in electroporation buffer (Millipore) $3.3 \times 10^6$ cells, 0.67 µg DNA in a volume of 0.125 ml followed by culturing on 15 cm gelatinized plates. Selection medium containing G418 was added 48 hours after electroporation and changed daily thereafter. Drug-resistant colonies were picked 10 days after electroporation, treated with trypsin and cultured in gelatinized 96-well plates for at least three days before DNA extraction and purification. Correctly targeted ES cell clones were identified by the loss-of-allele assay (Frendewey et al. (2010), *Methods in enzymology* 476:295-307; Valenzuela et al. (2003a), *Nat. Biotechnol.* 21:652-659).

Example 3

Making LincRNA Mice

The VelociMouse® method (Dechiara, T. M., (2009), *Methods Mol Biol* 530:311-324; Poueymirou et al. (2007), *Nat. Biotechnol.* 25:91-99) was used, in which targeted ES cells were injected into uncompacted 8-cell stage Swiss Webster embryos to produce fully ES cell-derived F0 generation mice carrying the lincRNA knockout mutations. Male VelociMice® were used directly for lacZ expression profiling or mated with C57BL/6NTac females to produce embryos or adults for lacZ analysis or to produce F1 breeders and phenotypic studies were performed on N2F1 mice. Timed matings were carried out by assigning the morning of identification of vaginal plugs as day 0.5 (E0.5)

Example 4

LacZ Expression Profiling

For whole-mount staining, E9.5 and E14.5 embryos were collected, washed in PBS and incubated for 15 to 60 minutes in fresh 0.2% glutaraldehyde solution. Embryo yolk sacs were taken for genotyping. After fixation, embryos were washed in wash buffer and incubated in X-gal (1 mg/mL) staining solution at 37° C. for 1 to 24 hours. After staining, tissues were rinsed in wash buffer, post-fixed in 4% paraformaldehyde, and incubated in 70% ethanol for at least 24 hours. E9.5-e11.5 embryos were photographed immediately while e12.5 embryos and older were cleared in a series of solutions containing increasing glycerol and decreasing 1% KOH in ddH$_2$O. Photographs were taken with a Nikon SMZ800 stereomicroscope. Lungs from Fendrr e13.5 embryos were dissected for photography after clearing.

For studies with adult mice, 6 to 8-week old F0 generation fully ES cell-derived VelociMice® were deeply anesthetized and fixed by cardiac perfusion using a 0.2% glutaraldehyde/ 4% paraformaldehyde solution. Brain, ribcage, heart, lung, liver, spleen, stomach, kidney, intestine, urogenital, muscle, and hind limb tissues were dissected, rinsed in PBS and post-fixed for 30 minutes in a 0.2% glutaraldehyde/4% paraformaldehyde solution. Tissues were then washed and incubated in X-gal (1 mg/mL) staining solution for 1 to 24 hours at 37° C. After staining, tissues were rinsed in wash buffer, post-fixed in 4% paraformaldehyde, cleared in a series of 50%, 70% and 100% glycerol and photographed as for the embryos.

Example 5

Animal Care and Experimental Procedures

Phenotypic studies of N2F1 mice began at 6-8 weeks of age. For timed matings, we assigned the morning of identification of vaginal plugs as embryonic day 0.5 (E0.5). LincRNA KO and wild-type littermates were observed from birth for various developmental milestones (runting, breathing, facial and limb abnormalities, skin color, posture, righting and eye opening) until about 6-8 weeks of age, when they were housed in 12 h of light per day at 69-74 F, and 40-60% humidity for study. All experiments began at 6-8 weeks of age and all animal procedures were conducted in compliance with protocols approved by the Regeneron Pharmaceuticals Institutional Animal Care and Use Committee.

Example 6

µCT Analysis 3D skeletal imaging was visualized using the Quantum FX microCT Pre-clinical In-Vivo Imaging System (Perkin Elmer). Mice were anesthetized using oxygen/isofluorane inhalation with an isofluorane flow rate of 2.5 L/min and an oxygen flow rate of 1.5 L/min. During the scan, anesthesia was maintained at 0.25 L/min oxygen flow rate through a nose cone. Scans were performed at 90 kV and 160 µA with a 30 mm field of view for hindlimbs and a 60 mm field of view for vertebrae. For bone mineral density, total bone, lean and fat volume analysis, two consecutive scans were performed with 60 mm field of view for whole body excluding the head. The right femur was manually isolated for bone mineral density measurements. Right femur, total lean and total fat volumes were all measured using Analyze 11.0 software (Mayo Clinic) and converted to mass based on established densities. Following the scan, mice were returned to their cage and monitored for recovery in compliance with Regeneron IACUC protocols.

Example 7

Tail Suspension Test

When suspended by the tail, mice prepare for a safe landing by spreading their hind limbs, often referred to as "hindlimb splay". Mice were suspended by their tails for 10 s and observed for any abnormal clasping phenotype.

Example 8

Grip Endurance Test

Mice were evaluated at 5, 7, and 10 weeks of age for signs of muscular deficit by their ability to hang inverted from a wire grid (wire thickness approximately 2 mm). Mice were individually placed on a wire grid that was gently shaken to prompt them to hold on as the grid was turned upside down. The time taken for the mouse to let go (up to a maximum of 60 seconds) was recorded. Mice were given three attempts to hold on as long as possible and the maximum time was recorded for statistical comparison.

Example 9

Muscle Histology and Tissue Necropsy

Mice were euthanized by $CO_2$ inhalation followed by cervical dislocation. The tibialis anterior (TA), quadriceps and gastrocnemius (GA) muscles were dissected and weighed. All collected muscles and organs were frozen and were kept at −80 C for future examination. For histology, muscles were frozen in OCT, cryo-sectioned crossly at 12 μm thickness to reveal lateral and medial head, soleus, and plantaris. Adjacent sections were stained with H & E, laminin, and MHC Slow Stain. The stainings were digitally imaged using Aperio Scanscope. Fiber size and count were determined using Spectra software. All data are expressed as means +/− the standard error of the mean (represented as error bars). Analysis of variance (ANOVA) was conducted using the program STATVIEW and/or PRISM. Statistical significance was set at a P value less than 0.05. For skin histology, dorsal and ventral skin areas were shaved, dissected and fixed in 4% paraformaldehyde (PFA) for at least 24 hours and transferred to 70% ethanol. Paraffin embedding, sectioning and hematoxylin and eosin staining on skin sections were performed by Histoserv Labs, Inc., Germantown, Md.

Example 10

Kaplan-Meier Survival Curve Analysis

Animals were observed for a period of 52 weeks and monitored for signs of morbidity according to Regeneron IACUC protocols. No mice in this study needed to be sacrificed prior to the 52-week time point based on morbidity guidelines. Survival curve and log rank test were determined using Graphpad PRISM 6 software.

Example 11

Diverse Phenotypes and Specific Transcription Patterns in Twenty Mouse Lines with Ablated lincRNAs In a survey of 20 knockout mouse lines designed to examine the biological functions of large intergenic non-coding RNAs (lincRNAs), we have found a variety of phenotypes, ranging from perinatal lethality to defects associated with premature aging and morphological and functional abnormalities in the lungs, skeleton, and muscle. Each mutant allele carried a lacZ reporter whose expression profile highlighted a wide spectrum of spatiotemporal and tissue-specific transcription patterns in embryos and adults that informed our phenotypic analyses and will serve as a guide for future investigations of these genes. Our study shows that lincRNAs are a new class of encoded molecules that, like proteins, serve essential and important functional roles in embryonic development, physiology, and homeostasis of a broad array of tissues and organs in mammals.

It has recently become clear that an in-depth understanding of the relationship between genotype and phenotype in mammals requires that we expand our investigations beyond the protein-coding genes to include the non-coding portion of the genome (Mattick J S (2009) *PLoS genetics* 5: e1000459). Large-scale whole genome expression studies in mammalian cells have revealed that approximately three-quarters of the genome is capable of being expressed as RNA (Kapranov P, et al. (2007) *Science* 316: 1484-1488; Carninci P, et al. (2005) *Science* 309: 1559-1563; Djebali S, et al. (2012) *Nature* 489: 101-108), and most of the transcripts do not code for proteins. Among the non-coding transcripts is a diverse class known as long non-coding RNAs (lncRNAs). Representing approximately 15,000 transcripts from nearly 10,000 genomic loci in human cells (Derrien T, et al. (2012) *Genome Research* 22: 1775-1789), lncRNAs and a subclass known as large intergenic non-coding RNAs (lincRNAs) (Guttman M, et al. (2009) *Nature* 458: 223-227; Khalil A M, et al. (2009) *Proceedings of the National Academy of Sciences of the United States of America* 106: 11667-11672) resemble protein-coding mRNAs in structure, synthesis, and the chromatin character of their genes. Whether or not this structural similarity extends to a functional diversity that matches that of proteins remains an open question.

Since the creation of the first knockout strain nearly twenty-five years ago, the mouse has become the premier system for the study of mammalian gene function (Capecchi M R (2001) *Nat Med* 7: 1086-1090; Evans M J (2001) *Nat Med* 7: 1081-1083; Smithies O (2001) *Nat Med* 7: 1083-1086). With few exceptions, the application of knockout mouse technology in individual gene studies as well as large-scale international projects (www.knockoutmouse.org) has focused on protein-coding genes, but the recent efforts to create global knockout mouse resources for microRNAs (Prosser H M, et al. (2011) *Nature biotechnology* 29: 840-845) (mcmanuslab.ucsf.edu/microrna_knockout) demonstrate the value of applying the technology to non-coding RNAs. There have been a few functional studies of individual lncRNAs by gene disruption in mice, but about half have focused on well-studied lncRNAs involved in a single, related biological phenomenon: X chromosome inactivation (Marahrens Y, et al. (1997) *Genes & Development* 11: 156-166; Sado T, et al. (2001) *Development* 128: 1275-1286) and somatic chromosome imprinting (Leighton P A, et al. (1995) *Nature* 375: 34-39; Mohammad F, et al. (2010) *Development* 137: 2493-2499; Sleutels F, et al. (2002) *Nature* 415: 810-813; Takahashi N, et al. (2009) *Human Molecular Genetics* 18: 1879-1888).

Recently, disruption of the mouse Fendrr lncRNA resulted in embryonic lethality associated with defects in heart and body wall development (Grote P, et al. (2013) *Developmental Cell* 24: 206-214). However, deletion or insertion mutations in the lncRNA-encoding Gt(ROSA)26Sor (Zambrowicz B P, et al. (1997) *Proceedings of the National Academy of Sciences of the United States of America* 94: 3789-3794) or Malat1 (Zhang B, et al. (2012) *Cell Reports* 2: 111-123) genes produced no discernable phenotypes. The emerging understanding of the structure, expression, and function of the lncRNA genes presents a new opportunity to employ mouse molecular genetics to reveal the biological functions associated with this new class of genes.

Applying knockout mouse technology to lncRNAs does, however, present some technical challenges. Most proteins have elements or domains that are known or at least predicted to be of functional relevance. Deleting the coding sequences for these essential parts is often sufficient to create a null allele. Likewise, conditional alleles can be designed that isolate the critical exon or exons for later deletion by the action of a tissue specific recombinase. Because structure-function relationships have not yet been established for all but a few lncRNAs and there is no open reading frame as a guide, the knockout strategies available to protein-coding genes may not be applicable to the genomic loci that encode lncRNAs. Although the annotation of lncRNA genes has improved (Derrien T, et al. (2012) *Genome Research* 22: 1775-1789), the precise boundaries of some genes may still remain ambiguous, which can complicate knockout allele design. A powerful tool applied to knockout mice for protein-coding genes is the replacement of the target gene with a reporter, such as the coding sequence for β-galactosidase or a fluorescent protein, whose expression is controlled by the target gene's promoter, thereby reporting the spatial and temporal pattern of its expression in the mouse. Reporter gene replacement has been applied successfully to non-coding RNAs such as the well-studied Gt(ROSA)26Sor locus (Zambrowicz B P, et al. (1997) *Proceedings of the National Academy of Sciences of the United States of America* 94: 3789-3794), which encodes a lncRNA, and the gene for the small non-coding RNA miR-155 (Thai T H, et al. (2007) *Science* 316: 604-608), but rules for creating such alleles for lncRNAs may need to be developed. Despite these qualifications, with thousands of lncRNAs identified, the time is ripe to apply the power of knockout mouse technology to this new class of genes. With this goal in mind, we describe here a unified genetic approach to elucidate the functions of twenty lincRNAs by the creation of knockout mouse lines, each carrying a gene-ablating deletion allele with a β-galactosidase reporter replacement.

Generation of 20 lincRNA-Deleted Mouse Lines with Reporter Gene Replacement

Table 1 lists the 20 lincRNA genes on 10 different chromosomes targeted in this study and the 26 knockout deletion alleles created. We chose to mutate members of the large intergenic non-coding RNA class because, by definition, lincRNA genes are isolated from neighboring protein-coding genes and their transcripts do not overlap (Guttman M, et al. (2009) *Nature* 458: 223-227). This feature allowed us to design deletion alleles that would have the least chance of interfering with the expression of nearby genes. We chose the targeted lincRNA genes to reflect a variety of expression patterns (Khalil A M, et al. (2009) *Proceedings of the National Academy of Sciences of the United States of America* 106: 11667-11672; Cabili M N, et al. (2011) *Genes & Development* 25: 1915-1927), with an emphasis on neural expression, and for their potential involvement in development and the regulation of gene expression.

Our design strategy for the lincRNA knockout mutations was guided by two goals. First, we aimed to create alleles that would accurately report the transcription activity of the lincRNA genes. Although there was evidence from cell-based and selected tissue dissection studies for tissue-specific lincRNA expression (Cabili M N, et al. (2011) *Genes & Development* 25: 1915-1927), we wanted to complement this knowledge base by producing the higher definition expression patterns afforded by lacZ expression profiling, which can resolve tissue and organ expression both spatially and temporally, thereby, revealing subdomains and in some cases, cell-type specificity not resolved by tissue dissection experiments. Second, we strove to create gene-ablating deletions that abolished the synthesis and function of the lincRNA so that any phenotypes associated with the mutations would be informative about the critical functions of the targeted RNAs.

The knockout deletions ranged in size from about 400 bp to 50 kb, with half deleting all of the annotated exons. For most of the remaining alleles, the deletion started in the second exon. The application of VelociGene® methods (Valenzuela D M, et al. (2003) *Nature Biotechnology* 21: 652-659) for the construction and use of large targeting vectors based on bacterial artificial chromosomes (LTVECs) was crucial to enabling us to make the large, gene ablating deletions required to ensure a null allele for this new class of large functional RNA.

Little is known about the relationship between structure and function for lincRNA genes that could guide allele design. Experience with the disruption of the Gt(ROSA) 26Sor (Zambrowicz B P, et al. (1997) *Proceedings of the National Academy of Sciences of the United States of America* 94: 3789-3794) and BIC (miR-155) (Thai T H, et al. (2007) *Science* 316: 604-608) genes established that deletion and insertion after the first exon can produce reliable and tissue-specific expression of β-galactosidase or other reporters. This strategy might, however, fail to achieve a complete null mutation if the fusion transcript from the modified allele retains a functional part of the lincRNA from the 5' portion encoded in the first exon (Tsai M C, et al. (2010) *Science* 329: 689-693). The knockout allele designs indicated in Table 1 were therefore a compromise between the desire for a completely ablating mutation that would have the highest probability of abolishing lincRNA function and the goal of creating an allele that produced an accurate and informative gene expression profile from the β-galactosidase reporter. For example, for the HOTAIR gene we made two alleles, one that deleted nearly the entire RNA coding sequence and a second in which the deletion started in the second exon. Both alleles produced identical phenotypes (described below), but only the second functioned as a reporter of gene expression.

For lincRNAs that reside very near a protein-coding gene and may share a divergent promoter, we set the deletion start point in the second exon to avoid the chance of disrupting the transcription of the neighboring gene. FIG. 1 shows such an example for the Fendrr gene. The diagram shows the design elements common to all the alleles: a targeted deletion of all or most of the sequence coding for the lincRNA and replacement with a cassette that contains a sequence from the *E. coli* lacZ gene that encodes β-galactosidase and a cassette (neo$^r$) that expresses neomycin phosphotransferase for the selection of G418-resistant ES cell colonies. LoxP recombinase recognition sites that enable Cre-mediated excision prior to phenotypic analysis flank the drug selection cassette. As there is no functional open reading with which to fuse the lacZ sequence, each allele carries a start codon and a Kozak consensus sequence (Kozak M (1987) *Nucleic acids research* 15: 8125-8148) for efficient translation of the β-galactosidase reporter.

Specific and Diverse LincRNA Gene Expression Patterns Revealed by LacZ Reporter Profiling To survey the expression patterns of the 20 targeted lincRNA genes, we applied X-gal staining for β-galactosidase activity on mid-gestation embryos and adult whole mount tissues and organs. The targeted lincRNA genes exhibited a variety of unique reporter gene expression patterns in both embryos and adults, representing most of the major organ systems and tissue types (Table 2 at FIG. 11). For example, in the adult tissues, expression of Pantr2, Kantr, and Peril was restricted to the brain; Mannr and Fendrr were expressed in lungs; Eldr was expressed in the urogenital system; and Halr1 was expressed in the ribcage. One lincRNA gene, Pint, exhibited ubiquitous expression in all tissues. We did not detect expression of the Hotair, Ptgs2os2, and Haglr genes in any of the adult tissues we examined.

Embryonic expression appears to be a common feature of lincRNAs. Examination of the β-galactosidase reporter expression in heterozygous embryos at or around embryonic day 12.5 (E12.5) revealed a variety of specific patterns for all 20 targeted lincRNA genes (Table 2 at FIG. 11, FIG. 2A). The expression profiles ranged from ubiquitous (Tug1) to highly specific, such as epidermal for Eldr, whisker placode for Trp53cor1 (FIG. 9), or the mammary buds for lincenc1 (FIG. 9). The spatiotemporal patterns seen in the different extents of limb bud and tail expression for Hottip and Hoxa11os are very similar to those reported for the adjacent protein-coding genes in the HoxA cluster (Hostikka S L, Capecchi M R (1998) *Mechanisms of Development* 70: 133-145; Lu P, et al. (2008) *Development* 135: 1395-1405). The expression of Hotair in the posterior tail bud and genital tubercle that we observed for the β-galactosidase reporter was identical to that determined by in situ hybridization (Schorderet P, Duboule D (2011) *PLoS genetics* 7: e1002071). Analysis of X-gal staining at different points during embryonic development showed that for some of the lincRNA genes, expression began early at a restricted site and then extended beyond this initial locus at later stages (FIG. 2B), again reminiscent of Hox protein expression (Nagy A (2003) Manipulating the mouse embryo: a laboratory manual. 3rd ed. Cold Spring Harbor, N.Y.: Cold Spring Harbor Laboratory Press. pp. x, 764 p.). For example, the expression of the Hottip and Hoxa11os genes began in the extreme posterior of the E9.5 embryo and then extended into the limb buds at later times. Similarly, the initial expression for Celrr at a site near the anterior end of the E9.5 embryos was maintained and expanded to the neural tube over the next two days.

Consistent with the frequent brain expression seen among human tissue-specific lncRNAs (Derrien T, et al. (2012) *Genome Research* 22: 1775-1789), we found that half of the 20 targeted mouse lincRNA genes were transcriptionally active in the adult brain. As with the embryonic lincRNA expression, the brain patterns (FIG. 3) were unique and varied from ubiquitous (lincppara and Pint) to highly restricted specific brain structures (Peril, Crnde, and Kantr).

Pint's Unique Increased Expression with Age Correlates with an Aging-Like Phenotype Of the 20 lincRNA genes targeted, only Pint showed a global whole-body expression pattern, mostly restricted to postnatal life (Table 2 at FIG. 11). Unique to Pint, we observed an increase in its expression with age (FIG. 4). In 3-day old neonates, Pint transcription activity was low (brain) or undetectable (ribcage muscle) but then gradually appeared in 3-week old mice and became strong and ubiquitous by 8 weeks of age. Although the strength and timing of Pint expression varied among different organs and tissues, the general trend was a steady increase in expression after birth to a plateau in adulthood. To our knowledge, this age-related dynamic expression pattern is novel. We have not observed a similar profile in our experience of lacZ profiling experiments for hundreds of protein-coding genes (Valenzuela D M, et al. (2003) *Nature Biotechnology* 21: 652-659).

The striking age-related increase in whole-body Pint expression revealed by lacZ profiling (FIG. 4) suggested a global homeostatic role for Pint in the maintenance of normal health as mice age. To test this hypothesis we bred the Pint knockout mouse line to homozygosity and conducted a longitudinal study comparing homozygous (Pint$^{-/-}$) mice with wild type (WT) and heterozygous (Pint$^{+/-}$) littermate controls. The Pint$^{-/-}$ mice appeared healthy and normal at birth; however, at the age of 3 months they began to show signs of an early onset aging-like phenotype. Body weight measurements revealed that both male and female Pint$^{-/-}$ mice exhibited a slower growth rate compared with their WT littermates, but it was more pronounced in the males (FIG. 5A). By one year of age, male Pint$^{-/-}$ mice were more than 30% lighter and Pint$^{+/-}$ mice were 15% lighter than their WT littermates, whereas Pint$^{-/-}$ females were 27% lighter (data not shown). Kaplan-Meier analysis comparing homozygous with heterozygous and WT male mice (FIG. 5B) demonstrated that the loss of Pint is associated with poor survival outcome. We found no sign of tumors or lesions in the mutant mice as they aged, but some Pint$^{-/-}$ mice developed herniation, including protrusion of the xiphoid process on the chest associated with thinning of the abdominal wall (data not shown). There was an age-dependent abnormal hindlimb clasping posture when the mice were suspended from their tails (data not shown). The severity of this phenotype varied, but its frequency increased progressively with age, suggesting a decline of muscle strength (see FIG. 8 for another example in the Hottip knockout line). We also observed fur loss in both male and female mice (data not shown). Histological analysis of skin sections collected from the ventral and dorsal bodies of Pint$^{-/-}$ mice revealed fibrosis and a noticeable difference in hair follicle development along with a dramatic reduction in the thickness of the subcutaneous fat layer (FIG. 5C).

Non-invasive whole body analysis by X-ray microtomography (microCT) of individual mice as they aged indicated a significantly lower fat content in male (FIG. 5D) and female (FIG. 5E) Pint$^{-/-}$ mice compared with their WT littermates. The loss of total body fat was likely the major contributor to the decline in body weight as they age (FIG. 5A). The Pint$^{-/-}$ mice also had a significantly lower femur bone mineral density than WT (FIGS. 5F and 5G). Male mice had significantly decreased lean mass at 52 weeks of age. Both males and females showed significantly decreased muscle mass for the gastrocnemius complex (GA) and tibialis anterior (TA) beginning at 26 weeks of age (not shown). Skeletal imaging revealed the appearance of severe lordokyphosis in both male and female Pint$^{-/-}$ mice compared with WTs (FIG. 5H). Approximately 70% of 12-week old Pint$^{-/-}$ mice displayed lordokyphosis and 100% by 52 weeks of age (FIG. 5I). In contrast, only 10 to 20% of 26-week old WT mice displayed slight lordokyphosis and this frequency did not increase with age. Pint$^{-/-}$ mice did not develop significant lordokyphosis until 26 weeks of age, indicating an unusual age-dependent haploinsufficiency for Pint. The spectrum of age-associated pathologies in the Pint knockout mice suggests that Pint may be important for the maintenance of health and the avoidance of pre-mature aging during the normal life span of the mouse.

Loss of Fendrr Causes Perinatal Lethality as the Result of Respiratory Distress

Of the 20 lincRNA knockout mouse lines, Peril$^{-/-}$ and Fendrr$^{-/-}$ mice showed perinatal lethality. Our Fendrr knockout allele has a 26 kb deletion from exon 2 to the last annotated exon (FIG. 1). X-gal staining of E12.5 homozygous embryos showed lacZ expression in the frontonasal process, upper respiratory tract, lungs, and the posterior Aorta-Gonad-Mesonephron (AGM) region (FIG. 6A) that was identical in both heterozygous (not shown) and homozygous embryos, indicating grossly normal organogenesis. An isolated look at the developing lungs at E13.5 revealed defects in the knockout embryos: the lungs were small and the lobes appeared globular and disorganized (FIG. 6B). Mice homozygous for deletion of the Fendrr gene survived to birth but succumbed shortly after from apparent breathing problems. The Fendrr mutant perinatal lethal phenotype was identical in mice on 2 different genetic backgrounds: a C57BL6/129 hybrid reported here and in mice further backcrossed to C57BL/6 in a separate breeding program (Sauvageau M, et al. (2013) *Elife* 2: e01749).

Loss of Hotair and Hottip Causes Morphological and Functional Defects in Skeleton and Muscle Embryonic X-gal staining for the Hotair and Hottip genes showed restricted expression in the posterior and distal limb buds (FIG. 2A). Consistent with these developmentally restricted expression patterns, deletions of the Hotair and Hottip genes caused morphological malformations in the tail and hind limbs of adult mice. In Hotair$^{-/-}$ mice we observed an apparent homeotic transformation of the 4th caudal vertebra, which became anatomically similar to the 3rd caudal vertebra (FIG. 7). The Hottip$^{-/-}$ mice displayed an abnormal hindlimb clasping posture when suspended from their tails compared with wild type littermates (FIG. 8A). This behavioral abnormality was accompanied by a loss in grip endurance as measured by a test in which the mice are challenged to remain suspended on an inverted wire cage. Wild type and Hottip$^{+/-}$ mutants held on for approximately one minute, while their homozygous littermates released their grip within 10-20 seconds (FIG. 8B). This apparent reduction in grip strength was associated with a loss of muscle mass for the gastrocnemius but not for the tibialis anterior or the quadriceps muscles (FIG. 8C). We observed an approximate 40% reduction in the number of muscle fibers in the gastrocnemius but no reduction in average fiber size (FIGS. 8D and E). In addition to the muscle defects in the Hottip knockout mice, we also found a hindlimb skeletal malformation: a shortening in the length of the calcaneum bone (FIG. 10).

In the past several years there has been an explosion in our understanding of the non-protein-coding component of the genome, especially in mammals. In addition to long-recognized classes of non-coding functional RNAs such as ribosomal, transfer, small nuclear, small nucleolar, small cytoplasmic RNAs, the RNA components of the RNase P, RNase MRP, and telomerase enzymes and the more recently discovered microRNAs and the PIWI-associated piRNAs, we can now include at least 15,000 members of the long non-coding RNA class (Kapranov P, et al. (2007) *Science* 316: 1484-1488; Carninci P, et al. (2005) *Science* 309: 1559-1563; Djebali S, et al. (2012) *Nature* 489: 101-108; Derrien T, et al. (2012) *Genome Research* 22: 1775-1789; Guttman M, et al. (2009) *Nature* 458: 223-227). As we begin to understand the genomic presence and expression of lncRNA genes, the next goal is to discover their biological functions. As a first step to tackling this challenge, we applied mouse gene targeting technology, the most powerful tool for the determination of mammalian gene function, to create a resource of knockout mouse lines for 20 lincRNA genes (Sauvageau M, et al. (2013) *Elife* 2: e01749).

Structure-function relationships for the lincRNAs are poorly understood. For this reason, it was crucial in this initial study to create knockout alleles with deletions that removed most if not all of the lincRNA coding potential to have the highest probability of creating a loss-of-function mutation. The ambiguous and incomplete annotation of many lincRNA loci, with multiple reported transcripts perhaps generated by alternative splicing or transcription initiation sites, adds to the difficulty of knockout allele design. New understanding of the molecular characteristics important for lincRNA function should inform the design of the next generation of lincRNA alleles with more precisely directed modifications of sequences critical to function and also permit advanced and flexible conditional strategies.

A key goal of our lincRNA knockout survey was to create alleles that in addition to abolishing function also reported the gene's spatiotemporal pattern of expression. Despite not having a protein coding open reading frame as a guide, we were successful in designing alleles that reported gene expression for all of the 20 targeted genes. One of the alleles that produced no lacZ expression in the adult stage was Ptgs2os2 (see FIG. 2A and FIG. 9 for embryonic expression), which is known to be one of the lincRNAs most strongly induced by inflammatory signals (Guttman M, et al. (2009) *Nature* 458: 223-227; Carpenter S, et al. (2013) *Science* 341(6147): 789-92). The Ptgs2os2 knockout line should prove a valuable resource for studies of how a lincRNA's expression responds to infection or other inflammatory insults and what biological role it plays in the process.

One of the criteria we applied in our selection of which lincRNA genes to target for this survey was an expectation of expression in neural tissues. Ten of the targeted genes showed lacZ reporter expression in the adult brain and each exhibited a unique pattern (FIG. 3), ranging from strong whole brain expression (Pint) to light grey matter expression in most structures (Tug1) to highly restricted expression exclusive to the colliculi (Crnde) or the midline of the hypothalamus (Peril). The variety and specificity of the gene expression patterns in the brain was also evident in other tissues and was similar to those we have seen with reporter alleles for protein-coding genes. Our lincRNA gene lacZ expression profiling patterns were consistent with the tissue-specific expression found by RNA quantification experiments in wild type mouse tissues (Sauvageau M, et al. (2013) *Elife* 2: e01749). Prior to this study, however, the exquisite tissue and cell type specificity of lincRNA gene expression was not appreciated because previous quantification methods could not deliver the high definition and cell-type resolution of lacZ reporter profiling (FIG. 2A).

Embryonic expression was a feature shared by all the lincRNA genes we examined. LacZ profiling delivered a high definition view of whole embryos that revealed the broad range of specific patterns unique to each lncRNA. Examples include the exquisitely specific expression observed in the whisker placode for Trp53cor1 and the mammary bud for lincenc1, the epidermal expression of Eldr, the limb bud expression of Hottip and Hoxa11os, and the ubiquitous expression of Tug1 (FIGS. 2A, FIG. 2B and FIG. 9). These varied patterns might point to a common role for lincRNAs in the regulation of key events in development.

Another value of lacZ profiling is that it can guide and focus the design of phenotypic studies. For example, the highly restricted posterior expression patterns for heterozygote Hotair and Hottip embryos suggested that we might find knockout phenotypes in posterior body parts. Consistent with this expectation, we observed an apparent homeotic transformation of the 4th caudal vertebra in Hotair$^{-/-}$ mice (FIG. 6), and we found abnormalities of the hind limbs that included muscle weakness and skeletal malformations in Hottip$^{-/-}$ mice (FIG. 8 and FIG. 10). The Hotair homeotic phenotype has also been observed in mice with a different Hotair knockout allele (H. Chang, personal communication). We found that expression of Fendrr in heterozygotes was restricted to the lungs in adult mice (Table 2 at FIG. 11) and prominent in the developing respiratory tract in embryos (FIG. 2A). Perhaps not surprisingly, Fendrr homozygotes exhibited respiratory stress and subsequent perinatal death due to defective structural maturation of the lungs. Our Fendrr knockout phenotype resembles the rare human lethal lung development disorder alveolar capillary dysplasia with misalignment of pulmonary veins (ACD/MPV), in which patients exhibit a deficiency in lung lobe development and suffer postnatal respiratory distress within minutes to hours after birth (Bishop N B, et al. (2011) *American Journal of Respiratory and Critical Care Medicine* 184: 172-179). At least one ACD/MPV patient was reported to have an 11 kb deletion within the FOXF1-AS1 gene, the human homolog of mouse Fendrr, expressed in normal newborn human lungs (Szafranski P, et al. (2013) *Genome Research* 23: 23-33). Grote et al. (Grote P, et al. (2013), *Developmental Cell* 24: 206-214) reported a mutant mouse with a modification of the Fendrr gene that produced lethality at around E13.75 associated with a prominent omphalocele, reduction in ventral body wall thickness, and a heart defect causing blood accumulation in the right atrium. We did not observe any of these phenotypes. The discrepancies between the phenotypes may be explained by the different allele designs. Our allele deleted Fendrr exon 2 to the end, designed to avoid disruption of the promoter that could be shared with the adjacent Foxf1 protein-coding gene. The Fendrr allele of Grote et al. (Grote P, et al. (2013), *Developmental Cell* 24: 206-214) consisted of the insertion of a transcriptional stop element in the first exon and did not include a reporter gene.

The most remarkable adult expression pattern we observed was for Pint, which exhibited an increase in the extent and intensity of X-gal staining as the mice aged from newborn to mature adults (FIG. 4). This striking age-associated pattern prompted us to conduct a longitudinal analysis for growth rate and overt signs of abnormal health. Compared with WT mice, we found that as the Pint$^{-/-}$ mice aged, they exhibited progressive hair loss and signs of muscle weakening, severe lordokyphosis, reduced body fat and bone mineral density, a slower growth rate, and reduced survival. Surprisingly, these results were replicated in the heterozygous mice, but to a lesser extent. This spectrum of age-associated phenotypes, along with the unusual increase in gene expression with age, implies that mice may require a critical dose of Pint for the general maintenance of health and tissue function during the normal life span, and for the first time points to potential role of LincRNA in physiological aging. A recent study showed that Pint is a direct target for p53, providing a link between the p53 pathway and epigenetic silencing by the polycomb repressive complex 2 (PRC2) (Marin-Bejar et al., 2013). A growing body of evidence has implicated the critical role of p53 in cellular senescence and the control of aging. It will be of great interest to investigate the regulation of Pint and its potential involvement in p53-dependent cellular senescence and organismal aging. This could reveal key mechanisms in the physiological aging process in mammals with potential clinical implications in human diseases including those associated with aging and cancer.

Our aim in initiating this work was not only to shed light on the functions of the 20 particular lincRNAs whose genes we chose to mutate, but also to obtain a better understanding of the general properties of lncRNAs as a class. This collection could serve as a seed for a larger-scale effort to mutate many more members of the lincRNA gene family. Many lincRNAs have been shown to be associated with proteins that participate in the regulation of transcription at the chromatin level. This might suggest a broad, general, and redundant function in gene expression much like the interplay of miRNAs in the maintenance of tissue-specific gene expression profiles at the post-transcriptional level. Our results, however, appear to point in a different direction. The unique phenotypes and exquisitely specific expression patterns described here and in Sauvageau et al. (Sauvageau M, et al. (2013) *Elife* 2: e01749) argue for specific, direct, and determinative functions for lincRNAs. Although this study is only the beginning of the analysis of this collection of knockout mice, it reveals lincRNAs as a new class of functional encoded molecules that, like proteins, serve diverse roles in the embryonic development, physiology, and homeostasis of a broad array of tissues and organs in mammals.

We claim:

1. A method of screening for expression of a long intergenic non-coding RNA (lincRNA) encoded by a lincRNA gene, the method comprising
   (a) obtaining a genetically modified rodent comprising a reporter gene incorporated into its genome by homologous recombination,
   wherein the reporter replaces either
   (i) a second exon of the lincRNA gene, a last exon of the lincRNA gene, and all the nucleic acids between the second exon and the last exon of the lincRNA gene or
   (ii) a first exon of the lincRNA gene, the last exon of the lincRNA gene, and all the nucleic acids between the first exon and the last exon of the lincRNA gene
   such that an endogenous promoter of the lincRNA gene locus controls expression of the reporter gene;
   (b) expressing the reporter gene under the control of the endogenous promoter of the lincRNA gene to determine a spatiotemporal expression pattern of the lincRNA in the genetically modified rodent, and
   (c) determining the expression levels of the reporter gene in an organ system, tissue and/or cell to correlate a loss-of-function of the lincRNA with a mutant phenotype as compared to a wildtype control rodent,
   wherein the rodent is a rat or a mouse, and
   wherein:
   (i) the lincRNA gene is Pantr2,
   wherein the expression pattern is in the developing brain, craniofacial region, neural tube, neocortex, olfactory bulb, cerebellum, hypothalamus, and/or basal forebrain;
   (ii) the lincRNA gene is Fendrr,
   wherein the expression pattern is in the respiratory tract including the lungs and trachea, foregut, frontal nasal region of the face, and/or the aorta gonad mesonephros region of an embryo;
   (iii) the lincRNA gene is HOTTIP, wherein the expression pattern is in the limb buds, foregut, posterior region, and/or the tail;
   (iv) the lincRNA gene is Haglr,
   wherein the expression pattern is in a developing brain, craniofacial region and/or heart of an embryo;
   (v) the lincRNA gene is Kantr, wherein the expression pattern is in the brain;
   (vi) the lincRNA gene is Peril,
   wherein the expression pattern is neuronal, in the hypothalamus, in the heart, and/or in the posterior tail region;
   (vii) the lincRNA gene is Tug1,
   wherein the expression pattern is widespread;
   (viii) the lincRNA gene is Ptgs2os2,
   wherein the expression pattern is in the base of developing forelimbs and hindlimbs of an embryo; or
   (ix) any combination of (i)-(viii).

2. The method of claim 1, wherein expressing in step (b) comprises specifying at least one cell type expressing the reporter gene.

3. The method of claim 1, wherein the reporter gene is expressed during embryogenesis of the rodent, throughout adulthood of the rodent, until death of the rodent, or a combination thereof.

4. The method of claim 1, wherein expressing in step (b) comprises:
   (i) specifying at least one cell type expressing the reporter gene, and
   (ii) surveilling expression of the reporter gene during embryogenesis of the rodent, throughout adulthood of the rodent, until death of the rodent, or a combination thereof.

5. The method of claim 1, wherein the reporter gene is operably linked to a kozak sequence.

6. The method of claim 1, wherein the reporter gene encodes a reporter protein selected from the group consisting of β-galactosidase, green fluorescent protein (GFP), mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof.

7. The method of claim 6, wherein the reporter gene comprises lacZ.

8. The method of claim 1, wherein the rodent is a mouse, and
   wherein the reporter gene replaces:
   (a) all nucleic acids of mouse Pantr2 between genomic coordinates Chromosome 1: 42707143-42713698;
   (b) all nucleic acids of mouse Fendrr between genomic coordinates Chromosome 8: 121054882-121074065 with the insert nucleic acid;
   (c) all nucleic acids of mouse HOTTIP between genomic coordinates Chromosome 6: 52262834-52267603 with the insert nucleic acid;
   (d) all nucleic acids of mouse HOTTIP between genomic coordinates Chromosome 6: 52265374-52267603 with the insert nucleic acid;
   (e) all nucleic acids of mouse Haglr between genomic coordinates Chromosome 2: 74750433-74762886 with the insert nucleic acid;
   (f) all nucleic acids of mouse Kantr between genomic coordinates Chromosome X: 152298544-152327475 with the insert nucleic acid;
   (g) all nucleic acids of mouse Peril between genomic coordinates Chromosome 3: 34767849-34782292 with the insert nucleic acid;
   (h) all nucleic acids of mouse Tug1 between genomic coordinates Chromosome 11: 3639794-3648758 with the insert nucleic acid;
   (i) all nucleic acids of mouse Tug1 between genomic coordinates Chromosome 11; 3639794-3645518 with the insert nucleic acid;
   (j) all nucleic acids of mouse Ptgs2os2 between genomic coordinates Chromosome 1; 150159024-150164899 with the insert nucleic acid; or
   (k) any combination of (a)-(j).

* * * * *

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (1)..(4)
<223> OTHER INFORMATION: R is A or G

<400> SEQUENCE: 1 rccrccatgg                                                          10

<210> SEQ ID NO 2
<211> LENGTH: 13
<212> TYPE: DNA
<213> ORGANISM: Artificial Sequence
<220> FEATURE:
<223> OTHER INFORMATION: Kozak consensus sequence
<220> FEATURE:
<221> NAME/KEY: misc_feature
<222> LOCATION: (7)..(7)
<223> OTHER INFORMATION: R is A or G
```

```
<400> SEQUENCE: 2
gccgccrcca tgg                                                              13
```